US011479756B2

(12) United States Patent
Liang et al.

(10) Patent No.: US 11,479,756 B2
(45) **Date of Patent: *Oct. 25, 2022**

(54) KETOREDUCTASE POLYPEPTIDES FOR THE REDUCTION OF ACETOPHENONES

(71) Applicant: Codexis, Inc., Redwood City, CA (US)

(72) Inventors: Jack Liang, South San Francisco, CA (US); Stephane J. Jenne, Foster City, CA (US); Emily Mundorff, Garden City, NY (US); Charlene Ching, San Jose, CA (US); John M. Gruber, Mountain View, CA (US); Anke Krebber, Palo Alto, CA (US); Gjalt W. Huisman, Redwood City, CA (US)

(73) Assignee: Codexis, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/149,463

(22) Filed: Jan. 14, 2021

(65) Prior Publication Data

US 2021/0139861 A1 May 13, 2021

Related U.S. Application Data

(60) Continuation of application No. 16/253,972, filed on Jan. 22, 2019, now Pat. No. 10,927,351, which is a continuation of application No. 16/126,761, filed on Sep. 10, 2018, now Pat. No. 10,227,572, which is a continuation of application No. 15/915,927, filed on Mar. 8, 2018, now Pat. No. 10,100,288, which is a continuation of application No. 15/840,381, filed on Dec. 13, 2017, now Pat. No. 9,951,318, which is a continuation of application No. 15/353,165, filed on Nov. 16, 2016, now Pat. No. 9,873,863, which is a division of application No. 14/501,416, filed on Sep. 30, 2014, now Pat. No. 9,528,131, which is a continuation of application No. 13/970,284, filed on Aug. 19, 2013, now Pat. No. 8,852,909, which is a continuation of application No. 13/682,600, filed on Nov. 20, 2012, now Pat. No. 8,512,973, which is a division of application No. 12/210,195, filed on Sep. 13, 2008, now Pat. No. 8,748,143.

(60) Provisional application No. 60/972,058, filed on Sep. 13, 2007.

(51) Int. Cl.
*C12N 9/04* (2006.01)
*C12P 7/22* (2006.01)

(52) U.S. Cl.
CPC .............. *C12N 9/0006* (2013.01); *C12P 7/22* (2013.01); *C12Y 101/01184* (2013.01); *C12Y 101/01* (2013.01); *Y02E 50/10* (2013.01); *Y02P 20/52* (2015.11)

(58) Field of Classification Search
CPC . C12N 9/0006; C12P 7/22; C12Y 101/01184; C12Y 101/01; Y02E 50/10; Y02P 20/05
See application file for complete search history.

(56) References Cited

U.S. PATENT DOCUMENTS

| | | | |
|---|---|---|---|
| 5,200,335 | A | 4/1993 | Hummel et al. |
| 5,225,339 | A | 7/1993 | Wong et al. |
| 5,342,767 | A | 8/1994 | Wong et al. |
| 5,427,933 | A | 6/1995 | Chen et al. |
| 5,491,077 | A | 2/1996 | Chartrain et al. |
| 5,559,030 | A | 9/1996 | Matsuyama et al. |
| 5,700,670 | A | 12/1997 | Yamagishi et al. |
| 5,891,685 | A | 4/1999 | Yamagishi et al. |
| 6,001,615 | A | 12/1999 | Reeve |
| 6,037,158 | A | 3/2000 | Hummel et al. |
| 6,225,099 | B1 | 5/2001 | Hummel et al. |
| 6,344,569 | B1 | 2/2002 | Mitsuda et al. |
| 6,399,339 | B1 | 6/2002 | Wolberg et al. |
| 6,413,750 | B1 | 7/2002 | Hummel et al. |
| 6,645,746 | B1 | 11/2003 | Kizaki et al. |
| 6,800,477 | B2 | 10/2004 | Patel et al. |
| 7,083,962 | B2 | 8/2006 | Kimoto et al. |
| 7,465,842 | B2 | 12/2008 | Kung et al. |
| 7,498,448 | B2 | 3/2009 | Sturmer et al. |
| 7,820,421 | B2 | 10/2010 | Ching et al. |
| 7,883,879 | B2 | 2/2011 | Campopiano et al. |
| 7,977,078 | B2 | 7/2011 | Liang et al. |
| 8,071,347 | B2 | 12/2011 | Ching et al. |
| 8,088,610 | B2 | 1/2012 | Liang et al. |
| 8,227,229 | B2 | 7/2012 | Liang et al. |
| 8,257,952 | B2 | 9/2012 | Campopiano et al. |
| 8,273,554 | B2 | 9/2012 | Mundorff et al. |
| 8,288,131 | B2 | 10/2012 | Voladri et al. |

(Continued)

FOREIGN PATENT DOCUMENTS

| | | | |
|---|---|---|---|
| JP | 2010-517574 | T2 | 5/2010 |
| JP | 2010-536385 | T2 | 12/2010 |

(Continued)

OTHER PUBLICATIONS

Genbank Accession No. INXQ_A dated Sep. 24, 2008.

(Continued)

*Primary Examiner* — Delia M Ramirez
(74) *Attorney, Agent, or Firm* — Codexis, Inc.

(57) ABSTRACT

The present disclosure provides engineered ketoreductase enzymes having improved properties as compared to a naturally occurring wild-type ketoreductase enzyme. Also provided are polynucleotides encoding the engineered ketoreductase enzymes, host cells capable of expressing the engineered ketoreductase enzymes, and methods of using the engineered ketoreductase enzymes to synthesize a variety of chiral compounds.

13 Claims, 1 Drawing Sheet

Specification includes a Sequence Listing.

(56) References Cited

U.S. PATENT DOCUMENTS

| | | | |
|---|---|---|---|
| 8,288,141 | B2 | 10/2012 | Savile et al. |
| 8,512,973 | B2 | 8/2013 | Liang et al. |
| 8,748,143 | B2 | 6/2014 | Liang et al. |
| 8,852,909 | B2 | 10/2014 | Liang et al. |
| 9,528,131 | B2 | 12/2016 | Liang et al. |
| 9,873,863 | B2 | 1/2018 | Liang et al. |
| 9,951,318 | B1 | 4/2018 | Liang et al. |
| 10,100,288 | B2 | 10/2018 | Liang et al. |
| 10,227,572 | B2 | 3/2019 | Liang et al. |
| 2002/0061564 | A1 | 5/2002 | Rozzell |
| 2003/0054520 | A1 | 3/2003 | Bommanus et al. |
| 2003/0068811 | A1 | 4/2003 | Patel et al. |
| 2004/0265978 | A1 | 12/2004 | Gupta et al. |
| 2006/0195947 | A1 | 8/2006 | Davis et al. |
| 2006/0286646 | A1 | 12/2006 | Patel et al. |
| 2008/0153140 | A1 | 6/2008 | Gupta et al. |
| 2008/0248539 | A1 | 10/2008 | Giver et al. |
| 2008/0318295 | A1 | 12/2008 | Ching et al. |
| 2009/0017510 | A1 | 1/2009 | Gupta et al. |
| 2009/0093031 | A1 | 4/2009 | Liang et al. |
| 2009/0155863 | A1 | 6/2009 | Liang et al. |
| 2009/0311762 | A1 | 12/2009 | Tschentscher et al. |
| 2012/0178142 | A1 | 7/2012 | Ching et al. |
| 2012/0184000 | A1 | 7/2012 | Liang et al. |
| 2012/0276599 | A1 | 11/2012 | Liang et al. |

FOREIGN PATENT DOCUMENTS

| | | | |
|---|---|---|---|
| JP | 2010-539948 | T2 | 12/2010 |
| JP | 5973131 | B2 | 8/2016 |
| JP | 6137758 | B2 | 5/2017 |
| WO | WO 2001/040450 | A1 | 6/2001 |
| WO | WO 2002/086126 | A2 | 10/2002 |
| WO | WO 2004/076412 | A2 | 9/2004 |
| WO | WO 2005/017135 | A1 | 2/2005 |
| WO | WO 2005/018579 | | 3/2005 |
| WO | WO 2005/033094 | A2 | 4/2005 |
| WO | WO 2005/054491 | A1 | 6/2005 |
| WO | WO 2006/021881 | A2 | 3/2006 |
| WO | WO 2006/021884 | A2 | 3/2006 |
| WO | WO 2006/021885 | A1 | 3/2006 |
| WO | WO 2006/021886 | A1 | 3/2006 |
| WO | WO 2007/012428 | A1 | 2/2007 |
| WO | WO 2008/042876 | A2 | 4/2008 |
| WO | WO 2008/103248 | A1 | 8/2008 |

OTHER PUBLICATIONS

Genbank Accession No. AAP94029 dated Apr. 1, 2004.
Genbank Accession No. AJ544275 dated Feb. 17, 2003.
Genbank Accession No. BAA24528.1 dated Jan. 28, 1998.
Genbank Accession No. CAD66648 dated Feb. 17, 2003.
Genbank Accession No. JC7338 dated Jun. 3, 2002.
Genbank Accession No. NP010159.1 dated Jun. 16, 2008.
Genbank Accession No. P41747 dated May 5, 2009.
Genbank Accession No. Q07551 dated Nov. 26, 2006.
Cui, et al., "Structure Based Drug Design of Crizotinib (PF-02341066), a Potent and Selective Dual Inhibitor of Mesenchymal-Epithelial Transition Factor (c-MET) Kinase and Anaplastic Lymphoma Kinase (ALK)," Journal of Medicinal Chemistry (2011), 54(18), 6342-6363.
De Koning, et al., "Fit-for-Purpose Development of the Enabling Route to Crizotinib (PF-02341066)," Organic Process Research & Development (2011), 15(5), 1018-1026.
Martinez, et al., "Biotransformation-mediated synthesis of (1S)-1-(2,6-dichloro-3-fluorophenyl)ethanol in enantiomerically pure form," Tetrahedron: Asymmetry (2010), 21(19), 2408-2412.
Branden, C., et al., "Prediction, engineering, and design of protein structures," in Introduction to Protein Structure, Garland Publishing Inc., New York, Chapter 16, p. 247 (1991).
Seffernick, J.L.,et al., "Melamine deaminase and atrazine cholorohydrolase: 99 percent identical but functionally different," J. Bacteriol., 183(8):2405-2410 (2001).
Witkowski, A., et al., "Conversion of a beta-ketoacyl synthase to a malonyl decarboxylase by replacement of the active-site cysteine with glutamine," Biochemistry, 38:11643-11650 (1999).
Bloom et al. "Evolving strategies for enzyme engineering," Curr. Opin. Struct. Biol. 15: 447-452 (2005).
Fox et al., "Improving catalytic function by ProSAR-driven enzyme evolution," Nature Biotechnology 25(3); 338-344 (2007).
Creaser, E. H., et al., "Protein engineering of alcohol dehydrogenases; effects of amino acid changes at positions 93 and 48 of yeast ADH1," Protein Eng., 3(6):523-526 [1990].
Phillips, R.S., "Tailoring the substrate specificity of secondary alcohol dehydrogenase," Can. J. Chem., 8(6):680-685 [2002].
Wilks, H.M., et al., "Alteration of enzyme specificity and catalysis by protein engineering," Curr. Opin. Biotechnol., 2:561-567 [1991].
Ju, K.-S., et al., "Control of Substrate Specificity by Active-Site Residues in Nitrobenzene Dioxygenase," Appl. Environ. Microbiol. 72(3):1817-1824 [2006].
Amidjojo et al., 2005, "Asymmetric Synthesis of Tert-butyl (3R, 5S)6-chloro-dihydroxyhexanoate with *Lactobacillus kefir," Appl Microbiol Biotechnol*., 69:9-15.
Bisel et al., 2007, "Stereochemical clarification of the enzyme-catalysed reduction of 2-acetylchromen-4-one," *Tetrahedron Asymmetry*, 18(9):1142-1144.
Bradshaw et al., 1992, "*Lactobacillus kefir* Alcohol Dehydrogenase: A Useful Catalyst for Synthesis," *J. Org. Chem*. 57(5):1532-1536.
Breyer-Pfaff et al., 1999, "High-affinity Stereoselective Reduction of the Enantiomers of Ketotifen and of Ketonic Nortriptyline Metabolites by Aldo-Keto Reductases from Human Liver," *Biochem. Pharmacol*., 59:249-260.
Cha et al., 2002, "Stereochemical control in diastereoselective reduction of α-substituted-β-ketoesters using a reductase purified from *Kluyveromyces marxianus," Biotechnol. Lett* , 24:1695-1698.
Database EPO Proteins, Apr. 2007, "Sequence 4 from Patent WO2007012428," retrieved from EBI Accession No. EPOP:CS539287, Database Accession No. CS539287.
Goldberg et al., 2007, "Biocatalytic ketone reduction—a powerful tool for the production of chiral alcohols—part I: processes with isolated enzymes," *Appl Microbiol Biotechnol*, 76(2):237-248.
Gröger et al., 2004, "Preparative asymmetric reduction of ketones in a biphasic medium with an (S)-alcohol dehydrogenase under in situ-cofactor-recycling with a formate dehydrogenase," *Tetrahedron* 60:633-640.
Hönig et al., 1994, "Enzymatic Resolutions of Heterocyclic Alcohols," *Biocatalysis* 9:61-69.
Hummel, 1990, "Reduction of acetophenone to R(+)-phenylethanol by a new alcohol dehydrogenase from *Lactobacillus kefir," Appl Microbiol Biotechnol*, 34(1):115-19.
Hummel, 1999, "Large-scale applications of NAD(P)-dependent oxidoreductases: recent developments," *Trends Biotechnol*. 17(12):487-492.
Jiang et al., 2000, "Highly enantioselective reduction of achiral ketones with $NaBH_4/Me_3SiCl$ catalyzed by (S)-α,α-diphenylpyrrolidinemethanol," *Tetrahedron Letters* 41:10281-10283.
Jones et al., 1981, "Enzymes in organic syntheses. 19. Evaluation of the stereoselectivities of horse liver alcohol dehydrogenase; catalyzed oxidoreductions of hydroxy- and ketothiolanes, -thianes, and -thiepanes," *Can. J. Chem*., 59:1574-1579.
Jörnvall et al., 1995, "Short-Chain Dehydrogenase/Reductases (SDR)," *Biochemistry* 34(18):6003-6013.
Kallberg et al., 2002, "Short-chain dehydrogenase/reductase (SDR) relationships: A large family with eight clusters common to human, animal, and plant genomes," *Protein Sci*. 11(3):636-641.
Kallberg et al., 2002, "Short-chain dehydrogenases/reductases (SDRs) Coenzyme-based functional assignments in completed genomes," *Eur. J. Biochem*. 269:4409-4417.
Niefind et al., 2003, "The Crystal Structure of R-specific Alcohol Dehydrogenase from *Lactobacillus brevis* Suggests the Structural Basis of its Metal Dependency," *J Mol Bio*. 327(2):317-28.
Partial PCT International Search Report from PCT/US2008/076333 dated Feb. 18, 2009.
PCT International Search Report from PCT/US2008/076333 dated May 12, 2009.

(56) References Cited

OTHER PUBLICATIONS

PCT International Search Report from PCT/US2008/078046 dated Jan. 13, 2009.

Ramachandran et al., 2004, "Relationship between the structure and enantioselectivity in the asymmetric reduction of 2', 6'-disubstituted acetophenones with DIP-Chloride™. An ab initio study ," *Tetrahedron Letters* 45:2603-2605.

Rodrigues et al., 2004, "Recent Advances in the Biocatalytic Asymmetric Reduction of Acetophenones and α,β-Unsaturated Carbonyl Compounds," *Food Technol. Biotechnol.* 42 (4) 295-303.

Schlieben et al., 2005, "Atomic Resolution Structures of R-specific Alcohol Dehydrogenase from *Lactobacillus brevis* Provide the Structural Bases of its Substrate and Cosubstrate Specificity," *J. Mol. Biol.* 349(4):801-13.

Shimoda et al., 2006, "Diastereoselective reduction of β-keto carbonyl compounds by cultured plant cells," *Tetrahedron Lett.* 47(10):1541-1544.

Temiño et al., 2005, "Entrapment of the alcohol dehydrogenase from *Lactobacillus kefir* in polyvinyl alcohol for the synthesis of chiral hydrophobic alcohols in organic solvents," *Enzyme Microb. Technol.*, 36(1):3-9.

U.S. Appl. No. 12/243,968, filed Oct. 1, 2008.

Weckbecker et al., 2006, "Cloning, expression, and characterization of an (R)-specific alcohol dehydrogenase from *Lactobacillus kefir,*" *Biocatal. Biotransform.*, 24(5):380-389.

Xie et al., 2006, "Asymmetric Reductio n of o-Chloroacetophenone with *Candida pseudotropicalis* 104," *Biotechnol. Prog.* 22:1301-1304.

Zhou et al., 1983, "Stereochemical Control of Yeast Reductions. 1. Asymmetric Synthesis of L-Carnitine," *J. Am. Chem. Soc.*, 105:5925-5926.

Zhu et al., 2005, "Evaluation of substituent effects on activity and enantioselectivity in the enzymatic reduction of aryl ketones," *Tetrahedron Asymm.* 16:1541-1546.

Zymanczyk-Duda et al., 2004, "Stereochemical control of asymmetric hydrogen transfer employing five different kinds of fungi in anhydrous hexane," *Enzyme Microbial Technol.* 34(6):578-582.

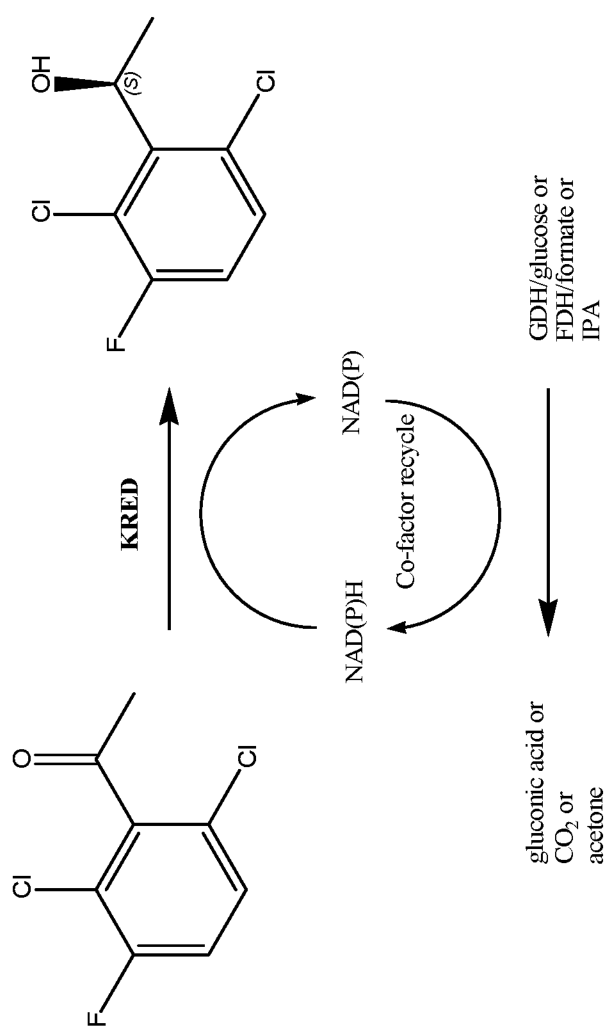
KRED
NAD(P)H
NAD(P)
Co-factor recycle
GDH/glucose or
FDH/formate or
IPA
gluconic acid or
$CO_2$ or
acetone
F
Cl
Cl
O
OH
(S)

KETOREDUCTASE POLYPEPTIDES FOR THE REDUCTION OF ACETOPHENONES

1. CROSS REFERENCES TO RELATED APPLICATIONS

This application is a Continuation of U.S. patent application Ser. No. 16/253,972, filed Jan. 22, 2019, now U.S. Pat. No. 10,927,351, which is a continuation of U.S. patent application Ser. No. 16/126,761, filed Sep. 10, 2018, now U.S. Pat. No. 10,227,572 which is a continuation of U.S. patent application Ser. No. 15/915,927, filed Mar. 8, 2018, now U.S. Pat. No. 10,100,288, which is a Continuation of U.S. patent application Ser. No. 15/840,381, filed Dec. 13, 2017, now U.S. Pat. No. 9,951,318, which is a Continuation of U.S. patent application Ser. No. 15/353,165, filed Nov. 16, 2016, now U.S. Pat. No. 9,873,863, which is a Divisional of U.S. patent application Ser. No. 14/501,416, filed Sep. 30, 2014, now U.S. Pat. No. 9,528,131, which is a Continuation of U.S. patent application Ser. No. 13/970,284, filed Aug. 19, 2013, now U.S. Pat. No. 8,852,909, which claims benefit under 35 U.S.C. § 120 to U.S. patent application Ser. No. 13/682,600, filed Nov. 20, 2012, now U.S. Pat. No. 8,512,973, which is a Divisional of U.S. patent application Ser. No. 12/210,195, filed Sep. 13, 2008, now U.S. Pat. No. 8,748,143, which claims priority under 35 U.S.C. § 119(e) to U.S. Prov. Pat. Appln. Ser. No. 60/972,058, filed Sep. 13, 2007, all of which are incorporated herein by reference in their entireties and for all purposes.

2. REFERENCE TO SEQUENCE LISTING, TABLE OR COMPUTER PROGRAM

The Sequence Listing concurrently submitted herewith under 37 C.F.R. § 1.821 in a computer readable form (CRF) via EFS-Web as file name "CX2-048USD1_ST25.txt" is herein incorporated by reference. The electronic copy of the Sequence Listing was created on Nov. 20, 2012, with a file size of 221,354 bytes. This Sequence Listing file is identical but for minor formatting correction with the electronic copy of the Sequence Listing with file name "376247-017.txt" that was created on Sep. 13, 2008, with a file size of 213 Kbytes, and which was filed with the parent application Ser. No. 12/210,195 on Sep. 13, 2008.

3. BACKGROUND

Enzymes belonging to the ketoreductase (KRED) or carbonyl reductase class (EC1.1.1.184) are useful for the synthesis of optically active alcohols from the corresponding prostereoisomeric ketone substrate and by stereospecific reduction of corresponding racemic aldehyde substrates. KREDs typically convert ketone and aldehyde substrates to the corresponding alcohol product, but may also catalyze the reverse reaction, oxidation of an alcohol substrate to the corresponding ketone/aldehyde product. The reduction of ketones and aldehydes and the oxidation of alcohols by enzymes such as KRED requires a co-factor, most commonly reduced nicotinamide adenine dinucleotide (NADH) or reduced nicotinamide adenine dinucleotide phosphate (NADPH), and nicotinamide adenine dinucleotide (NAD) or nicotinamide adenine dinucleotide phosphate (NADP) for the oxidation reaction. NADH and NADPH serve as electron donors, while NAD and NADP serve as electron acceptors. It is frequently observed that ketoreductases and alcohol dehydrogenases accept either the phosphorylated or the non-phosphorylated co-factor (in its oxidized and reduced state), but not both.

KRED enzymes can be found in a wide range of bacteria and yeasts (for reviews, see Kraus and Waldman, 1995, *Enzyme catalysis in organic synthesis*, Vols. 1&2. VCH Weinheim; Faber, K., 2000, *Biotransformations in organic chemistry*, 4th Ed. Springer, Berlin Heidelberg New York; and Hummel and Kula, 1989, *Eur. J. Biochem.* 184:1-13). Several KRED gene and enzyme sequences have been reported, e.g., *Candida magnoliae* (Genbank Acc. No. JC7338; GI:11360538) *Candida parapsilosis* (Genbank Acc. No. BAA24528.1; GI:2815409), *Sporobolomyces salmonicolor* (Genbank Acc. No. AF160799; GI:6539734).

In order to circumvent many chemical synthetic procedures for the production of key compounds, ketoreductases are being increasingly employed for the enzymatic conversion of different keto and aldehyde substrates to chiral alcohol products. These applications can employ whole cells expressing the ketoreductase for biocatalytic ketone and aldehyde reductions, or by use of purified enzymes in those instances where presence of multiple ketoreductases in whole cells would adversely affect the stereopurity and yield of the desired product. For in vitro applications, a co-factor (NADH or NADPH) regenerating enzyme such as glucose dehydrogenase (GDH), formate dehydrogenase etc. is used in conjunction with the ketoreductase. Examples using ketoreductases to generate useful chemical compounds include asymmetric reduction of 4-chloroacetoacetate esters (Zhou, 1983, *J. Am. Chem. Soc.* 105:5925-5926; Santaniello, *J. Chem. Res.* (S) 1984:132-133; U.S. Pat. Nos. 5,559,030; 5,700,670 and 5,891,685), reduction of dioxocarboxylic acids (e.g., U.S. Pat. No. 6,399,339), reduction of tert-butyl (S) chloro-5-hydroxy-3-oxohexanoate (e.g., U.S. Pat. No. 6,645,746 and WO 01/40450), reduction pyrrolotriazine-based compounds (e.g., U.S. application No. 2006/0286646); reduction of substituted acetophenones (e.g., U.S. Pat. No. 6,800,477); and reduction of ketothiolanes (WO 2005/054491).

It is desirable to identify other ketoreductase enzymes that can be used to carryout conversion of various keto substrates to its corresponding chiral alcohol products.

4. SUMMARY

The present disclosure provides engineered ketoreductase ("KRED") enzymes that are capable of stereoselectively reducing a defined keto substrate to its corresponding alcohol product and having an improved property when compared with the naturally-occurring, wild-type KRED enzyme obtained from *L. kefir* (SEQ ID NO:4) or *L. brevis* (SEQ ID NO:2) or *L. minor* (SEQ ID NO:98) or when compared with other engineered ketoreductase enzymes. It is shown in the present disclosure that naturally occurring ketoreductases from *Lactobacillus* species reduce the compound acetophenone to (R)-1-phenethanol. Since the wild-type enzymes are generally selective for reducing the acetophenone to their corresponding (R)-alcohols, these naturally occurring enzymes are (R)-selective ketoreductases, or (R)-ketoreductases. For substituted acetophenones, such as 2',6'-dichloro-3'-fluoroacetophenone, these wild-type *L. kefir* or *L. brevis* or *L. minor* ketoreductase enzymes display insignificant, if any, activity towards the substituted acetophenone substrate. However, the engineered ketoreductase enzymes of the present disclosure, which are derived from a wild-type *Lactobacillus* species ketoreductase, are capable of reducing acetophenone to (S)-1-phenethanol. Hence, the ketoreductases described herein are characterized by reversed enantioselectivity as compared to the wild-type *L. kefir* or *L. brevis* or *L. minor* ketoreductases for the reduction of acetophenone. These polypeptides of the disclosure are consequently referred to as (S)-selective ketoreductases, or (S)-ketoreductases. The reversed enantioselectivity is based on mutating the residue at position 190 (i.e., X190) of the wild type ketoreductase enzyme to a residue which is not tyrosine, preferably to a non-aromatic residue, and particularly to a proline residue.

Moreover, the engineered enzymes described herein can have one or more improved properties in addition to the altered stereoselectivity. For example, the engineered ketoreductase polypeptide can have increased enzymatic activity as compared to the wild-type ketoreductase enzyme for reducing the substrate to the product and/or further increases stereoselectivity for the (S) enantiomer. Improvements in enzyme properties can also include, among others, increases in thermostability, solvent stability, or reduced product inhibition. As further disclosed herein, while the wildtype ketoreductases show insignificant activity in reducing substituted acetophenones, the disclosure provides ketoreductases of capable of reducing or converting a substituted acetophenone, 2',6'-dichloro-3'-fluoroacetophenone to (S)-1-[2,6-dichloro-3-fluorophenyl]-ethanol.

Accordingly, in some embodiments, the present disclosure relates to ketoreductase polypeptides having at the residue corresponding to X190 of SEQ ID NO:2, 4 or 98 a residue which is not a tyrosine. In some embodiments, this residue is a non-aromatic residue, such as, for example, an aliphatic, constrained, non-polar, or cysteine residue. In some embodiments, this residue is proline.

In addition to the features at the residue corresponding to X190, the ketoreductases can have one or more residue differences at other residue positions as compared to the sequences of SEQ ID NO:2, 4, or 98. In some embodiments, the ketoreductase polypeptides herein comprise an amino acid sequence that is at least about 85%, 86%, 87%, 88%, 89%, 90%, 91%, 92%, 93%, 94%, 95%, 96%, 97%, 98%, 99% or more identical as compared to a reference sequence based on SEQ ID NO: 2, 4 or 98 having at the residue corresponding to X190 a non-aromatic residue, including an aliphatic, constrained, non-polar, or cysteine residue, particularly alanine, isoleucine, cysteine, or proline, with the proviso that the ketoreductase polypeptide has at the residue corresponding to X190 a residue which is other than a tyrosine, particularly a non-aromatic residue. In some embodiments, the ketoreductase polypeptide has an amino acid sequence in which the residue corresponding to X190 is an aliphatic, constrained, non-polar, or cysteine residue. In some embodiments, the ketoreductase polypeptide has an amino acid sequence in which the residue corresponding to X190 is alanine, isoleucine, cysteine, or proline, particularly proline. In some embodiments, these residue differences results in an improved property, such as increased enzymatic activity for the substrate. The improved properties can be in reference to the wildtype ketoreductase enzyme or in reference to an engineered ketoreductase enzyme. For example, in some embodiments, improvements in the ketoreductase enzymes are compared to the properties of the engineered enzyme having the amino acid sequence corresponding to SEQ ID NO:6, which is capable of converting the substrate to the product with a stereomeric excess greater than 99% with measurable activity, and therefore improved as compared to the wild-type *L. kefir* or *L. brevis* or *L. minor* ketoreductases. Various residue differences that can result in one or more improved enzyme properties are provided in the detailed description. In some embodiments, these engineered ketoreductase polypeptides are based on the sequence formulas as laid out in SEQ ID NO:95, 96 and 119 (or a region thereof, such as residues 90-211).

In some embodiments, the ketoreductase polypeptide of the disclosure are capable of converting 2',6'-dichloro-3'-fluoroacetophenone to (S)-1-[2,6-dichloro-3-fluorophenyl]-ethanol with a stereomeric excess greater than 99% and at a rate that is improved over the ketoreductase polypeptide having the sequence of SEQ ID NO:6. Exemplary polypeptides that are improved over SEQ ID NO:6 with respect to enzymatic activity, include but are not limited to, polypeptides comprising amino acid sequences corresponding to SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, and 94.

In some embodiments, the ketoreductase polypeptides are capable of converting 2',6'-dichloro-3'-fluoroacetophenone to (S)-1-[2,6-dichloro-3-fluorophenyl]-ethanol with a stereomeric excess greater than 99% and at a rate that is improved over the ketoreductase polypeptide having the sequence of SEQ ID NO:6, wherein the polypeptide also has improved thermostability as compared to the polypeptide having the sequence of SEQ ID NO:6. Exemplary polypeptides having such improvements include, but are not limited to, polypeptides comprising amino acid sequences corresponding to SEQ ID NO: 8, 16, 18, 20, 22, 26, 28, 30, 32, 34, 38, 40, 42, 44, 46, 54, 66, 68, 70, 72, 74, 76, 78, 80, 82, 84, 86, 88, 90, 92, and 94.

In some embodiments, the ketoreductase polypeptides are capable of converting 2',6'-dichloro-3'-fluoroacetophenone to (S)-1-[2,6-dichloro-3-fluorophenyl]-ethanol with a stereomeric excess greater than 99% and at a rate that is at least about 450% greater than the ketoreductase polypeptide having the sequence of SEQ ID NO:6. Exemplary polypeptides capable of such an improvement include, but are not limited to, polypeptides comprising amino acid sequences corresponding to SEQ ID NO: 8, 10, 14, 16, 18, 22, 24, 26, 28, 30, 32, 34, 36, 38, 40, 42, 44, 46, 54, 56, 58, 60, 62, 64, 66, 68, 70, 72, 74, 76, 78, 80, 82, 84, 86, 88, 90, 92, and 94.

In some embodiments, the ketoreductase polypeptides are capable of converting 2',6'-dichloro-3'-fluoroacetophenone to (S)-1-[2,6-dichloro-3-fluorophenyl]-ethanol with a stereomeric excess greater than 99% and at a rate that is at least about 450% greater than the ketoreductase polypeptide having the sequence of SEQ ID NO:6, wherein the polypeptide also has an improved thermostability as compared to the polypeptide of SEQ ID NO:6. Exemplary polypeptides having such properties include, but are not limited to, polypeptides comprising amino acid sequences corresponding to SEQ ID NO: 8, 16, 18, 22, 26, 28, 30, 32, 34, 38, 40, 42, 44, 46, 54, 66, 68, 70, 72, 74, 76, 78, 80, 82, 84, 86, 88, 90, 92, and 94.

In some embodiments, the ketoreductase polypeptides are capable of converting 2',6'-dichloro-3'-fluoroacetophenone to (S)-1-[2,6-dichloro-3-fluorophenyl]-ethanol with a stereomeric excess greater than 99% and at a rate that is at least about 1500% greater than the ketoreductase polypeptide having the sequence of SEQ ID NO:6. Exemplary polypeptides capable of such an improvement include, but are not limited to, polypeptides comprising amino acid sequences corresponding to SEQ ID NO: 18, 32, 34, 36, 38, 40, 42, 44, 46, 74, 76, 78, 80, 82, 84, 86, 88, 90, 92, and 94.

In some embodiments, the ketoreductase polypeptide are capable of converting 2',6'-dichloro-3'-fluoroacetophenone to (S)-1-[2,6-dichloro-3-fluorophenyl]-ethanol with a stereomeric excess greater than 99% and at a rate that is at least about 1500% greater than the ketoreductase polypeptide having the sequence of SEQ ID NO:6, wherein the polypeptide also has an improved thermostability as compared to the polypeptide of SEQ ID NO:6. Exemplary polypeptides having such properties include, but are not limited to, polypeptides comprising amino acid sequences corresponding to SEQ ID NO: 18, 32, 34, 36, 38, 40, 42, 44, 46, 74, 76, 78, 80, 82, 84, 86, 88, 90, 92, and 94.

In some embodiments, the ketoreductase polypeptide are capable of converting in less than about 24 hours at least about 95% of the 2',6'-dichloro-3'-fluoroacetophenone substrate to (S)-1-(2,6-dichloro-3-fluorophenyl) ethanol, in at least about 99% stereomeric excess, when carried out with the polypeptide at an amount of less than about 1% by weight with respect to the amount of the 2',6'-dichloro-3'-fluoroacetophenone substrate. Exemplary polypeptides that have this capability include, but are not limited to, polypeptides comprising amino acid sequences corresponding to 18, 32, 34, 36, 38, 40, 42, 44, 46, 74, 76, 78, 80, 82, 84, 86, 88, 90, 92, and 94.

In some embodiments, the ketoreductase polypeptides are capable of converting 2',6'-dichloro-3'-fluoroacetophenone to (S)-1-[2,6-dichloro-3-fluorophenyl]-ethanol with an stereomeric excess greater than 99% and at a rate that is at least about 450% greater than the ketoreductase polypeptide having the sequence of SEQ ID NO:6, wherein the polypeptide is also capable, after a heat treatment of 50° C. for 2 hours, of converting the substrate to the product at a rate that is at least about 400% greater than the polypeptide having the sequence of SEQ ID NO:16 (where the polypeptide of SEQ ID NO:16 was also treated with the same heat treatment). Exemplary polypeptides having such properties include, but are not limited to, polypeptides comprising amino acid sequences corresponding to SEQ ID NO: 18, 32, 34, 36, 38, 40, 42, 44, 46, 74, 76, 78, 80, 82, 84, 86, 88, 90, 92, and 94.

In some embodiments, the improved ketoreductase polypeptides capable of converting 2',6'-dichloro-3'-fluoroacetophenone to (S)-1-[2,6-dichloro-3-fluorophenyl]-ethanol comprise a region or domain having an amino acid sequence that is at least about 85%, 86%, 87%, 88%, 89%, 90%, 91%, 92%, 93%, 94%, 95%, 96%, 97%, 98%, or 99% identical to a region or domain corresponding to residues 90-211 of a reference sequence based on SEQ ID NO:2, 4 or 98 having at the residue corresponding to X190 a non-aromatic residue, including an aliphatic, constrained, non-polar, or cysteine residue, particularly alanine, isoleucine, cysteine, or proline, with the proviso that the ketoreductase polypeptide region or domain has at the residue corresponding to X190 a residue other than a tyrosine. In some embodiments, the ketoreductase polypeptide has a region or domain corresponding to residues 90-211 of the reference sequence in which the residue corresponding to X190 is a non-aromatic residue. In some embodiments, this residue corresponding to X190 can be an aliphatic, constrained, non-polar, or cysteine residue. In some embodiments, the residue corresponding to X190 can be alanine, isoleucine, cysteine, or proline, particularly proline. In some embodiments, the ketoreductase polypeptides can have one or more residue differences in the domain or region as compared to the reference sequence. Various residue positions that can differ from the reference sequence are provided in the detailed description.

In another aspect, the present disclosure provides polynucleotides encoding the engineered ketoreductases described herein or polynucleotides that hybridize to such polynucleotides under highly stringent conditions. The polynucleotide can include promoters and other regulatory elements useful for expression of the encoded engineered ketoreductase, and can utilize codons optimized for specific desired expression systems. Exemplary polynucleotides encoding the engineered ketoreductases include, but are not limited to, polynucleotides comprising sequences corresponding to SEQ ID NO: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, and 93.

In another aspect, the present disclosure provides host cells comprising the polynucleotides and/or expression vectors described herein. The host cells may be *L. kefir* or *L. brevis*, or they may be a different organism. The host cells can be used for the expression and isolation of the engineered ketoreductase enzymes described herein, or, alternatively, they can be used directly for the conversion of substituted acetophenone substrates of formula (I) or (III) to the corresponding (S)-alcohol product of formula (II) or (IV), respectively.

Whether carrying out the method with whole cells, cell extracts or purified ketoreductase enzymes, a single ketoreductase enzyme may be used or, alternatively, mixtures of two or more ketoreductase enzymes may be used.

As noted above, the ketoreductase enzymes described herein are capable of catalyzing the reduction reaction of a 2',6'-substituted acetophenone, which can be optionally substituted at one or more of the 3',4', and 5' positions, to the corresponding (S)-alcohol product.

In some embodiments, the ketoreductase enzymes are capable of reducing or converting the ketone of structural formula (I), 2',6'-dichloro-3'-fluoroacetophenone:

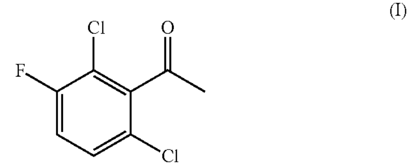

(I)

to the corresponding chiral alcohol product of structural formula (II), (S)-1-[2,6-dichloro-3-fluorophenyl]-ethanol:

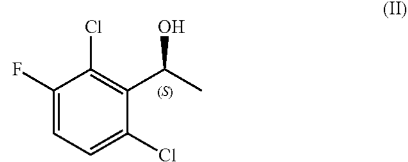

(II)

In some embodiments, the ketoreductase enzymes described herein are capable of catalyzing the reduction of 2',6'-substituted acetophenone compounds of structural formula (III):

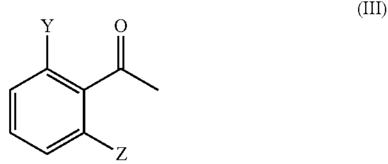

(III)

optionally substituted at one or more of the 3', 4', and 5' positions, wherein Y and Z are independently selected from $CH_3$, $CF_3$, $NH_2$, OH, $OCH_3$, Cl, and Br, to the corresponding chiral alcohol product of structural formula (IV):

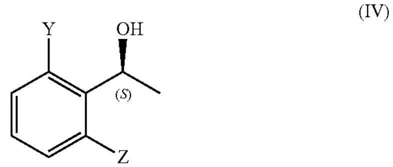

(IV)

Accordingly, in some embodiments, the disclosure provides a method for reducing a 2', 6' substituted acetophenone substrate, optionally substituted at one or more of the 3', 4' and 5' positions, to the corresponding substituted (S)-phenethanol, where the method comprises contacting the substrate with the ketoreductases described herein under reaction conditions suitable for reducing or converting the substrate to the corresponding substituted (S)-phenethanol. In some embodiments of this method, the substrate is reduced to the product in greater than about 25%, 50%, 75%, 80%, 85%, 90%, 95%, 99%, or 99.9% stereomeric excess.

In some embodiments, the disclosure provides a method for reducing a 2', 6' substituted acetophenone of formula (III) to the corresponding substituted (S)-phenethanol of formula (IV), where the method comprises contacting the substrate with the ketoreductases described herein under reaction conditions suitable for reducing or converting the substrate of formula (III) to the corresponding substituted (S)-phenethanol product of formula (IV). In some embodiments of this method, the substrate is reduced to the product in greater than about 25%, 50%, 75%, 80%, 85%, 90%, 95%, 99%, or 99.9% stereomeric excess.

In some embodiments, the disclosure provides a method for reducing a 2',6'-dichloro-3'-fluoroacetophenone substrate of formula (I) to its corresponding (S)-alcohol product of formula (II), (S)-1-[2,6-dichloro-3-fluorophenyl]-ethanol, where the method comprises contacting or incubating the 2',6'-dichloro-3'-fluoroacetophenone with the ketoreductases described herein under reaction conditions suitable for reducing or converting 2',6'-dichloro-3'-fluoroacetophenone to (S)-1-[2,6-dichloro-3-fluorophenyl]-ethanol. In some embodiments of this method, the substrate is reduced to the product in greater than about 85%, 90%, 95%, 99%, or 99.9% stereomeric excess. In some embodiments, the substrate is reduced to the product in greater than about 85% stereomeric excess, wherein the ketoreductase polypeptide comprises an amino acid sequence based on the sequence formula of SEQ ID NO:95, 96 or 119. In some embodiments, the substrate is reduced to the product in greater than about 99% stereomeric excess, wherein the ketoreductase polypeptides used in the method comprise amino acid sequences corresponding to SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, and 94.

In some embodiment of this method, at least about 95% of the substrate is reduced to the product in greater than about 99% stereomeric excess in less than 24 hours when the method is carried out with the ketoreductase polypeptide at an amount of less than about 1% by weight with respect to the amount of the 2',6'-dichloro-3'-fluoroacetophenone substrate, wherein the ketoreductase polypeptides comprise amino acid sequences that corresponds to SEQ ID NO: 18, 32, 34, 36, 38, 40, 42, 44, 46, 74, 76, 78, 80, 82, 84, 86, 88, 90, 92, and 94.

In some embodiments, the disclosure provides compositions of a ketoreductases described herein and a 2,6 substituted acetophenone, optionally substituted at one or more of 3',4' or 5' positions, and/or the corresponding substituted (S)-phenethanol. In some embodiments, the compositions comprise a ketoreductase described herein and the compound of formula (I) and/or the compound of formula (II). In some embodiments, the compositions comprise a ketoreductase described herein and the compound of formula (III), and/or the compound of formula (IV). In some embodiments, the compositions comprise a ketoreductase described herein, and the compound of formula (V) and/or the compound of formula (VI). In some embodiments, the compositions can further comprise a cofactor regenerating system.

In some embodiments, the disclosure relates to use of the engineered ketoreductases in the synthesis of protein kinase inhibitors described in WO06021886, WO06021884, WO06021881, and WO04076412. In some embodiments, in a method for synthesis of these protein kinase inhibitors, a step in the method can comprise reducing or converting the substrate 2',6'-dichloro-3'-fluoroacetophenone of formula (I) to its corresponding (S)-alcohol product of formula (II), (S)-1-[2,6-dichloro-3-fluorophenyl]-ethanol with the ketoreductases of the disclosure.

5. BRIEF DESCRIPTION OF THE FIGURES

FIG. 1 illustrates the role of ketoreductases (KRED) in the conversion of the substrate compound of formula (I), 2',6'-dichloro-3-fluoroacetophenone, to the corresponding chiral alcohol product of formula (II), (S)-1-[2,6,-dichloro-3-fluorophenyl]-ethanol. In this reaction, the substrate is reduced biocatalytically to the corresponding (S)-alcohol. This reduction uses a KRED described herein and a co-factor such as NADPH. A glucose dehydrogenase (GDH) is used to covert/recycle NADP to NADPH. Glucose is converted to gluconic acid, which in turn is converted to its sodium salt (sodium gluconate) with the addition of sodium hydroxide.

6. DETAILED DESCRIPTION

6.1 Definitions

As used herein, the following terms are intended to have the following meanings.

"Ketoreductase" and "KRED" are used interchangeably herein to refer to a polypeptide having an enzymatic capability of reducing a carbonyl group to its corresponding alcohol. More specifically, the ketoreductase polypeptides of the invention are capable of stereoselectively reducing the compound of formula (I), supra to the corresponding product of formula (II), supra. The polypeptide typically utilizes a cofactor reduced nicotinamide adenine dinucleotide (NADH) or reduced nicotinamide adenine dinucleotide phosphate (NADPH) as the reducing agent. Ketoreductases as used herein include naturally occurring (wild type) ketoreductases as well as non-naturally occurring engineered polypeptides generated by human manipulation.

"Coding sequence" refers to that portion of a nucleic acid (e.g., a gene) that encodes an amino acid sequence of a protein.

"Naturally-occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

"Recombinant" when used with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, 1981, *Adv. Appl. Math.* 2:482, by the homology alignment algorithm of Needleman and Wunsch, 1970, *J. Mol. Biol.* 48:443, by the search for similarity method of Pearson and Lipman, 1988, *Proc. Natl. Acad. Sci. USA* 85:2444, by computerized implementations of these algorithms (GAP, BESTFIT, FASTA, and TFASTA in the GCG Wisconsin Software Package), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al., 1990, *J. Mol. Biol.* 215: 403-410 and Altschul et al., 1977, *Nucleic Acids Res.* 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, *Proc Natl Acad Sci USA* 89:10915). Exemplary determination of sequence alignment and % sequence identity can employ the BESTFIT or GAP programs in the GCG Wisconsin Software package (Accelrys, Madison Wis.), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a "comparison window" to identify and compare local regions of sequence similarity.

In some embodiments, a "reference sequence" can be based on a primary amino acid sequence, where the reference sequence is a sequence that can have one or more changes in the primary sequence. For instance, a reference sequence "based on SEQ ID NO:4 having at the residue corresponding to X190 a proline" refers to a reference sequence in which the corresponding residue at X190 in SEQ ID NO:4 has been changed to a proline.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Substantial identity" refers to a polynucleotide or polypeptide sequence that has at least 80 percent sequence identity, at least 85 percent identity and 89 to 95 percent sequence identity, more usually at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term “substantial identity” means that two polypeptide sequences, when optimally aligned, such as by the programs GAP or BESTFIT using default gap weights, share at least 80 percent sequence identity, preferably at least 89 percent sequence identity, at least 95 percent sequence identity or more (e.g., 99 percent sequence identity). Preferably, residue positions which are not identical differ by conservative amino acid substitutions.

“Corresponding to”, “reference to” or “relative to” when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered ketoreductase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

“Stereoselectivity” refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (e.e.) calculated therefrom according to the formula [major enantiomer−minor enantiomer]/[major enantiomer+minor enantiomer]. This can also be referred to as stereomeric excess (s.e). Where the stereoisomers are diastereoisomers, the stereoselectivity is referred to as diastereoselectivity, the fraction (typically reported as a percentage) of one diastereomer in a mixture of two diastereomers.

“Highly stereoselective” refers to a ketoreductase polypeptide that is capable of converting or reducing 2',6'-dichloro-3'-fluoroacetophenone (formula (I)) to the corresponding (S)-alcohol product (S)-1-[2,6-dichloro-3-fluorophenyl]-ethanol (formula (II)) with at least about 85% stereomeric excess.

“Improved enzyme property” refers to a ketoreductase polypeptide that exhibits an improvement in any enzyme property as compared to a reference ketoreductase. For the engineered ketoreductase polypeptides described herein, the comparison is generally made to the wild-type ketoreductase enzyme, although in some embodiments, the reference ketoreductase can be another improved engineered ketoreductase. Enzyme properties for which improvement is desirable include, but are not limited to, enzymatic activity (which can be expressed in terms of percent conversion of the substrate), thermal stability, pH activity profile, cofactor requirements, refractoriness to inhibitors (e.g., product inhibition), stereospecificity, and stereoselectivity (including stereoselectivity).

“Increased enzymatic activity” refers to an improved property of the engineered ketoreductase polypeptides, which can be represented by an increase in specific activity (e.g., product produced/time/weight protein) or an increase in percent conversion of the substrate to the product (e.g., percent conversion of starting amount of substrate to product in a specified time period using a specified amount of KRED) as compared to the reference ketoreductase enzyme. Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. Improvements in enzyme activity can be from about 1.5 times the enzymatic activity of the corresponding wild-type ketoreductase enzyme, to as much as 2 times. 5 times, 10 times, 20 times, 25 times, 50 times, 75 times, 100 times, or more enzymatic activity than the naturally occurring ketoreductase or another engineered ketoreductase from which the ketoreductase polypeptides were derived. In specific embodiments, the engineered ketoreductase enzyme exhibits improved enzymatic activity in the range of 1.5 to 50 times, 1.5 to 100 times greater than that of the parent ketoreductase enzyme. It is understood by the skilled artisan that the activity of any enzyme is diffusion limited such that the catalytic turnover rate cannot exceed the diffusion rate of the substrate, including any required cofactors. The theoretical maximum of the diffusion limit, or $k_{cat}/K_m$, is generally about $10^8$ to $10^9$ ($M^{-1}$ $s^{-1}$). Hence, any improvements in the enzyme activity of the ketoreductase will have an upper limit related to the diffusion rate of the substrates acted on by the ketoreductase enzyme. Ketoreductase activity can be measured by any one of standard assays used for measuring ketoreductase, such as a decrease in absorbance or fluorescence of NADPH (see Example 5) due to its oxidation with the concomitant reduction of a ketone to an alcohol, or by product produced in a coupled assay. Comparisons of enzyme activities are made using a defined preparation of enzyme, a defined assay under a set condition, and one or more defined substrates, as further described in detail herein. Generally, when lysates are compared, the numbers of cells and the amount of protein assayed are determined as well as use of identical expression systems and identical host cells to minimize variations in amount of enzyme produced by the host cells and present in the lysates.

“Conversion” refers to the enzymatic reduction of the substrate to the corresponding product. “Percent conversion” refers to the percent of the substrate that is reduced to the product within a period of time under specified conditions. Thus, the “enzymatic activity” or “activity” of a ketoreductase polypeptide can be expressed as “percent conversion” of the substrate to the product.

“Thermostable” refers to a ketoreductase polypeptide that maintains similar activity (more than 60% to 80% for example) after exposure to elevated temperatures (e.g., 40-80° C.) for a period of time (e.g., 0.5-24 hrs) compared to the untreated enzyme.

“Solvent stable” refers to a ketoreductase polypeptide that maintains similar activity (more than e.g., 60% to 80%) after exposure to varying concentrations (e.g., 5-99%) of solvent (isopropyl alcohol, tetrahydrofuran, 2-methyltetrahydrofuran, acetone, toluene, butylacetate, methyl tert-butylether, etc.) for a period of time (e.g., 0.5-24 hrs) compared to the untreated enzyme.

“pH stable” refers to a ketoreductase polypeptide that maintains similar activity (more than e.g., 60% to 80%) after exposure to high or low pH (e.g., 4.5-6 or 8 to 12) for a period of time (e.g., 0.5-24 hrs) compared to the untreated enzyme.

"Thermo- and solvent stable" refers to a ketoreductase polypeptide that are both thermostable and solvent stable.

"Derived from" as used herein in the context of engineered ketoreductase enzymes, identifies the originating ketoreductase enzyme, and/or the gene encoding such ketoreductase enzyme, upon which the engineering was based. For example, the engineered ketoreductase enzyme of SEQ ID NO: 38 was obtained by artificially evolving, over multiple generations the gene encoding the *Lactobacillus kefir* ketoreductase enzyme of SEQ ID NO:4. Thus, this engineered ketoreductase enzyme is "derived from" the wild-type ketoreductase of SEQ ID NO: 4.

"Hydrophilic amino acid or residue" refers to an amino acid or residue having a side chain exhibiting a hydrophobicity of less than zero according to the normalized consensus hydrophobicity scale of Eisenberg et al., 1984*, J. Mol. Biol.* 179:125-142. Genetically encoded hydrophilic amino acids include L-Thr (T), L-Ser (S), L-His (H), L-Glu (E), L-Asn (N), L-Gln (Q), L-Asp (D), L-Lys (K) and L-Arg (R).

"Acidic amino acid or residue" refers to a hydrophilic amino acid or residue having a side chain exhibiting a pK value of less than about 6 when the amino acid is included in a peptide or polypeptide. Acidic amino acids typically have negatively charged side chains at physiological pH due to loss of a hydrogen ion. Genetically encoded acidic amino acids include L-Glu (E) and L-Asp (D).

"Basic amino acid or residue" refers to a hydrophilic amino acid or residue having a side chain exhibiting a pK value of greater than about 6 when the amino acid is included in a peptide or polypeptide. Basic amino acids typically have positively charged side chains at physiological pH due to association with hydronium ion. Genetically encoded basic amino acids include L-Arg (R) and L-Lys (K).

"Polar amino acid or residue" refers to a hydrophilic amino acid or residue having a side chain that is uncharged at physiological pH, but which has at least one bond in which the pair of electrons shared in common by two atoms is held more closely by one of the atoms. Genetically encoded polar amino acids include L-Asn (N), L-Gln (Q), L-Ser (S) and L-Thr (T).

"Hydrophobic amino acid or residue" refers to an amino acid or residue having a side chain exhibiting a hydrophobicity of greater than zero according to the normalized consensus hydrophobicity scale of Eisenberg et al., 1984*, J. Mol. Biol.* 179:125-142. Genetically encoded hydrophobic amino acids include L-Pro (P), L-Ile (I), L-Phe (F), L-Val (V), L-Leu (L), L-Trp (W), L-Met (M), L-Ala (A) and L-Tyr (Y).

"Aromatic amino acid or residue" refers to a hydrophilic or hydrophobic amino acid or residue having a side chain that includes at least one aromatic or heteroaromatic ring. Genetically encoded aromatic amino acids include L-Phe (F), L-Tyr (Y) and L-Trp (W). Although owing to the pKa of its heteroaromatic nitrogen atom L-His (H) it is sometimes classified as a basic residue, or as an aromatic residue as its side chain includes a heteroaromatic ring, herein histidine is classified as a hydrophilic residue or as a "constrained residue" (see below).

"Constrained amino acid or residue" refers to an amino acid or residue that has a constrained geometry. Herein, constrained residues include L-pro (P) and L-his (H). Histidine has a constrained geometry because it has a relatively small imidazole ring. Proline has a constrained geometry because it also has a five membered ring.

"Non-polar amino acid or residue" refers to a hydrophobic amino acid or residue having a side chain that is uncharged at physiological pH and which has bonds in which the pair of electrons shared in common by two atoms is generally held equally by each of the two atoms (i.e., the side chain is not polar). Genetically encoded non-polar amino acids include L-Gly (G), L-Leu (L), L-Val (V), L-Ile (I), L-Met (M) and L-Ala (A).

"Aliphatic amino acid or residue" refers to a hydrophobic amino acid or residue having an aliphatic hydrocarbon side chain. Genetically encoded aliphatic amino acids include L-Ala (A), L-Val (V), L-Leu (L) and L-Ile (I).

"Cysteine" The amino acid L-Cys (C) is unusual in that it can form disulfide bridges with other L-Cys (C) amino acids or other sulfanyl- or sulfhydryl-containing amino acids. The "cysteine-like residues" include cysteine and other amino acids that contain sulfhydryl moieties that are available for formation of disulfide bridges. The ability of L-Cys (C) (and other amino acids with —SH containing side chains) to exist in a peptide in either the reduced free —SH or oxidized disulfide-bridged form affects whether L-Cys (C) contributes net hydrophobic or hydrophilic character to a peptide. While L-Cys (C) exhibits a hydrophobicity of 0.29 according to the normalized consensus scale of Eisenberg (Eisenberg et al., 1984, supra), it is to be understood that for purposes of the present disclosure L-Cys (C) is categorized into its own unique group.

"Small amino acid or residue" refers to an amino acid or residue having a side chain that is composed of a total three or fewer carbon and/or heteroatoms (excluding the α-carbon and hydrogens). The small amino acids or residues may be further categorized as aliphatic, non-polar, polar or acidic small amino acids or residues, in accordance with the above definitions. Genetically-encoded small amino acids include L-Ala (A), L-Val (V), L-Cys (C), L-Asn (N), L-Ser (S), L-Thr (T) and L-Asp (D).

"Hydroxyl-containing amino acid or residue" refers to an amino acid containing a hydroxyl (—OH) moiety. Genetically-encoded hydroxyl-containing amino acids include L-Ser (S) L-Thr (T) and L-Tyr (Y).

"Conservative" amino acid substitutions or mutations refer to the interchangeability of residues having similar side chains, and thus typically involves substitution of the amino acid in the polypeptide with amino acids within the same or similar defined class of amino acids. In some embodiments, conservative mutations as used herein do not include substitutions from a hydrophilic to hydrophilic, hydrophobic to hydrophobic, hydroxyl-containing to hydroxyl-containing, or small to small residue, if the conservative mutation can instead be a substitution from an aliphatic to an aliphatic, non-polar to non-polar, polar to polar, acidic to acidic, basic to basic, aromatic to aromatic, or constrained to constrained residue. Further, as used herein, A, V, L, or I can be conservatively mutated to either another aliphatic residue or to another non-polar residue. Table 1 below shows exemplary conservative substitutions.

TABLE 1

| Conservative Substitutions | |
|---|---|
| Residue | Possible Conservative Mutations |
| A, L, V, I | Other aliphatic (A, L, V, I)<br>Other non-polar (A, L, V, I, G, M) |
| G, M | Other non-polar (A, L, V, I, G, M) |
| D, E | Other acidic (D, E) |
| K, R | Other basic (K, R) |

TABLE 1-continued

| Conservative Substitutions | |
|---|---|
| Residue | Possible Conservative Mutations |
| P, H | Other constrained (P, H) |
| N, Q, S, T | Other polar |
| Y, W, F | Other aromatic (Y, W, F) |
| C | None |

"Non-conservative substitution" refers to substitution or mutation of an amino acid in the polypeptide with an amino acid with significantly differing side chain properties. Non-conservative substitutions may use amino acids between, rather than within, the defined groups listed above. In one embodiment, a non-conservative mutation affects (a) the structure of the peptide backbone in the area of the substitution (e.g., proline for glycine) (b) the charge or hydrophobicity, or (c) the bulk of the side chain.

"Deletion" refers to modification to the polypeptide by removal of one or more amino acids from the reference polypeptide. Deletions in an amino acid sequence can comprise removal of 1 or more amino acids, 2 or more amino acids, 3 or more amino acids, 4 or more amino acid, 5 or more amino acids, 6 or more amino acids, 8 or more amino acids, 10 or more amino acids, 15 or more amino acids, or 20 or more amino acids, up to 10% of the total number of amino acids, up to 15% of the total number of amino acids, or up to 20% of the total number of amino acids making up the reference enzyme while retaining enzymatic activity and/or retaining the improved properties of an engineered ketoreductase enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids from the reference polypeptide. In some embodiments, the improved engineered ketoreductase enzymes comprise insertions of one or more amino acids to the naturally occurring ketoreductase polypeptide as well as insertions of one or more amino acids to other improved ketoreductase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

"Fragment" as used herein refers to a polypeptide that has an amino-terminal and/or carboxy-terminal deletion, but where the remaining amino acid sequence is identical to the corresponding positions in the sequence. Fragments can be at least 14 amino acids long, at least 20 amino acids long, at least 50 amino acids long or longer, and up to 70%, 80%, 90%, 95%, 98%, and 99% of the full-length naturally-occurring ketoreductase polypeptide of SEQ ID NO:2 or SEQ ID NO:4.

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The improved ketoreductase enzymes may be present within a cell, present in the cellular medium, or prepared in various forms, such as lysates or isolated preparations. As such, in some embodiments, the improved ketoreductase enzyme can be an isolated polypeptide.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure ketoreductase composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated improved ketoreductases polypeptide is a substantially pure polypeptide composition.

"Stringent hybridization" is used herein to refer to conditions under which nucleic acid hybrids are stable. As known to those of skill in the art, the stability of hybrids is reflected in the melting temperature ($T_m$) of the hybrids. In general, the stability of a hybrid is a function of ion strength, temperature, G/C content, and the presence of chaotropic agents. The $T_m$ values for polynucleotides can be calculated using known methods for predicting melting temperatures (see, e.g., Baldino et al., *Methods Enzymology* 168:761-777; Bolton et al., 1962, *Proc. Natl. Acad. Sci. USA* 48:1390; Bresslauer et al., 1986, *Proc. Natl. Acad. Sci USA* 83:8893-8897; Freier et al., 1986, *Proc. Natl. Acad. Sci USA* 83:9373-9377; Kierzek et al., *Biochemistry* 25:7840-7846; Rychlik et al., 1990, *Nucleic Acids Res* 18:6409-6412 (erratum, 1991, *Nucleic Acids Res* 19:698); Sambrook et al., supra); Suggs et al., 1981, In *Developmental Biology Using Purified Genes* (Brown et al., eds.), pp. 683-693, Academic Press; and Wetmur, 1991, *Crit Rev Biochem Mol Biol* 26:227-259. All publications incorporate herein by reference). In some embodiments, the polynucleotide encodes the polypeptide disclosed herein and hybridizes under defined conditions, such as moderately stringent or highly stringent conditions, to the complement of a sequence encoding an engineered ketoreductase enzyme of the present disclosure.

"Hybridization stringency" relates to hybridization conditions, such as washing conditions, in the hybridization of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA, with greater than about 90% identity to target-polynucleotide. Exemplary moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature $T_m$ as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5×Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w:v) SDS at 65° C. and washing in 0.1×SSC containing 0.1% SDS at 65° C. Other high stringency hybridization conditions, as well as moderately stringent conditions, are described in the references cited above.

"Heterologous" polynucleotide refers to any polynucleotide that is introduced into a host cell by laboratory techniques, and includes polynucleotides that are removed from a host cell, subjected to laboratory manipulation, and then reintroduced into a host cell.

"Codon optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the ketoreductases enzymes may be codon optimized for optimal production from the host organism selected for expression.

"Preferred, optimal, high codon usage bias codons" refers interchangeably to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariant analysis, for example, using cluster analysis or correspondence analysis, and the effective number of codons used in a gene (see GCG CodonPreference, Genetics Computer Group Wisconsin Package; CodonW, John Peden, University of Nottingham; McInerney, J. O, 1998, Bioinformatics 14:372-73; Stenico et al., 1994, Nucleic Acids Res. 222437-46; Wright, F., 1990, Gene 87:23-29). Codon usage tables are available for a growing list of organisms (see for example, Wada et al., 1992, *Nucleic Acids Res.* 20:2111-2118; Nakamura et al., 2000, *Nucl. Acids Res.* 28:292; Duret, et al., supra; Henaut and Danchin, "*Escherichia coli* and *Salmonella*," 1996, Neidhardt, et al. Eds., ASM Press, Washington D.C., p. 2047-2066. The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTS), or predicted coding regions of genomic sequences (see for example, Mount, D., *Bioinformatics: Sequence and Genome Analysis*, Chapter 8, Cold Spring Harbor Laboratory Press, Cold Spring Harbor, N.Y., 2001; Uberbacher, E. C., 1996, *Methods Enzymol.* 266:259-281; Tiwari et al., 1997, *Comput. Appl. Biosci.* 13:263-270).

"Control sequence" is defined herein to include all components, which are necessary or advantageous for the expression of a polynucleotide and/or polypeptide of interest. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with a polynucleotide of interest, e.g., the coding region of the nucleic acid sequence encoding a polypeptide.

"Operably linked" is defined herein as a configuration in which a control sequence is appropriately placed at a position relative to a polynucleotide sequence (i.e., in a functional relationship) such that the control sequence directs the expression of the polynucleotide and/or a polypeptide encoded by the polynucleotide.

"Promoter sequence" is a nucleic acid sequence that is recognized by a host cell for expression of a polynucleotide. The control sequence may comprise an appropriate promoter sequence. The promoter sequence contains transcriptional control sequences, which mediate the expression of the polynucleotide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

6.2 Ketoreductase Enzymes

The present disclosure provides engineered ketoreductase ("KRED") enzymes that are capable of stereoselectively reducing a defined keto substrate to its corresponding alcohol product and having an improved property when compared with the naturally-occurring, wild-type KRED enzyme obtained from *L. kefir* (SEQ ID NO:2) or *L. brevis* (SEQ ID NO:4) or *L. minor* (SEQ ID NO:98) or when compared with other engineered ketoreductase enzymes. As shown in the present disclosure, the wild-type *L. kefir* or *L. brevis* or *L. minor* ketoreductase enzymes have very little activity, if any for the reduction of 2',6'-dichloro-3'-fluoroacetophenone (See the Examples). With less substituted acetophenone substrates for which the wild-type enzymes have greater activity, the wild-type enzymes are generally selective for reducing the acetophenones to their corresponding (R)-alcohols. Wild-type *Lactobacillus* species ketoreductases reduce the prototypical reference compound acetophenone to (R)-1-phenethanol and are consequently referred to as (R)-selective ketoreductases, or (R)-ketoreductases. However, the engineered ketoreductase enzymes of the disclosure, derived from a wild-type *Lactobacillus* species ketoreductase enzyme, reduce acetophenone to (S)-1-phenethanol, and are consequently referred to as (S)-selective ketoreductases, or (S)-ketoreductases. Hence, the improved ketoreductase polypeptides of the disclosure are capable of a reversed enantioselectivity for the reduction of acetophenones as compared to the wild-type *L. kefir* or *L. brevis* or *L. minor* ketoreductases. This reversed enantioselectivity is based on mutating the residue at position 190 of the wild type enzyme, preferably to a non-aromatic residue, particularly to a proline residue. Without being bound by theory, the wild-type tyrosine residue at position 190 appears to clash with the substrate in the pro-S conformation. Thus, in some embodiments, the ketoreductase polypeptides of the disclosure have at the residue corresponding to position 190 of SEQ ID NO:2 or 4 or 98 a residue which is not a tyrosine. Preferably, this residue is a non-aromatic residue, such as, for example, an aliphatic, constrained, non-polar, or cysteine residue. In some embodiments, this residue is proline.

In some embodiments, as noted above, the engineered ketoreductase with improved enzyme properties are describe in reference to *Lactobacillus kefir* ketoreductase of SEQ ID NO:4 or *Lactobacillus brevis* ketoreductase of SEQ ID NO:2 or *Lactobacillus* minor ketoreductase of SEQ ID NO:98. The amino acid residue position is determined in the ketoreductases beginning from the initiating methionine (M) residue (i.e., M represents residue position 1), although it will be understood by the skilled artisan that this initiating methionine residue may be removed by biological processing machinery, such as in a host cell or in vitro translation system, to generate a mature protein lacking the initiating methionine residue. The amino acid residue position at which a particular amino acid or amino acid change is present in an amino acid sequence is sometimes describe herein in terms "Xn", or "position n", where n refers to the residue position. Where the amino acid residues at the same residue position differ between the ketoreductases, the different residues may be denoted by an "/" with the arrangement being "*kefir* residue/*brevis* residue/minor". A substitution mutation, which is a replacement of an amino acid residue in a reference sequence, for example the wildtype ketoreductases of SEQ ID NO:2 and SEQ ID NO:4 and SEQ ID NO:98, with a different amino acid residue may be denoted by the symbol "→". Herein, mutations are sometimes described as a mutation "to a" type of amino acid. For example, residue 16 of SEQ ID NO:2 can be mutated "to a" polar residue. But the use of the phrase "to a" does not exclude mutations from one amino acid of a class to another amino acid of the same class. For example, residue 16 of SEQ ID NO:2 is a polar residue, threonine, but it can be mutated to a different polar residue, for example, the mutation can be a "T16S" (16→S) mutation.

The naturally occurring polynucleotide encoding the naturally occurring ketoreductase (also referred to as "ADH" or "alcohol dehydrogenase") of *Lactobacillus kefir, Lactobacillus brevis*, or of *Lactobacillus* minor, can be obtained from the isolated polynucleotide known to encode the ketoreductase activity (e.g., Genbank accession no. AAP94029 GI:33112056 or SEQ ID NO:3 for *Lactobacillus kefir*; Genbank accession no. CAD66648 GI:28400789 or SEQ ID NO:1 for *Lactobacillus brevis*; and SEQ ID NO:97 for *Lactobacillus* minor).

In some embodiments, the improved property (as compared to wild-type or another engineered polypeptide) of the ketoreductase polypeptide is with respect to an increase of its stereoselectivity for reducing or converting a substituted acetophenone substrate of formula (III) to its corresponding (S)-alcohol product of formula (IV). In some embodiments, the improved property of the ketoreductase property is with respect to an increase in stereoselectivity in reducing 2'6'-dichloro-3-fluoroacetophenone to (S)-1-(2,6-dichloro-3-fluorophenyl) ethanol. In some embodiments, the improved property of the ketoreductase polypeptide is with respect to an increase in its rate of conversion of the substrate to the product. In some embodiments, the improved property of the ketoreductase polypeptide is with respect to its stability or thermostability. In some embodiments, the ketoreductase polypeptide has more than one improved property.

In some embodiments, the ketoreductase polypeptides herein can have a number of modifications to the reference sequence (e.g., naturally occurring polypeptide or an engineered polypeptide) to result in the improved ketoreductase property. As used herein, "modifications" include amino acid substitutions, deletions, and insertions. Any one or a combination of modifications can be introduced into the naturally occurring or engineered polypeptide to generate engineered enzymes. In such embodiments, the number of modifications to the amino acid sequence can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 15% of the total number of amino acids, up to 20% of the total number of amino acids, or up to 30% of the total number of amino acids of the reference polypeptide sequence. In some embodiments, the number of modifications to the naturally occurring polypeptide or an engineered polypeptide that produces an improved ketoreductase property may comprise from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 modifications of the reference sequence. In some embodiments, the number of modifications can be 1, 2, 3, 4, 5, 6, 7, 8, 9, 10, 11, 12, 14, 15, 16, 18, 20, 22, 24, 26, 30, 35 or about 40 amino acid residues. The modifications can comprise insertions, deletions, substitutions, or combinations thereof.

In some embodiments, the modifications comprise amino acid substitutions to the reference sequence. Substitutions that can produce an improved ketoreductase property may be at one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the reference enzyme sequence. In some embodiments, the number of substitutions to the naturally occurring polypeptide or an engineered polypeptide that produces an improved ketoreductase property can comprise from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 amino acid substitutions of the reference sequence. In some embodiments, the number of substitutions can be 1, 2, 3, 4, 5, 6, 7, 8, 9, 10, 11, 12, 14, 15, 16, 18, 20, 22, 24, 26, 30, 35 or about 40 amino acid residues.

In some embodiments, the ketoreductase polypeptides herein comprise an amino acid sequence that is at least about 85%, 86%, 87%, 88%, 89%, 90%, 91%, 92%, 93%, 94%, 95%, 96%, 97%, 98%, 99% or more identical to a reference sequence based on SEQ ID NO: 2, 4 or 98 having at the residue corresponding to X190 a non-aromatic residue (e.g., an aliphatic, constrained, non-polar, or cysteine residue), preferably alanine, isoleucine, cysteine, or proline, particularly a proline, with the proviso that the ketoreductase polypeptide has at the residue corresponding to X190 a residue which is other than a tyrosine, particularly a non-aromatic residue. In some embodiments, the ketoreductase polypeptide has an amino acid sequence in which the residue corresponding to X190 is an aliphatic, constrained, non-polar, or cysteine residue. In some embodiments, the ketoreductase has an amino acid sequence in which the residue corresponding to X190 is alanine, isoleucine, cysteine, or proline, particularly proline. In some embodiments, these ketoreductase polypeptides can have one or more residue differences at other residue positions as compared to the reference amino acid sequence. The differences include various modifications, such as substitutions, deletions, and insertions. The substitutions can be non-conservative substitutions, conservative substitutions, or a combination of non-conservative and conservative substitutions. In some embodiments, these ketoreductase polypeptides can have optionally from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence. In some embodiments, the number of difference can be 1, 2, 3, 4, 5, 6, 7, 8, 9, 10, 11, 12, 14, 15, 16, 18, 20, 22, 24, 26, 30, 35 or about 40 residue differences at other amino acid residues as compared to the reference sequence.

In some embodiments, these stereoselective or highly stereoselective (herein, capable of reducing the substrate to the product with an e.e. that is at least about 85%) ketoreductase polypeptides comprise an amino acid sequence that corresponds to the sequence formulas as laid out in SEQ ID NO: 95, 96 and 119 (or a region or domain thereof, such as residues 90-211). SEQ ID NO:95 is based on the wild-type amino acid sequence of the *Lactobacillus brevis* ketoreductase (SEQ ID NO:2); SEQ ID NO:96 is based on the wild-type amino acid sequence of the *Lactobacillus kefir* ketoreductase (SEQ ID NO:4); and SEQ ID NO:119 is based on the wild-type amino acid sequence of the *Lactobacillus* minor ketoreductase (SEQ ID NO:98). The ketoreductase based on the sequence formula of SEQ ID NO: 95, 96, or 119 specify that the residue corresponding to X190 is a non-aromatic residue. In some embodiments, the ketoreductase polypeptide has an amino acid sequence in which the residue corresponding to X190 is alanine, isoleucine, cysteine, or proline. In some embodiments, the ketoreductase polypeptide has an amino acid sequence in which the residue corresponding to X190 is proline.

In some embodiments, the ketoreductase polypeptides comprising an amino acid sequence based on the sequence formula of SEQ ID NO: 95, 96, or 119, or a region thereof, such as residues 90-211, having the specified features for residue X190 as described herein, can further include one or more of the features selected from the following: residue corresponding to X7 is an aromatic, non-polar, polar, constrained, acidic or basic residue; residue corresponding to X16 is a polar residue; residue corresponding to X43 is a nonpolar or polar residue; residue corresponding to X60 is an aromatic, non-polar, or aliphatic residue; residue corresponding to X94 is a cysteine, non-polar or aliphatic residue; residue corresponding to X95 is a non-polar or aliphatic residue; residue corresponding to X96 is a polar or acidic residue; residue corresponding to X97 is a polar, non-polar, aliphatic, or basic residue; residue corresponding to X120 is an aromatic, non-polar or aliphatic residue; residue corresponding to X125 is a polar or non-polar residue; residue corresponding to X142 is a polar residue; residue corresponding to X147 is an aromatic, polar, non-polar, or aliphatic residue; residue corresponding to X149 is a non-polar or aromatic residue; residue corresponding to X150 is a constrained or acidic residue; residue corresponding to X152 is a non-polar or polar residue; residue corresponding to X196 is an aliphatic, non-polar, or aromatic residue; residue corresponding to X202 is an aliphatic, aromatic, or a non-polar residue; residue corresponding to X205 is a basic, nonpolar or aliphatic residue; and residue corresponding to X206 is a non-polar or aromatic residue. In some embodiments, the amino acid sequence can have two, three, four, five, six or more of the features. In some embodiments, the polypeptides comprising an amino acid sequence that corresponds to the sequence formula provided in SEQ ID NO: 95, 96, or 119 (or region thereof) can have additionally one or more of the residues not specified by an X to be mutated as compared to the reference sequence of SEQ ID NO: 2, 4 or 98. In some embodiments, the mutations can be from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 mutations at other amino acid residues not defined by X above. In some embodiments, the number of mutations can be 1, 2, 3, 4, 5, 6, 7, 8, 9, 10, 11, 12, 14, 15, 16, 18, 20, 22, 24, 26, 30, 35 or about 40 other amino acid residues. In some embodiments, the mutations comprise conservative mutations.

In some embodiments, the polypeptides comprising an amino acid sequence based on the sequence formula of SEQ ID NO: 95, 96, or 119, or region thereof, such as residues 90-211, can have one or more conservative mutations as compared to the amino acid sequences of SEQ ID NO: 2, 4 or 98. Exemplary conservative mutations include amino acid replacements such as, but not limited to: replacement of residue corresponding to X16 threonine (T) with another polar residue, e.g., asparagine, glutamine, or serine; replacement of residue corresponding to X43 valine with another non-polar or aliphatic residue, e.g., isoleucine; replacement of residue corresponding to X60 with an aliphatic or aromatic residue, e.g., alanine; replacement of residue corresponding to X94 alanine (A) with another non-polar or aliphatic residue, e.g., valine, leucine, or isoleucine; replacement of residue corresponding to X95 valine (V) with another non-polar or aliphatic residue, e.g., alanine, leucine, or isoleucine; replacement of residue corresponding to X96 serine (S) with another polar residue, e.g., asparagine, glutamine, or threonine; replacement of residue corresponding to X142 serine (S) with another polar residue, e.g., serine or asparagine; replacement of residue corresponding to X196 valine (V) with another non-polar or aliphatic residue, e.g., alanine, leucine, or isoleucine; and replacement of residue corresponding to X205 alanine (A) with another non-polar or aliphatic residue, e.g., valine, leucine, or isoleucine.

In some embodiments, the ketoreductase polypeptides comprising an amino acid sequence based on the sequence formula of SEQ ID NO: 95, 96, or 119, or a region thereof, such as residues 90-211, having the specified features for residue X190 as described herein, can further include one or more features selected from the following: residue corresponding to X7 is tryptophan, tyrosine, phenylalanine, proline, histidine, glycine, methionine, alanine, valine, leucine, isoleucine, serine, threonine, glutamine, asparagine, arginine, or lysine, particularly glycine, histidine, threonine, proline, tryptophan, arginine, histidine, or asparagine; residue corresponding to X16 is serine, threonine, asparagine, or glutamine, particularly serine; residue corresponding to X43 is glycine, methionine, alanine, valine, leucine, or isoleucine, particularly isoleucine; residue corresponding to X60 is tyrosine, phenylalanine, tryptophan, glycine, methionine, alanine, valine, leucine, or isoleucine, particularly alanine; residue corresponding to X94 is cysteine, glycine, methionine, alanine, valine, leucine, or isoleucine, particularly alanine, valine or cysteine; residue corresponding to X95 is glycine, methionine, alanine, valine, leucine, isoleucine, particularly isoleucine or leucine; residue corresponding to X96 is aspartic acid, glutamic acid, serine, threonine, asparagine, or glutamine, particularly serine, asparagine, threonine or glutamic acid; residue corresponding to X97 is serine, threonine, asparagine, glutamine, glycine, methionine, alanine, valine, leucine, isoleucine, lysine or arginine, particularly lysine, threonine, valine, arginine, methionine, or isoleucine; residue corresponding to X120 is tyrosine, phenylalanine, tryptophan, glycine, methionine, alanine, valine, leucine, or isoleucine, particularly phenylalanine or valine; residue corresponding to X125 is glycine, methionine, alanine, valine, leucine, or isoleucine, particularly glycine or serine; residue corresponding to X142 is a serine, threonine, asparagine, or glutamine residue, particularly asparagine; residue corresponding to X147 is tyrosine, phenylalanine, tryptophan, glycine, methionine, alanine, valine, leucine, isoleucine, serine, threonine, asparagine, or glutamine, particularly phenylalanine, leucine, isoleucine, valine, or glutamine; residue corresponding to X149 is glycine, methionine, alanine, valine, leucine, isoleucine, tyrosine, phenylalanine, or tryptophan, particularly glycine or phenylalanine; residue corresponding to X150 is proline, histidine, aspartic acid, or glutamic acid, particularly aspartic acid or histidine; residue corresponding to X152 is glycine, methionine, alanine, valine, leucine, isoleucine, serine, threonine, asparagine, or glutamine, particularly serine, threonine, or methionine; residue corresponding to X196 is tyrosine, phenylalanine, tryptophan, glycine, methionine, alanine, valine, leucine, or isoleucine, particularly valine, isoleucine, methionine, phenylalanine, or isoleucine; residue corresponding to X202 is tyrosine, phenylalanine, tryptophan, glycine, methionine, alanine, valine, leucine, or isoleucine, particularly alanine, tryptophan, tyrosine, or methionine; residue corresponding to X205 is lysine, arginine, glycine, methionine, alanine, valine, leucine, or isoleucine, particularly arginine; and residue corresponding to X206 is glycine, methionine, alanine, valine, leucine, isoleucine, tyrosine, phenylalanine, tryptophan, particularly methionine or tyrosine. In some embodiments, the amino acid sequence can have two, three, four, five, six or more of the features. In some embodiments, the polypeptides comprising an amino acid sequence that corresponds to the sequence formulas provided in SEQ ID NO: 95, 96, or 119 (or region thereof) can have additionally one or more of the residues not specified by an X to be mutated as compared to the reference sequence of SEQ ID NO: 2, 4 or 98. In some embodiments, the mutations can be from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 mutations at other amino acid residues not defined by X above. In some embodiments, the number of mutations can be 1, 2, 3, 4, 5, 6, 7, 8, 9, 10, 11, 12, 14, 15, 16, 18, 20, 22, 24, 26, 30, 35 or about 40 other amino acid residues. In some embodiments, the mutations comprise conservative mutations.

In some embodiments, a stereoselective ketoreductase polypeptide comprising an amino acid sequence based on the sequence formula of SEQ ID NO:95, 96 or 119, or a region thereof, such as residues 90-211, having the features at residue corresponding to X190 as described herein, can have additionally one or more or at least all of the following features: residue corresponding to X147 is an aromatic, polar, non-polar, or aliphatic residue, particularly glutamine, isoleucine, or leucine, and residue corresponding to X202 is an aliphatic, aromatic, or a non-polar residue, particularly tryptophan, methionine, or tyrosine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 98. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features.

In some embodiments, a stereoselective ketoreductase polypeptide comprising an amino acid sequence based on the sequence formula of SEQ ID NO:95, 96 or 119, or a region thereof, such as residues 90-211, having the features at residue corresponding to X190 as described herein, can have additionally one or more or at least all of the following features: residue corresponding to X7 is an aromatic, non-polar, polar, constrained, or basic residue, particularly histidine, tryptophan, proline, threonine, or arginine; residue corresponding to X147 is an aromatic, polar, non-polar, or aliphatic residue, particularly glutamine, isoleucine, or leucine; and residue corresponding to X202 is an aliphatic, aromatic, or a non-polar residue, particularly tryptophan, methionine, or tyrosine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 98. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features.

In some embodiments, a stereoselective ketoreductase polypeptide comprising an amino acid sequence based on the sequence formula of SEQ ID NO:95, 96 or 119, or a region thereof, such as residues 90-211, having the features at residue corresponding to X190 as described herein, can have additionally one or more or at least all of the following features: residue corresponding to X7 is an aromatic, non-polar, polar, constrained, or basic residue, particularly histidine, tryptophan, proline, threonine, or arginine; residue corresponding to X97 is a polar, non-polar, aliphatic, or basic residue, particularly methionine, valine, isoleucine, threonine, or arginine; residue corresponding to X147 is an aromatic, polar, non-polar, or aliphatic residue, particularly glutamine, isoleucine, or leucine; residue corresponding to X202 is an aliphatic, aromatic, or a non-polar residue, particularly tryptophan, methionine, or tyrosine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 98. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features.

In some embodiments, a stereoselective ketoreductase polypeptide comprising an amino acid sequence based on the sequence formula of SEQ ID NO:95, 96 or 119, or a region thereof, such as residues 90-211, having the features at residue corresponding to X190 as described herein, can have additionally one or more or at least all of the following features: residue corresponding to X94 is a cysteine, non-polar or an aliphatic residue, particularly cysteine or valine; residue corresponding to X96 is a polar or acidic residue, particularly threonine; and residue corresponding to X147 is an aromatic, polar, non-polar, or aliphatic residue, particularly glutamine, isoleucine, or leucine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 98. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features.

In some embodiments, a stereoselective ketoreductase polypeptide comprising an amino acid sequence based on the sequence formula of SEQ ID NO:95, 96 or 119, or a region thereof, such as residues 90-211, having the features at residue corresponding to X190 as described herein, can have additionally one or more or at least all of the following features: residue corresponding to X7 is an aromatic, non-polar, polar, constrained, or basic residue, particularly histidine, tryptophan, proline, threonine, or arginine; residue corresponding to X147 is an aromatic, polar, non-polar, or aliphatic residue, particularly glutamine, isoleucine, or leucine; residue corresponding to X196 is an aliphatic, non-polar, or aromatic residue, particularly valine, isoleucine, methionine, phenylalanine, or isoleucine; and residue corresponding to X202 is an aliphatic, aromatic, or a non-polar residue, particularly tryptophan, methionine, or tyrosine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 98. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features.

In some embodiments, a stereoselective ketoreductase polypeptide comprises an amino acid sequence based on the sequence formula of SEQ ID NO:95, 96 or 119, or a region thereof, such as residues 90-211, having the features at residue corresponding to X190 as described herein, can have additionally one or more or at least all of the following features: residue corresponding to X147 is an aromatic, polar, non-polar, or aliphatic residue, particularly glutamine, isoleucine, or leucine; residue corresponding to X196 is an aliphatic, non-polar, or aromatic residue, particularly valine, isoleucine, methionine, phenylalanine, or isoleucine; and residue corresponding to X202 is an aliphatic, aromatic, or a non-polar residue. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 98. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features.

In some embodiments, a stereoselective ketoreductase polypeptide comprises an amino acid sequence based on the sequence formula of SEQ ID NO:95, 96 or 119, or a region thereof, such as residues 90-211, having the features at residue corresponding to X190 as described herein, can have additionally one or more or at least all of the following features: residue corresponding to X7 is an aromatic, non-polar, polar, constrained, or basic residue, particularly histidine, tryptophan, proline, threonine, or arginine; residue corresponding to X96 is a polar or acidic residue, particularly threonine; residue corresponding to X147 is an aromatic, polar, non-polar, or aliphatic residue, particularly glutamine, isoleucine, or leucine; residue corresponding to X196 is an aliphatic, non-polar, or aromatic residue, particularly valine, isoleucine, methionine, phenylalanine, or isoleucine; and residue corresponding to X202 is an aliphatic, aromatic, or a non-polar residue, particularly tryptophan, methionine, or tyrosine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 98. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as to a reference sequence based on SEQ ID NO:2, 4 or 98 with the preceding features.

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline, and the residue corresponding to X7 is an aromatic, non-polar, polar, constrained, or basic residue, particularly histidine, tryptophan, proline, threonine, or arginine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 98. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features.

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline, and the residue corresponding to X16 is a polar residue, particularly serine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 98. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features.

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline, and the residue corresponding to X43 is a non-polar or aliphatic residue, particularly isoleucine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 98. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features.

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline, and the residue corresponding to X60 is an aromatic, non-polar or aliphatic residue, particularly alanine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 98. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features.

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline, and the residue corresponding to X94 is a cysteine, non-polar or an aliphatic residue, particularly cysteine or valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 98. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features.

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline, and the residue corresponding to X95 is a non-polar or aliphatic residue, particularly leucine or isoleucine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 98. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features.

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline, and the residue corresponding to X96 is a polar or acidic residue, particularly threonine or glutamic acid. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 98. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features.

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline, and the residue corresponding to X97 is a polar, non-polar, aliphatic, or basic residue, particularly methionine, valine, isoleucine, threonine, or arginine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 98. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features.

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline, and the residue corresponding to X120 is an aromatic, non-polar or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 98. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features.

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline, and the residue corresponding to X125 is a polar or non-polar residue, particularly serine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 98. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features.

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline, and the residue corresponding to X142 is a polar residue, particularly asparagine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 98. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features.

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline, and the residue corresponding to X147 is an aromatic, polar, non-polar, or aliphatic residue, particularly glutamine, leucine, or isoleucine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 98. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features.

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline, and the residue corresponding to X149 is a non-polar or aromatic residue, particularly phenylalanine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 98. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features.

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline, and the residue corresponding to X150 is a constrained or acidic residue, particularly histidine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 98. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features.

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline, and the residue corresponding to X152 is a non-polar or polar residue, particularly methionine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 98. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features.

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline, and the residue corresponding to X196 is an aliphatic, non-polar, or aromatic residue, particularly methionine, isoleucine, leucine, or phenylalanine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 98. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features.

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline, and the residue corresponding to X202 is an aliphatic, aromatic, or a non-polar residue, particularly methionine, tyrosine, or tryptophan. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 98. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features.

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline, and the residue corresponding to X205 is a basic, nonpolar or aliphatic residue, particularly arginine or valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 98. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features.

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline, and the residue corresponding to X206 is non-polar or aromatic residue, particularly tyrosine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 98. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features.

In some embodiments, an improved ketoreductase polypeptide of the disclosure comprises an amino acid sequence that has any one of the set of mutations listed in Table 2 below. In some embodiments, the polypeptide has at least 85%, 86%, 87%, 88%, 89%, 90%, 91%, 92%, 93%, 94%, 95%, 96%, 97%, 98%, or 99% sequence identity to a polypeptide comprising an amino acid sequence selected from SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, and 94, wherein the ketoreductase polypeptide amino acid sequence includes any one set of the substitution combinations listed in Table 2. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other amino acid residues as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, the improved ketoreductase polypeptide comprises an amino acid sequence selected from SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, and 94.

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline, and residue corresponding to X196 is an aliphatic, non-polar, or aromatic residue, particularly methionine, isoleucine, leucine, or phenylalanine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:2, 4 or 98 with the preceding features, such as SEQ ID NO:8, 10, 14, 16, 24, 26 or 48. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features (e.g., SEQ ID NO:8, 10, 14, 16, 24, 26 or 48)

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline; residue corresponding to X125 is a polar or non-polar residue, particularly serine; and residue corresponding to X196 is an aliphatic, non-polar, or aromatic residue, particularly methionine, isoleucine, leucine, or phenylalanine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:2, 4 or 98 with the preceding features, such as SEQ ID NO:52. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features (e.g., SEQ ID NO:52).

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline; residue corresponding to X95 is a non-polar or aliphatic residue, particularly leucine or isoleucine; and residue corresponding to X196 is an aliphatic, non-polar, or aromatic residue, particularly methionine, isoleucine, leucine, or phenylalanine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:2, 4 or 98 with the preceding features, such as SEQ ID NO:20, 62, or 64. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features (e.g., SEQ ID NO:20, 62, or 64).

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline; residue corresponding to X196 is an aliphatic, non-polar, or aromatic residue, particularly methionine, isoleucine, leucine, or phenylalanine; and residue corresponding to X206 is a non-polar or aromatic residue, particularly tyrosine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:2, 4 or 98 with the preceding features, such as SEQ ID NO:36. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features (e.g., SEQ ID NO:36).

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline; residue corresponding to X7 is an aromatic, non-polar, polar, constrained, or basic residue, particularly histidine, tryptophan, proline, threonine, or arginine; and residue corresponding to X196 is an aliphatic, non-polar, or aromatic residue, particularly methionine, isoleucine, leucine, or phenylalanine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:2, 4 or 98 with the preceding features, such as SEQ ID NO:54 or 56. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features (e.g., SEQ ID NO:54 or 56).

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline; residue corresponding to X147 is an aromatic, polar, non-polar, or aliphatic residue, particularly glutamine, leucine, or isoleucine; and residue corresponding to X196 is an aliphatic, non-polar, or aromatic residue, particularly methionine, isoleucine, leucine, or phenylalanine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:2, 4 or 98 with the preceding features, such as SEQ ID NO:22, 66, 68, or 72. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features (e.g., SEQ ID NO:22, 66, 68, or 72).

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline; residue corresponding to X196 is an aliphatic, non-polar, or aromatic residue, particularly methionine, isoleucine, leucine, or phenylalanine; and residue corresponding to X202 is an aliphatic, aromatic, or a non-polar residue, particularly methionine, tyrosine, or tryptophan. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:2, 4 or 98 with the preceding features, such as SEQ ID NO:28, 30, or 32. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features (e.g., SEQ ID NO:28, 30, or 32).

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline; residue corresponding to X152 is a non-polar or polar residue, particularly methionine; residue corresponding to X196 is an aliphatic, non-polar, or aromatic residue, particularly methionine, isoleucine, leucine, or phenylalanine; and residue corresponding to X205 is a basic, nonpolar or aliphatic residue, particularly arginine or valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:2, 4 or 98 with the preceding features, such as SEQ ID NO:20. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features (e.g., SEQ ID NO:20).

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline; residue corresponding to X43 is a non-polar or aliphatic residue, particularly isoleucine; residue corresponding to X147 is an aromatic, polar, nonpolar, or aliphatic residue, particularly glutamine, leucine, or isoleucine; residue corresponding to X196 is an aliphatic, non-polar, or aromatic residue, particularly methionine, isoleucine, leucine, or phenylalanine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:2, 4 or 98 with the preceding features, such as SEQ ID NO:70. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features (e.g., SEQ ID NO:70).

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline; residue corresponding to X94 is a cysteine, non-polar or an aliphatic residue, particularly cysteine or valine; residue corresponding to X196 is an aliphatic, non-polar, or aromatic residue, particularly methionine, isoleucine, leucine, or phenylalanine; and residue corresponding to X205 is an aromatic, polar, non-polar, or aliphatic residue, particularly glutamine, leucine, or isoleucine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:2, 4 or 98 with the preceding features, such as SEQ ID NO:34. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features (e.g., SEQ ID NO:34).

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline; residue corresponding to X97 is a polar, non-polar, aliphatic, or basic residue, particularly arginine, valine, methionine, threonine, or isoleucine; residue corresponding to X147 is an aromatic, polar, non-polar, or aliphatic residue, particularly glutamine, leucine, or isoleucine; and residue corresponding to X196 is an aliphatic, non-polar, or aromatic residue, particularly methionine, isoleucine, leucine, or phenylalanine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:2, 4 or 98 with the preceding features, such as SEQ ID NO:74. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features (e.g., SEQ ID NO:74).

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline; residue corresponding to X7 is an aromatic, non-polar, polar, constrained, or basic residue, particularly histidine, threonine, proline, tryptophan or arginine; residue corresponding to X147 is an aromatic, polar, non-polar, or aliphatic residue, particularly glutamine, leucine, or isoleucine; residue corresponding to X196 is an aliphatic, non-polar, or aromatic residue, particularly methionine, isoleucine, leucine, or phenylalanine; and residue corresponding to X202 is an aliphatic, aromatic, or a non-polar residue, particularly methionine, tyrosine, or tryptophan. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:2, 4 or 98 with the preceding features, such as SEQ ID NO:40, 76, 78, 80, or 82. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features (e.g., SEQ ID NO:40, 76, 78, 80, or 82).

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline; residue corresponding to X7 is an aromatic, non-polar, polar, constrained, or basic residue, particularly histidine, threonine, proline, tryptophan or arginine; residue corresponding to X94 is a cysteine, non-polar or an aliphatic residue, particularly cysteine or valine; residue corresponding to X147 is an aromatic, polar, non-polar, or aliphatic residue, particularly glutamine, leucine, or isoleucine; residue corresponding to X196 is an aliphatic, non-polar, or aromatic residue, particularly methionine, isoleucine, leucine, or phenylalanine; and residue corresponding to X202 is an aliphatic, aromatic, or a non-polar residue, particularly methionine, tyrosine, or tryptophan. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:2, 4 or 98 with the preceding features, such as SEQ ID NO:42. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features (e.g., SEQ ID NO:42).

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline; residue corresponding to X7 is an aromatic, non-polar, polar, constrained, or basic residue, particularly histidine, threonine, proline, tryptophan or arginine; residue corresponding to X94 is a cysteine, non-polar or an aliphatic residue, particularly cysteine or valine; residue corresponding to X147 is an aromatic, polar, non-polar, or aliphatic residue, particularly glutamine, leucine, or isoleucine; residue corresponding to X149 is a non-polar or aromatic residue, particularly phenylalanine; residue corresponding to X150 is a constrained or acidic residue, particularly histidine; residue corresponding to X196 is an aliphatic, non-polar, or aromatic residue, particularly methionine, isoleucine, leucine, or phenylalanine; and residue corresponding to X202 is an aliphatic, aromatic, or a non-polar residue, particularly methionine, tyrosine, or tryptophan. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:2, 4 or 98 with the preceding features, such as SEQ ID NO:84. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features (e.g., SEQ ID NO:84).

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline; residue corresponding to X7 is an aromatic, non-polar, polar, constrained, or basic residue, particularly histidine, threonine, proline, tryptophan or arginine; residue corresponding to X96 is a polar or acidic residue, particularly threonine or glutamic acid; residue corresponding to X147 is an aromatic, polar, non-polar, or aliphatic residue, particularly glutamine, leucine, or isoleucine; residue corresponding to X196 is an aliphatic, non-polar, or aromatic residue, particularly methionine, isoleucine, leucine, or phenylalanine; and residue corresponding to X202 is an aliphatic, aromatic, or a non-polar residue, particularly methionine, tyrosine, or tryptophan. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:2, 4 or 98 with the preceding features, such as SEQ ID NO:44 or 46. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features (e.g., SEQ ID NO:44 or 46).

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline; residue corresponding to X7 is an aromatic, non-polar, polar, constrained, or basic residue, particularly histidine, threonine, proline, tryptophan or arginine; residue corresponding to X96 is a polar or acidic residue, particularly threonine or glutamic acid; residue corresponding to X120 is an aromatic, non-polar or aliphatic residue, particularly valine; residue corresponding to X147 is an aromatic, polar, non-polar, or aliphatic residue, particularly glutamine, leucine, or isoleucine; residue corresponding to X196 is an aliphatic, non-polar, or aromatic residue, particularly methionine, isoleucine, leucine, or phenylalanine; and residue corresponding to X202 is an aliphatic, aromatic, or a non-polar residue, particularly methionine, tyrosine, or tryptophan. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:2, 4 or 98 with the preceding features, such as SEQ ID NO:86. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features (e.g., SEQ ID NO:86).

In some embodiments, an improved ketoreductase comprises an amino acid sequence based on the sequence formula of SEQ ID NO: 95, 96, or 119, or a region thereof, such as residues 90-211, in which the amino acid sequence has at least the following features: residue corresponding to X190 is an non-aromatic residue, particularly alanine, isoleucine, cysteine, or proline; residue corresponding to X7 is an aromatic, non-polar, polar, constrained, or basic residue, particularly histidine, threonine, proline, tryptophan or arginine; residue corresponding to X97 is a polar, non-polar, aliphatic, or basic residue, particularly valine, methionine, threonine, or isoleucine; residue corresponding to X147 is an aromatic, polar, non-polar, or aliphatic residue, particularly glutamine, leucine, or isoleucine; residue corresponding to X196 is an aliphatic, non-polar, or aromatic residue, particularly methionine, isoleucine, leucine, or phenylalanine; and residue corresponding to X202 is an aliphatic, aromatic, or a non-polar residue, particularly methionine, tyrosine, or tryptophan. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other residue positions as compared to a reference sequence of SEQ ID NO:2, 4 or 98 with the preceding features, such as SEQ ID NO:88, 90, 92 or 94. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence with the preceding features, and wherein the amino acid sequence has at least 85%, 86%, 87%, 88%, 89%, 90%, 91%, 92%, 93%, 94%, 95%, 96%, 97%, 98%, or 99% identity to a reference sequence based on SEQ ID NO:2, 4 or 98 with the preceding features (e.g., SEQ ID NO:88, 90, 92 or 94).

In some embodiments, the improved ketoreductases of the disclosure comprises an amino acid sequence that has a region or domain corresponding to residues 90-211 of the sequence formula of SEQ ID NO: 95, 96, or 119 in which the residue corresponding to X190 is not tyrosine. In some embodiments, the domain or region corresponding to residues 90-211 comprises an amino acid sequence in which the residue corresponding to X190 is a non-aromatic residue, such as an aliphatic, constrained, non-polar, or cysteine residue. In some embodiments, the domain or region corresponding to residues 90-211 comprises an amino acid sequence in which the residue corresponding to X190 is alanine, isoleucine, cysteine, or proline, particularly proline. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the corresponding domain of a reference sequence based on SEQ ID NO: 2, 4, or 98. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with a domain or region corresponding to residues 90-211 of the sequence formula of SEQ ID NO:95, 96, or 119 in which the residue corresponding to X190 has at least the preceding features, and wherein the amino acid sequence of the domain or region has at least 85%, 86%, 87%, 88%, 89%, 90%, 91%, 92%, 93%, 94%, 95%, 96%, 97%, 98%, or 99% identity to the amino acid sequence corresponding to residues 90-211 of a reference sequence based on SEQ ID NO:2, 4 or 98 with the preceding features.

In some embodiments, the ketoreductase polypeptide with a domain or region corresponding to residues 90-211 of the sequence formula of SEQ ID NO:95, 96 or 119 and having the specified features at residue corresponding to X190 as described herein, can further include in the region or domain one or more of the features selected from the following: residue corresponding to X94 is a cysteine, non-polar or an aliphatic residue; residue corresponding to X95 is a non-polar or aliphatic residue; residue corresponding to X96 is a polar or acidic residue; residue corresponding to X97 is a polar, non-polar, aliphatic, or basic residue; residue corresponding to X120 is an aromatic, non-polar or aliphatic residue; residue corresponding to X125 is a polar or non-polar residue; residue corresponding to X147 is an aromatic, polar, non-polar, or aliphatic residue; residue corresponding to X149 is a non-polar or aromatic residue; residue corresponding to X150 is a constrained or acidic residue; residue corresponding to X152 is a non-polar or polar residue; residue corresponding to X196 is an aliphatic, non-polar, or aromatic residue; residue corresponding to X202 is an aliphatic, aromatic, or a non-polar residue; residue corresponding to X205 is a basic, nonpolar or aliphatic residue; and residue corresponding to X206 is non-polar or aromatic residue. In some embodiments, the region or domain corresponding to residues 90-211 can have additionally from about 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the corresponding domain of a reference sequence based on SEQ ID NO:2, 4 or 98. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations.

In some embodiments, the ketoreductases polypeptides having a domain or region with an amino acid sequence corresponding to residues 90-211 of the sequence formula of SEQ ID NO: 95, 96 or 119, as described above, can have one or more conservative mutations in the domain or region as compared to the amino acid sequence of the corresponding domain of SEQ ID NO: 2, 4 or 98. Examples of such conservative mutations include amino acid replacements such as, but limited to: replacement of residue corresponding to X94 alanine (A) with another non-polar or aliphatic residue, e.g., valine, leucine, or isoleucine; replacement of residue corresponding to X95 valine (V) with another non-polar or aliphatic residue, e.g., alanine, leucine, or isoleucine; replacement of residue corresponding to X96 serine (S) with another polar residue, e.g., asparagine, glutamine, or threonine; replacement of residue corresponding to X196 valine (V) with another non-polar or aliphatic residue, e.g., alanine, leucine, or isoleucine; and replacement of residue corresponding to X205 alanine (A) with another non-polar or aliphatic residue, e.g., valine, leucine, or isoleucine.

In some embodiments, the ketoreductase polypeptide with a domain or region corresponding to residues 90-211 of the sequence formula of SEQ ID NO:95, 96 or 119 and having the specified features at residue corresponding to X190 as described herein, can further include in the region or domain one or more of the features selected from the following: residue corresponding to X94 is cysteine, glycine, methionine, alanine, valine, leucine, or isoleucine, particularly alanine, valine or cysteine; residue corresponding to X95 is glycine, methionine, alanine, valine, leucine, isoleucine, particularly isoleucine or leucine; residue corresponding to X96 is aspartic acid, glutamic acid, serine, threonine, asparagine, or glutamine, particularly serine, asparagine, threonine or glutamic acid; residue corresponding to X97 is serine, threonine, asparagine, glutamine, glycine, methionine, alanine, valine, leucine, isoleucine, lysine or arginine, particularly lysine, threonine, valine, arginine, methionine, or isoleucine; residue corresponding to X120 is tyrosine, phenylalanine, tryptophan, glycine, methionine, alanine, valine, leucine, or isoleucine, particularly phenylalanine or valine; residue corresponding to X125 is glycine, methionine, alanine, valine, leucine, or isoleucine, particularly glycine or serine; residue corresponding to X142 is a serine, threonine, asparagine, or glutamine residue, particularly asparagine; residue corresponding to X147 is tyrosine, phenylalanine, tryptophan, glycine, methionine, alanine, valine, leucine, isoleucine, serine, threonine, asparagine, or glutamine, particularly phenylalanine, leucine, isoleucine, valine, or glutamine; residue corresponding to X149 is glycine, methionine, alanine, valine, leucine, isoleucine, tyrosine, phenylalanine, or tryptophan, particularly glycine or phenylalanine; residue corresponding to X150 is proline, histidine, aspartic acid, or glutamic acid, particularly aspartic acid or histidine; residue corresponding to X152 is glycine, methionine, alanine, valine, leucine, isoleucine, serine, threonine, asparagine, or glutamine, particularly serine, threonine, or methionine; residue corresponding to X196 is tyrosine, phenylalanine, tryptophan, glycine, methionine, alanine, valine, leucine, or isoleucine, particularly valine, isoleucine, methionine, phenylalanine, or isoleucine; residue corresponding to X202 is tyrosine, phenylalanine, tryptophan, glycine, methionine, alanine, valine, leucine, or isoleucine, particularly alanine, tryptophan, tyrosine, or methionine; residue corresponding to X205 is lysine, arginine, glycine, methionine, alanine, valine, leucine, or isoleucine, particularly arginine; and residue corresponding to X206 is glycine, methionine, alanine, valine, leucine, isoleucine, tyrosine, phenylalanine, tryptophan, particularly methionine or tyrosine. In some embodiments, the region or domain corresponding to residues 90-211 can have additionally from about 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the corresponding domain of a reference sequence based on SEQ ID NO:2, 4 or 98. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations.

In some embodiments, the ketoreductase polypeptide with a domain or region corresponding to residues 90-211 of the sequence formula of SEQ ID NO:95, 96 or 119 and having the specified features at residue corresponding to X190 as described herein, can further include in the region or domain one or more or all of the features selected from the following: residue corresponding to X147 is an aromatic, polar, non-polar, or aliphatic residue, particularly glutamine, isoleucine, or leucine, and residue corresponding to X202 is an aliphatic, aromatic, or a non-polar residue, particularly tryptophan, methionine, or tyrosine. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4 or 98. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:2, 4 or 98 with the preceding features.

In some embodiments, the ketoreductase polypeptide with a domain or region corresponding to residues 90-211 of the sequence formula of SEQ ID NO:95, 96 or 119 and having the specified features at residue corresponding to X190 as described herein, can further include in the region or domain one or more or all of the features selected from the following: residue corresponding to X97 is a polar, non-polar, aliphatic, or basic residue, particularly methionine, valine, isoleucine, threonine, or arginine; residue corresponding to X147 is an aromatic, polar, non-polar, or aliphatic residue, particularly glutamine, isoleucine, or leucine; residue corresponding to X202 is an aliphatic, aromatic, or a non-polar residue, particularly tryptophan, methionine, or tyrosine. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4 or 98. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:2, 4 or 98 with the preceding features.

In some embodiments, the ketoreductase polypeptide with a domain or region corresponding to residues 90-211 of the sequence formula of SEQ ID NO:95, 96 or 119 and having the specified features at residue corresponding to X190 as described herein, can further include in the region or domain one or more or all of the features selected from the following: residue corresponding to X94 is a cysteine, non-polar or an aliphatic residue, particularly cysteine or valine; residue corresponding to X96 is a polar or acidic residue, particularly threonine; and residue corresponding to X147 is an aromatic, polar, non-polar, or aliphatic residue, particularly glutamine, isoleucine, or leucine. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues as compared to the domain of a reference sequence based on SEQ ID NO:2, 4 or 98. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 90-211 of a reference sequence based on SEQ ID NO:2, 4 or 98 with the preceding features.

In some embodiments, the ketoreductase polypeptide can further include a region or domain corresponding to residues 1-89 of the sequence formula of SEQ ID NO:95, 96, or 119. In some embodiments, the region or domain corresponding to residues 1-89 can have one or more of the following features: residue corresponding to X7 is an aromatic, non-polar, polar, constrained, or basic residue; residue corresponding to X16 is a polar residue; residue corresponding to X43 is a nonpolar or polar residue; and residue corresponding to X60 is an aromatic or non-polar, or aliphatic residue.

In some embodiments, the domain or region corresponding to residues 1-89 can have at least 85%, 86%, 87%, 88%, 89%, 90%, 91%, 92%, 93%, 94%, 95%, 96%, 97%, 98%, or 99% identity to the amino acid sequence corresponding to residues 1-89 of a reference sequence based on SEQ ID NO:2, 4, or 98 having at the residue corresponding to X7 an aromatic, non-polar, polar, constrained, or basic residue, particularly a histidine, with the proviso that the region or domain of the ketoreductase polypeptide has an amino acid sequence in which the residue corresponding to X7 is an aromatic, non-polar, polar, constrained, or basic residue, particularly a histidine. In some embodiments, the region or domain corresponding to residues 1-89 can have additionally 1-2, 1-3, 1-4, 1-5, 1-6, 1-7, 1-8, 1-9, 1-10, 1-11, 1-12, 1-14, 1-15, or 1-16 residue differences at other amino acid residues as compared to the domain of a reference sequence based on SEQ ID NO:2, 4 or 98. In some embodiments, the number of differences can be 1, 2, 3, 4, 5, 6, 7, 8, 9, 10, 11, 12, 14, 15, or about 16 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 1-89 of a reference sequence based on SEQ ID NO:2, 4 or 98 with the preceding features.

In some embodiments, the region or domain corresponding to residues 1-89 can have one or more or at least all of the following features: residue corresponding to X7 is an aromatic, non-polar, polar, constrained, or basic residue; residue corresponding to X16 is a polar residue; residue corresponding to X43 is a nonpolar or polar residue; and residue corresponding to X60 is an aromatic or non-polar, or aliphatic residue. In some embodiments, the region or domain corresponding to residues 1-89 can have additionally 1-2, 1-3, 1-4, 1-5, 1-6, 1-7, 1-8, 1-9, 1-10, 1-11, 1-12, 1-14, 1-15, or 1-16 residue differences at other amino acid residues as compared to the domain of a reference sequence based on SEQ ID NO:2, 4 or 98. In some embodiments, the number of differences can be 1, 2, 3, 4, 5, 6, 7, 8, 9, 10, 11, 12, 14, 15, or 16 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 1-89 of a reference sequence based on SEQ ID NO:2, 4 or 98 with the preceding features.

In some embodiments, the region or domain corresponding to residues 1-89 can have one or more or at least all of the following features: residue corresponding to X7 is tryptophan, tyrosine, phenylalanine, proline, histidine, glycine, methionine, alanine, valine, leucine, isoleucine, serine, threonine, glutamine, asparagine, arginine, or lysine, particularly glycine, histidine, threonine, proline, tryptophan, arginine, histidine, or asparagine; residue corresponding to X16 is serine, threonine, asparagine, or glutamine, particularly serine; residue corresponding to X43 is glycine, methionine, alanine, valine, leucine, or isoleucine, particularly isoleucine; and residue corresponding to X60 is tyrosine, phenylalanine, tryptophan, glycine, methionine, alanine, valine, leucine, or isoleucine, particularly alanine. In some embodiments, the region or domain corresponding to residues 1-89 can have additionally 1-2, 1-3, 1-4, 1-5, 1-6, 1-7, 1-8, 1-9, 1-10, 1-11, 1-12, 1-14, 1-15, or 1-16 residue differences at other amino acid residues as compared to the domain of a reference sequence based on SEQ ID NO:2, 4 or 98. In some embodiments, the number of differences can be 1, 2, 3, 4, 5, 6, 7, 8, 9, 10, 11, 12, 14, 15, or 16 residue differences at other amino acid residues in the domain. In some embodiments, the differences comprise conservative mutations. In some embodiments, the ketoreductase polypeptide comprises an amino acid sequence with at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 1-89 of a reference sequence based on SEQ ID NO:2, 4 or 98 with the preceding features.

Table 2 below provides a list of some of the SEQ ID NOs disclosed herein with associated activity levels with respect to reduction of substituted acetophenones. All sequences below are derived from the wild-type *L. kefir* ketoreductase sequences (SEQ ID NO: 3 and 4) unless otherwise specified.

TABLE 2

List of Sequences

| Polynucleotide SEQ ID NO. | Polypeptide SEQ ID NO. | Polypeptide Residue Substitutions as Compared to SEQ ID NO: 4 | Activity | Stability |
|---|---|---|---|---|
| 3 | 4 | None. (Wild-type *L. kefir* sequence) | – | – |
| 5 | 6 | Y190C | + | – |
| 7 | 8 | Y190A; V196I; | ++ | + |
| 9 | 10 | Y190P; V196I; | ++ | |
| 11 | 12 | K97R; Y190C; | + | |
| 13 | 14 | Y190P; V196L | ++ | |
| 15 | 16 | Y190A; V196L | ++ | + |
| 47 | 48 | Y190P; V196M; | + | |
| 49 | 50 | Y190P; V196F; | + | |
| 51 | 52 | G125S; Y190P; V196L; | + | |
| 19 | 20 | V95I; Y190P; V196I; | + | + |
| 17 | 18 | T152M; Y190P; V196I; M205R; | +++ | + |
| 23 | 24 | Y190P; V196L; (as compared to SEQ ID NO: 2) | ++ | |
| 25 | 26 | Y190A; V196L; (as compared to SEQ ID NO: 2) | ++ | + |
| 35 | 36 | Y190P; V196L; M206Y; | +++ | |
| 53 | 54 | G7N; Y190A; V196L; | ++ | + |
| 55 | 56 | G7H; Y190P; V196L; | ++ | |
| 61 | 62 | V95L; Y190P; V196L; | ++ | |
| 63 | 64 | V95I; Y190P; V196L; | ++ | |
| 57 | 58 | T16S; Y190P; V196L; | ++ | |
| 59 | 60 | Y190P; V196L | ++ | |
| 21 | 22 | F147L; Y190P; V196L; | ++ | ++ |
| 65 | 66 | F147Q; Y190A; V196L; | ++ | + |
| 67 | 68 | F147I; Y190P; V196L; | ++ | ++ |
| 69 | 70 | V43I; F147L; Y190P; V196L; | ++ | ++ |
| 71 | 72 | F147L; Y190A; V196L; | ++ | ++ |
| 31 | 32 | Y190P; V196L; A202W; | +++ | + |
| 27 | 28 | Y190P; V196L; A202M; | ++ | + |
| 29 | 30 | Y190A; V196L; A202Y; | ++ | + |
| 33 | 34 | A94V; Y190A; V196L; M205V; | +++ | + |
| 73 | 74 | K97R; F147I; Y190P; V196L; | +++ | + |
| 37 | 38 | F147L; Y190P; V196L; A202W; | +++ | ++ |
| 39 | 40 | G7H; F147L; Y190P; V196L; A202W; | +++ | ++ |
| 75 | 76 | G7T; F147L; Y190P; V196L; A202W; | +++ | ++ |
| 77 | 78 | G7P; F147L; Y190P; V196L; A202W; | +++ | ++ |
| 79 | 80 | G7W; F147L; Y190P; V196L; A202W; | +++ | ++ |
| 81 | 82 | G7R; F147L; Y190P; V196L; A202W; | +++ | ++ |
| 83 | 84 | G7H; A94C; F147L; G149F; D150H; Y190P; V196L; A202W; | +++ | ++ |
| 41 | 42 | G7H; A94V; F147L; Y190P; V196L; A202W; | +++ | ++ |
| 43 | 44 | G7H; S96E; F147L; Y190P; V196L; A202W; | +++ | ++ |
| 85 | 86 | G7H; S96T; F120V; F147L; Y190P; V196L; A202W; | +++ | ++ |
| 45 | 46 | G7H; S96T; F147L; Y190P; V196L; A202W; | +++ | ++ |
| 87 | 88 | G7H; K97V; F147L; Y190P; V196L; A202W; | +++ | ++ |
| 89 | 90 | G7H; K97M; F147L; Y190P; V196L; A202W; | +++ | ++ |
| 91 | 92 | G7H; K97T; F147L; Y190P; V196L; A202W; | +++ | ++ |
| 93 | 94 | G7H; K97I; F147L; Y190P; V196L; A202W; | +++ | ++ |

In Table 2 above, in the activity column, a single plus "+" indicates an activity improvement of 100-450% of the activity of SEQ ID NO:6, two pluses "++" indicates an activity improvement of 450-1500% of SEQ ID NO:6, and three pluses "+++" indicates an activity improvement of greater than 1500% of SEQ ID NO:6. In the stability column, a single plus "+" indicates that the polypeptide exhibits measurable activity after heat treatment of 2 hours at 50° C., two pluses "++" indicates that the polypeptide has greater than 400% improvement in activity as compared to SEQ ID NO:16 when comparing activity for both proteins after heat treatment of 2 hours at 50° C.

In some embodiments, the ketoreductase polypeptides of the disclosure are improved as compared to an engineered KRED enzyme having (S) selectivity, e.g., SEQ ID NO:6, with respect to their rate of enzymatic activity, for example, their rate of converting the substrate to the product. The polypeptide having the sequence of SEQ ID NO:6 is used herein as a reference polypeptide because the wild-type *L. kefir* or *L. brevis* KRED do not exhibit appreciable activity for converting 2',6'-dichloro-3'-fluoroacetophenone to (S)-

1-[2,6-dichloro-3-fluorophenyl]-ethanol. In some embodiments, the ketoreductase polypeptides are capable of converting the substrate to the product at a rate that is at least 5-fold, 10-fold, 25-fold, 50-fold, 75-fold, 100-fold, 150-fold, 200-fold, 250-fold, or 300-fold over the rate of SEQ ID NO:6. In some embodiments, the ketoreductase polypeptides are capable of converting the substrate to the product at a rate that is at least 100%, 150%, 200%, 250%, 300%, 400%, 450%, 500%, 750%, 1000%, 1250%, or 1500% of the rate of SEQ ID NO:6.

In some embodiments, the ketoreductase polypeptide of the disclosure is capable of converting 2',6'-dichloro-3'-fluoroacetophenone to (S)-1-[2,6-dichloro-3-fluorophenyl]-ethanol with an stereomeric excess greater than 99% and at a rate that is improved over the ketoreductase polypeptide having the sequence of SEQ ID NO:6. Exemplary polypeptides that are improved over SEQ ID NO:6 with respect to enzymatic activity, include but are not limited to, polypeptides comprising amino acid sequences corresponding to SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, and 94.

In some embodiments, the ketoreductase polypeptide of the disclosure is capable of converting 2',6'-dichloro-3'-fluoroacetophenone to (S)-1-[2,6-dichloro-3-fluorophenyl]-ethanol with an stereomeric excess greater than 99% and at a rate that is improved over the ketoreductase polypeptide having the sequence of SEQ ID NO:6, wherein the polypeptide also has improved thermostability as compared to the polypeptide having the sequence of SEQ ID NO:6. Exemplary polypeptides having such improvements include, but are not limited to, polypeptides comprising amino acid sequences corresponding to SEQ ID NO: 8, 16, 18, 20, 22, 26, 28, 30, 32, 34, 38, 40, 42, 44, 46, 54, 66, 68, 70, 72, 74, 76, 78, 80, 82, 84, 86, 88, 90, 92, and 94.

In some embodiments, the ketoreductase polypeptide of the disclosure is capable of converting 2',6'-dichloro-3'-fluoroacetophenone to (S)-1-[2,6-dichloro-3-fluorophenyl]-ethanol with an stereomeric excess greater than 99% and at a rate that is at least about 450% greater than the ketoreductase polypeptide having the sequence of SEQ ID NO:6. Exemplary polypeptides capable of such an improvement include, but are not limited to, polypeptides comprising amino acid sequences corresponding to SEQ ID NO: 8, 10, 14, 16, 18, 22, 24, 26, 28, 30, 32, 34, 36, 38, 40, 42, 44, 46, 54, 56, 58, 60, 62, 64, 66, 68, 70, 72, 74, 76, 78, 80, 82, 84, 86, 88, 90, 92, and 94.

In some embodiments, the ketoreductase polypeptide of the disclosure is capable of converting 2',6'-dichloro-3'-fluoroacetophenone to (S)-1-[2,6-dichloro-3-fluorophenyl]-ethanol with an stereomeric excess greater than 99% and at a rate that is at least about 450% greater than the ketoreductase polypeptide having the sequence of SEQ ID NO:6, wherein the polypeptide also has an improved thermostability as compared to the polypeptide of SEQ ID NO:6. Exemplary polypeptides having such properties include, but are not limited to, polypeptides comprising amino acid sequences corresponding to SEQ ID NO: 8, 16, 18, 22, 26, 28, 30, 32, 34, 38, 40, 42, 44, 46, 54, 66, 68, 70, 72, 74, 76, 78, 80, 82, 84, 86, 88, 90, 92, and 94.

In some embodiments, the ketoreductase polypeptide of the disclosure is capable of converting 2',6'-dichloro-3'-fluoroacetophenone to (S)-1-[2,6-dichloro-3-fluorophenyl]-ethanol with an stereomeric excess greater than 99% and at a rate that is at least about 1500% greater than the ketoreductase polypeptide having the sequence of SEQ ID NO:6. Exemplary polypeptides capable of such an improvement include, but are not limited to, polypeptides comprising amino acid sequences corresponding to SEQ ID NO: 18, 32, 34, 36, 38, 40, 42, 44, 46, 74, 76, 78, 80, 82, 84, 86, 88, 90, 92, and 94.

In some embodiments, the ketoreductase polypeptide of the disclosure is capable of converting 2',6'-dichloro-3'-fluoroacetophenone to (S)-1-[2,6-dichloro-3-fluorophenyl]-ethanol with an stereomeric excess greater than 99% and at a rate that is at least about 1500% greater than the ketoreductase polypeptide having the sequence of SEQ ID NO:6, wherein the polypeptide also has an improved thermostability as compared to the polypeptide of SEQ ID NO:6. Exemplary polypeptides having such properties include, but are not limited to, polypeptides comprising amino acid sequences corresponding to SEQ ID NO: 18, 32, 34, 36, 38, 40, 42, 44, 46, 74, 76, 78, 80, 82, 84, 86, 88, 90, 92, and 94.

In some embodiments, the ketoreductase polypeptide of the disclosure is capable of converting in less than about 24 hours at least about 95% of the 2',6'-dichloro-3'-fluoroacetophenone substrate to (S)-1-(2,6-dichloro-3-fluorophenyl) ethanol, in at least about 99% stereomeric excess, when carried out with the polypeptide at an amount of less than about 1% by weight with respect to the amount of the 2',6'-dichloro-3'-fluoroacetophenone substrate. Exemplary polypeptides that have this capability include, but are not limited to, polypeptides comprising amino acid sequences corresponding to 18, 32, 34, 36, 38, 40, 42, 44, 46, 74, 76, 78, 80, 82, 84, 86, 88, 90, 92, and 94.

In some embodiments, the ketoreductase polypeptide of the disclosure is capable of converting 2',6'-dichloro-3'-fluoroacetophenone to (S)-1-[2,6-dichloro-3-fluorophenyl]-ethanol with an stereomeric excess greater than 99% and at a rate that is at least about 450% greater than the ketoreductase polypeptide having the sequence of SEQ ID NO:6, wherein the polypeptide is also capable, after a heat treatment of 50° C. for 2 hours, of converting the substrate to the product at a rate that is at least about 400% greater than the polypeptide having the sequence of SEQ ID NO:16 (where the polypeptide of SEQ ID NO:16 was also treated with the same heat treatment). Exemplary polypeptides having such properties include, but are not limited to, polypeptides comprising amino acid sequences corresponding to SEQ ID NO: 18, 32, 34, 36, 38, 40, 42, 44, 46, 74, 76, 78, 80, 82, 84, 86, 88, 90, 92, and 94.

In some embodiments, the ketoreductase polypeptide is capable of stereoselectively reducing the substrate to the product with a percent e.e. that is at least about 99%, where the polypeptide comprises an amino acid sequences corresponding to SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, or 94.

In some embodiments, the ketoreductase polypeptide is capable of stereoselectivity reducing a 2',6'-dichloro-3-fluoroacetophenone to (S)-1-(2,6-dichloro-3-fluorophenyl) ethanol with a percent stereomeric excess of at least about 25%, 50%, 75%, 80%, 85%, 85%, 87%, 88%, 89%, 90%, 91%, 92%, 93%, 94%, 95%, 96%, 97%, 98%, 99%, 99.9%, or 99.99%.

In some embodiments, the ketoreductase polypeptides can comprise an amino acid sequence that is at least about 85%, 86%, 87%, 88%, 89%, 90%, 91%, 92%, 93%, 94%, 95%, 96%, 97%, 98%, or 99% identical to SEQ ID NO:2, 4 or 98, or a region or domain thereof, such as residues 90-211, with the proviso that the residue corresponding to residue X190 is not tyrosine, particularly a non-aromatic residue, and where the polypeptide is capable of reducing the substrate to the product with at least about 85% e.e. In some embodiments, the residue corresponding to X190 is an aliphatic, constrained, non-polar, or cysteine residue. In some embodiments, the residue corresponding to X190 is proline, and additionally has one or more of the following substitutions such that the polypeptide is further improved (with respect to stereoselectivity, enzymatic activity, and/or thermostability) over the wild-type *L. kefir* ketoreductase or another engineered ketoreductase: 7→H,T,P,W,R,N (i.e., the residue corresponding to residue 7 of SEQ ID NO:2, 4, or 98 is substituted to histidine, threonine, proline, tryptophan, arginine, or asparagine); 16→S; 43→I; 60→A; 94→C,V; 95→I, L; 96→E,T; 97→R,V,M,T,I; 120→V; 125→S; 142→N; 147→L,Q,I,V; 149→F; 150→H; 152→H; 196→I,L,M,F; 202→W,M,F; and 206→Y. In some embodiments, the residue corresponding to X190 is proline, and additionally has one or more of the following substitutions such that the polypeptide is further improved over the wild-type *kefir* ketoreductase or another engineered ketoreductase: 7→H; 94→V; 96→T; 147→L; 196→L; and 202→W.

As will be appreciated by those of skill in the art, some of the above-defined categories, unless otherwise specified, are not mutually exclusive. Thus, amino acids having side chains exhibiting two or more physico-chemical properties can be included in multiple categories. The appropriate classification of any amino acid or residue will be apparent to those of skill in the art, especially in light of the detailed disclosure provided herein.

In some embodiments, the improved engineered ketoreductase enzymes comprise deletions of the naturally occurring ketoreductase polypeptides or deletions of other engineered ketoreductase polypeptides. In some embodiments, each of the improved engineered ketoreductase enzymes described herein can comprise deletions of the polypeptides described herein. Thus, for each and every embodiment of the ketoreductase polypeptides of the disclosure, the deletions can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the ketoreductase polypeptides, as long as the functional activity of the ketoreductase activity is maintained. In some embodiments, the deletions can comprise, 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 amino acid residues. In some embodiments, the number of deletions can be 1, 2, 3, 4, 5, 6, 7, 8, 9, 10, 11, 12, 14, 15, 16, 18, 20, 22, 24, 26, 30, 35 or about 40 amino acids. In some embodiments, the deletions can comprise deletions of 1, 2, 3, 4, 5, 6, 7, 8, 9, 10, 11, 12, 13, 14, 15, 16, 18, or 20 amino acid residues.

As described herein, the ketoreductase polypeptides of the disclosure can be in the form of fusion polypeptides in which the ketoreductases polypeptides are fused to other polypeptides, such as antibody tags (e.g., myc epitope) or purifications sequences (e.g., His tags). Thus, the ketoreductase polypeptides can be used with or without fusions to other polypeptides.

In some embodiments, the polypeptides described herein are not restricted to the genetically encoded amino acids. In addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-stereomers of the genetically-encoded amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutanic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisolencine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, *CRC Practical Handbook of Biochemistry and Molecular Biology*, CRC Press, Boca Raton, Fla., at pp. 3-70 and the references cited therein, all of which are incorporated by reference). These amino acids may be in either the L- or D-configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys(methylbenzyl), Cys (nitropyridinesulfenyl), Glu(δ-benzylester), Gln(xanthyl), Asn(N-δ-xanthyl), His(bom), His (benzyl), His(tos), Lys(fmoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

As described above the various modifications introduced into the naturally occurring polypeptide to generate an engineered ketoreductase enzyme can be targeted to a specific property of the enzyme.

6.3 Polynucleotides Encoding Engineered Ketoreductases

In another aspect, the present disclosure provides polynucleotides encoding the engineered ketoreductase enzymes. The polynucleotides may be operatively linked to one or more heterologous regulatory sequences that control gene expression to create a recombinant polynucleotide capable of expressing the polypeptide. Expression constructs containing a heterologous polynucleotide encoding the engineered ketoreductase can be introduced into appropriate host cells to express the corresponding ketoreductase polypeptide.

Because of the knowledge of the codons corresponding to the various amino acids, availability of a protein sequence provides a description of all the polynucleotides capable of encoding the subject. The degeneracy of the genetic code, where the same amino acids are encoded by alternative or synonymous codons allows an extremely large number of nucleic acids to be made, all of which encode the improved ketoreductase enzymes disclosed herein. Thus, having identified a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made by selecting combinations based on the possible codon choices, and all such variations are to be considered specifically disclosed for any polypeptide disclosed herein, including the amino acid sequences presented in Table 2. In various embodiments, the codons are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells. By way of example, the polynucleotide of SEQ ID NO: 3 has been codon optimized for expression in *E. coli*, but otherwise encodes the naturally occurring ketoreductase of *Lactobacillus kefir*.

In some embodiments, the polynucleotide comprises a nucleotide sequence encoding a ketoreductase polypeptide with an amino acid sequence that has at least about 85%, 86%, 87%, 88%, 89%, 90%, 91%, 92%, 93%, 94%, 95%, 96%, 97%, 98%, or 99% or more sequence identity to any of the reference engineered ketoreductase polypeptides described herein, where the encoded ketoreductase polypeptide comprises an amino acid sequence in which the residue corresponding to X190 of SEQ ID NO:2, 4 or 98 is not a tyrosine. In some embodiments, the polynucleotide encodes a ketoreductase polypeptide comprising an amino acid sequence in which the residue corresponding to X190 is a non-aromatic residue. In some embodiments, the polynucleotide encodes a ketoreductase polypeptide comprising an amino acid sequence in which the residue corresponding to X190 is alanine, isoleucine, cysteine, or proline, particularly proline. In some embodiments, the polynucleotide encodes an engineered ketoreductase polypeptide comprising an amino acid sequence selected from SEQ ID NO:6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, and 94.

In some embodiments, the polynucleotides encoding the engineered ketoreductases are selected from SEQ ID NO: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, and 93. In some embodiments, the polynucleotides are capable of hybridizing under highly stringent conditions to a polynucleotide comprising SEQ ID NO: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, and 93, wherein the polynucleotide hybridizing under highly stringent conditions has (S)-selectivity for a substituted acetophenone substrate, e.g., capable for reducing or converting the substrate of structural formula (I) to the product of structural formula (II). In some embodiments, the polynucleotides hybridizing under highly stringent conditions are capable of reducing or converting the substrate of structural formula (III) to the product of structural formula (IV).

In some embodiments, the polynucleotides encode the polypeptides described herein but have about 80% or more sequence identity, about 85%, 86%, 87%, 88%, 89%, 90%, 91%, 92%, 93%, 94%, 95%, 96%, 97%, 98%, or 99% or more sequence identity at the nucleotide level to a reference polynucleotide encoding the engineered ketoreductase. In some embodiments, the reference polynucleotide is selected from a polynucleotide sequence corresponding to SEQ ID NO: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, and 93.

An isolated polynucleotide encoding an improved ketoreductase polypeptide may be manipulated in a variety of ways to provide for expression of the polypeptide. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, *Molecular Cloning: A Laboratory Manual,* 3rd Ed., Cold Spring Harbor Laboratory Press; and *Current Protocols in Molecular Biology*, Ausubel. F. ed., Greene Pub. Associates, 1998, updates to 2006.

For bacterial host cells, suitable promoters for directing transcription of the nucleic acid constructs of the present disclosure, include the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proc. Natl Acad. Sci. USA* 75: 3727-3731), as well as the tac promoter (DeBoer et al., 1983, *Proc. Natl Acad. Sci. USA* 80: 21-25). Further promoters are described in Sambrook et al., supra.

For filamentous fungal host cells, suitable promoters for directing the transcription of the nucleic acid constructs of the present disclosure include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8:423-488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are described by Guo and Sherman, 1995, *Mol Cell Bio* 15:5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region.

Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NC1B 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, Microbiol Rev 57: 109-137.

Effective signal peptide coding regions for filamentous fungal host cells can be the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells can be from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter.

Other examples of regulatory sequences are those which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the KRED polypeptide of the present invention would be operably linked with the regulatory sequence.

Thus, in some embodiments, the present disclosure is also directed to a recombinant expression vector comprising a polynucleotide encoding an engineered ketoreductase polypeptide or a variant thereof, and one or more expression regulating regions such as a promoter and a terminator, a replication origin, etc., depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present disclosure may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vector of the present invention preferably contains one or more selectable markers, which permit easy selection of transformed cells. A selectable marker can be a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol (Example 1) or tetracycline resistance. Suitable markers for yeast host cells are ADE2, HIS3, LEU2, LYS2, MET3, TRP1, and URA3.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*.

The expression vectors of the present invention can contain an element(s) that permits integration of the vector into the host cell's genome or autonomous replication of the vector in the cell independent of the genome. For integration into the host cell genome, the vector may rely on the nucleic acid sequence encoding the polypeptide or any other element of the vector for integration of the vector into the genome by homologous or nonhomologous recombination.

Alternatively, the expression vector may contain additional nucleic acid sequences for directing integration by homologous recombination into the genome of the host cell. The additional nucleic acid sequences enable the vector to be integrated into the host cell genome at a precise location (s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are P15A ori or the origins of replication of plasmids pBR322, pUC19, pACYC177 (which plasmid has the P15A ori), or pACYC184 permitting replication in *E. coli*, and pUB110, pE194, pTA1060, or pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proc Natl Acad Sci. USA* 75:1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

Many of the expression vectors for use in the present disclosure are commercially available. Suitable commercial expression vectors include p3×FLAGTM™ expression vectors from Sigma-Aldrich Chemicals, St. Louis Mo., which includes a CMV promoter and hGH polyadenylation site for expression in mammalian host cells and a pBR322 origin of replication and ampicillin resistance markers for amplification in *E. coli*. Other suitable expression vectors are pBluescriptII SK(−) and pBK-CMV, which are commercially available from Stratagene, LaJolla Calif., and plasmids which are derived from pBR322 (Gibco BRL), pUC (Gibco BRL), pREP4, pCEP4 (Invitrogen) or pPoly (Lathe et al., 1987, *Gene* 57:193-201).

6.4 Host Cells for Expression of Ketoreductase Polypeptides

In another aspect, the present disclosure provides a host cell comprising a polynucleotide encoding an improved ketoreductase polypeptide of the present disclosure, the polynucleotide being operatively linked to one or more control sequences for expression of the ketoreductase enzyme in the host cell. Host cells for use in expressing the KRED polypeptides encoded by the expression vectors of the present invention are well known in the art and include but are not limited to, bacterial cells, such as *E. coli, Lactobacillus kefir, Lactobacillus brevis, Lactobacillus minor, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Appropriate culture mediums and growth conditions for the above-described host cells are well known in the art.

Polynucleotides for expression of the ketoreductase may be introduced into cells by various methods known in the art. Techniques include among others, electroporation, biolistic particle bombardment, liposome mediated transfection, calcium chloride transfection, and protoplast fusion. Various methods for introducing polynucleotides into cells will be apparent to the skilled artisan.

An exemplary host cell is *Escherichia coli* W3110. The expression vector was created by operatively linking a polynucleotide encoding an improved ketoreductase into the plasmid pCK110900 operatively linked to the lac promoter under control of the lad repressor. The expression vector also contained the P15a origin of replication and the chloramphenicol resistance gene. Cells containing the subject polynucleotide in *Escherichia coli* W3110 can be isolated by subjecting the cells to chloramphenicol selection.

6.5 Methods of Generating Engineered Ketoreductase Polypeptides

In some embodiments, to make the improved KRED polynucleotides and polypeptides of the present disclosure, the naturally-occurring ketoreductase enzyme that catalyzes the reduction reaction is obtained (or derived) from *Lactobacillus kefir* or *Lactobacillus brevis* or *Lactobacillus* minor. In some embodiments, the parent polynucleotide sequence is codon optimized to enhance expression of the ketoreductase in a specified host cell. As an illustration, the parental polynucleotide sequence encoding the wild-type KRED polypeptide of *Lactobacillus kefir* was constructed from oligonucleotides prepared based upon the known polypeptide sequence of *Lactobacillus kefir* KRED sequence available in Genbank database (Genbank accession no. AAP94029 GI:33112056). The parental polynucleotide sequence, designated as SEQ ID NO: 3, was codon optimized for expression in *E. coli* and the codon-optimized polynucleotide cloned into an expression vector, placing the expression of the ketoreductase gene under the control of the lac promoter and lad repressor gene. Clones expressing the active ketoreductase in *E. coli* were identified and the genes sequenced to confirm their identity. The sequence designated (SEQ ID NO: 3) was the parent sequence utilized as the starting point for most experiments and library construction of engineered ketoreductases evolved from the *Lactobacillus kefir* ketoreductase.

The engineered ketoreductases can be obtained by subjecting the polynucleotide encoding the naturally occurring ketoreductase to mutagenesis and/or directed evolution methods, as discussed above. An exemplary directed evolution technique is mutagenesis and/or DNA shuffling as described in Stemmer, 1994, *Proc Natl Acad Sci USA* 91:10747-10751; WO 95/22625; WO 97/0078; WO 97/35966; WO 98/27230; WO 00/42651; WO 01/75767 and U.S. Pat. No. 6,537,746. Other directed evolution procedures that can be used include, among others, staggered extension process (StEP), in vitro recombination (Zhao et al., 1998, *Nat. Biotechnol.* 16:258-261), mutagenic PCR (Caldwell et al., 1994, *PCR Methods Appl.* 3:S136-S140), and cassette mutagenesis (Black et al., 1996, *Proc Natl Acad Sci* USA 93:3525-3529). Additional mutagenesis and directed evolution techniques useful for the purposes herein can be found in the following references: Ling, et al., 1997, "Approaches to DNA mutagenesis: an overview," *Anal. Biochem.* 254(2):157-78; Dale et al., 1996, "Oligonucleotide-directed random mutagenesis using the phosphorothioate method," *Methods Mol. Biol.* 57:369-74; Smith, 1985, "In vitro mutagenesis," *Ann. Rev. Genet.* 19:423-462; Botstein et al., 1985, "Strategies and applications of in vitro mutagenesis," *Science* 229:1193-1201; Carter, 1986, "Site-directed mutagenesis," *Biochem. J.* 237:1-7; Kramer et al., 1984, "Point Mismatch Repair," *Cell,* 38:879-887; Wells et al., 1985, "Cassette mutagenesis: an efficient method for generation of multiple mutations at defined sites," *Gene* 34:315-323; Minshull et al., 1999, "Protein evolution by molecular breeding," *Curr Opin Chem Biol* 3:284-290; Christians et al., 1999, "Directed evolution of thymidine kinase for AZT phosphorylation using DNA family shuffling," *Nature Biotech* 17:259-264; Crameri et al., 1998, "DNA shuffling of a family of genes from diverse species accelerates directed evolution," *Nature* 391:288-291; Crameri et al., 1997, "Molecular evolution of an arsenate detoxification pathway by DNA shuffling," *Nature Biotech* 15:436-438; Zhang et al., 1997, "Directed evolution of an effective fructosidase from a galactosidase by DNA shuffling and screening," *Proc Natl Acad Sci USA* 94:45-4-4509; Crameri et al., 1996, "Improved green fluorescent protein by molecular evolution using DNA shuffling,' *Nature Biotech* 14:315-319; and Stemmer, 1994, "Rapid evolution of a protein in vitro by DNA shuffling," *Nature* 370:389-391. All publications are incorporated herein by reference.

The clones obtained following mutagenesis treatment are screened for engineered ketoreductases having a desired improved enzyme property. Measuring enzyme activity from the expression libraries can be performed using the standard biochemistry technique of monitoring the rate of decrease (via a decrease in absorbance or fluorescence) of NADH or NADPH concentration, as it is converted into $NAD^+$ or $NADP^+$. (For example, see Example 7.) In this reaction, the NADH or NADPH is consumed (oxidized) by the ketoreductase as the ketoreductase reduces a ketone substrate to the corresponding hydroxyl group. The rate of decrease of NADH or NADPH concentration, as measured by the decrease in absorbance or fluorescence, per unit time indicates the relative (enzymatic) activity of the KRED polypeptide in a fixed amount of the lysate (or a lyophilized powder made therefrom). The stereochemistry of the products can be ascertained by various known techniques, and as provided in the Examples. Where the improved enzyme property desired is thermal stability, enzyme activity may be measured after subjecting the enzyme preparations to a defined temperature and measuring the amount of enzyme activity remaining after heat treatments. Clones containing a polynucleotide encoding a ketoreductase are then isolated, sequenced to identify the nucleotide sequence changes (if any), and used to express the enzyme in a host cell.

Where the sequence of the engineered polypeptide is known, the polynucleotides encoding the enzyme can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides and oligonucleotides of the invention can be prepared by chemical synthesis using, e.g., the classical phosphoramidite method described by Beaucage et al., 1981*, Tet Lett* 22:1859-69, or the method described by Matthes et al., 1984*, EMBO J.* 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors. In addition, essentially any nucleic acid can be obtained from any of a variety of commercial sources, such as The Midland Certified Reagent Company, Midland, Tex., The Great American Gene Company, Ramona, Calif., ExpressGen Inc. Chicago, Ill., Operon Technologies Inc., Alameda, Calif., and many others.

Engineered ketoreductase enzymes expressed in a host cell can be recovered from the cells and or the culture medium using any one or more of the well known techniques for protein purification, including, among others, lysozyme treatment, sonication, filtration, salting-out, ultra-centrifugation, and chromatography. Suitable solutions for lysing and the high efficiency extraction of proteins from bacteria, such as *E. coli*, are commercially available under the trade name CelLytic B™ from Sigma-Aldrich of St. Louis Mo.

Chromatographic techniques for isolation of the ketoreductase polypeptide include, among others, reverse phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

In some embodiments, affinity techniques may be used to isolate the improved ketoreductase enzymes. For affinity chromatography purification, any antibody which specifically binds the ketoreductase polypeptide may be used. For the production of antibodies, various host animals, including but not limited to rabbits, mice, rats, etc., may be immunized by injection with the ketoreductase. The ketoreductase polypeptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette Guerin) and *Corynebacterium parvum.*

The ketoreductases may be prepared and used in the form of cells expressing the enzymes, as crude extracts, or as isolated or purified preparations. The ketoreductases may be prepared as lyophilizates, in powder form (e.g., acetone powders), or prepared as enzyme solutions. In some embodiments, the ketoreductases can be in the form of substantially pure preparations.

In some embodiments, the ketoreductase polypeptides can be attached to a solid substrate. The substrate can be a solid phase, surface, and/or membrane. A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of the substrate can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location. A plurality of supports can be configured on an array at various locations, addressable for robotic delivery of reagents, or by detection methods and/or instruments.

6.6 Methods of Using the Engineered Ketoreductase Enzymes and Compounds Prepared Therewith The ketoreductase enzymes described herein are capable of catalyzing the reduction reaction of the keto group in a 2',6' substituted acetophenone substrate, optionally substituted at one or more of 3',4' or 5' positions, to the corresponding substituted (S)-phenethanol.

In some embodiments, the ketoreductases are capable of reducing or converting the substrate compound of structural formula (I), (2',6'-dichloro-3'-fluoroacetophenone):

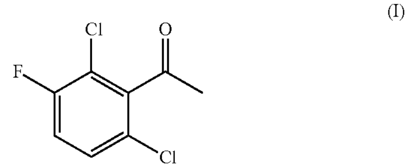

(I)

to the corresponding chiral alcohol product of structural formula (II), (S)-1-[2,6-dichloro-3-fluorophenyl]-ethanol:

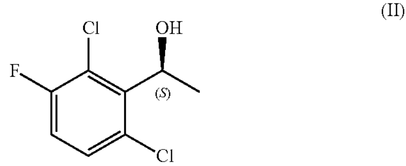

(II)

In some embodiments, the ketoreductases described herein are capable of reducing or converting 2',6'-substituted acetophenone compounds of structural formula (III):

(III)

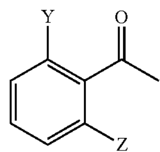

wherein Y and Z are independently selected from $CH_3$, $CF_3$, $NH_2$, OH, $OCH_3$, Cl, and Br, to the corresponding chiral alcohol product of structural formula (IV):

(IV)

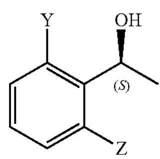

In some embodiments, a ketoreductase enzyme described herein is capable of catalyzing the reduction reaction of 2',6'-substituted acetophenone compounds of structural formula (III), which can be similarly substituted at one or more of the 3',4', and 5' positions, to the corresponding (S)-alcohol product. The capability of the ketoreductases described herein to catalyze the reduction reaction of a specific further substituted 2',6'-substituted acetophenone compound, in addition to acetophenone, can be determined by routine experimentation, for example by methods such as described in the Examples. The compound, 2',6'-dichloro-3'-fluoroacetophenone, of structural formula (I) is an example of a further substituted 2',6'-substituted acetophenone compound. As such, in some embodiments, the ketoreductase enzymes disclosed herein are capable of catalyzing the reduction reaction of the compound of structural formula (V):

(V)

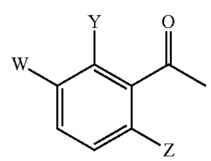

wherein Y and Z are independently selected from $CH_3$, $CF_3$, $NH_2$, OH, $OCH_3$, Cl, and Br, and W is selected from H or F, Cl, or Br. to the corresponding (S) alcohol product of the structural formula (VI):

(VI)

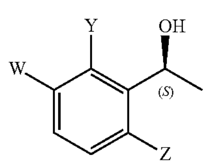

Thus, in some embodiments, the ketoreductases described herein can be used in a method for reducing a 2',6'-substituted acetophenone substrate, optionally substituted at one or more of 3',4' or 5' positions, to the corresponding substituted (S)-phenethanol, where the method comprises contacting the substituted acetophenone substrate with the ketoreductases described herein under reaction conditions suitable for reducing or converting the substituted acetophenone to the corresponding substituted (S)-phenethanol. In some embodiments of this method, the substrate is reduced to the product in greater than about 25%, 50%, 75%, 80%, 85%, 90%, 95%, 99%, or 99.9% stereomeric excess.

In some embodiments, the ketoreductases described herein can be used in a method for reducing the 2',6'-substituted acetophenone substrate of formula (III) to corresponding substituted (S)-phenethanol compound of formula (IV), where the method comprises contacting or incubating the compound of formula (III) with a ketoreductase polypeptide described herein under reaction conditions suitable for reducing or converting the compound of formula (III) to the corresponding substituted (S)-phenethanol compound of formula (IV). In some embodiments of this method, the substrate is reduced to the product in greater than about 25%, 50%, 75%, 80%, 85%, 90%, 95%, 99%, or 99.9% stereomeric excess.

In some embodiments, the ketoreductases described herein can be used in a method for reducing a 2',6'-dichloro-3'-fluoroacetophenone substrate of formula (I) to its corresponding (S)-alcohol product, (S)-1-[2,6-dichloro-3-fluorophenyl]-ethanol, of formula (II), where the method comprises contacting or incubating 2',6'-dichloro-3'-fluoroacetophenone with a ketoreductase polypeptide described herein under reaction conditions suitable for reducing or converting 2',6'-dichloro-3'-fluoroacetophenone to (S)-1-[2,6-dichloro-3-fluorophenyl]-ethanol. In some embodiments of this method, the substrate is reduced to the product in greater than about 85%, 90%, 95%, 99%, or 99.9% stereomeric excess. In some embodiments, the substrate is reduced to the product in greater than about 85% stereomeric excess, wherein the ketoreductase polypeptide comprises an amino acid sequence based on the sequence formula of SEQ ID NO:95, 96 or 119.

In some embodiments, an engineered (S)-selective ketoreductase enzyme derived from a wild-type *Lactobacillus* species ketoreductase enzyme can be used in a method to reduce acetophenone to (S)-1-phenethanol in greater than about 85%, 90%, 91%, 92%, 93%, 94%, 95%, 96%, 97%, 98%, 99%, or 99.9% or more stereomeric excess.

In some embodiments, the substrate is reduced to the product in greater than about 99% stereomeric excess, wherein the ketoreductase polypeptide used in the method comprises an amino acid sequence selected from SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, and 94. In some embodiments of this method, at least about 95% of the substrate is reduced to the product in greater than about 99% stereomeric excess in less than 24 hours when the method is carried out with the ketoreductase polypeptide at an amount of less than about 1% by weight with respect to the amount of the 2',6'-dichloro-3'-fluoroacetophenone substrate.

In some embodiments of the method, at least about 95% of the substrate is reduced to the product in at least about 99% stereomeric excess in less than 24 hours, when the method is conducted with at least about 200 g/L of substrate and less than about 1 g/L of the ketoreductase polypeptide, wherein the ketoreductase polypeptide used in the method comprises an amino acid sequence selected from SEQ ID NO: 18, 32, 34, 36, 38, 40, 42, 44, 46, 74, 76, 78, 80, 82, 84, 86, 88, 90, 92, and 94.

In some embodiments, the ketoreductases polypeptides and the methods of the present disclosure can be used for synthesis of protein tyrosine kinase inhibitor compounds described in WO2006021886 (aminoheteroaryl compounds), WO2006021884 (enantiomerically substantially pure aminoheteroaryl compounds), WO2006021881 (pyrazole-substituted aminoheteroaryl compounds), and WO2004076412 (aminoheteroaryl compounds)), whose synthesis relies on the compound of formula (II) as an intermediate. All references are incorporated herein by reference in their entirety.

Accordingly, in some embodiments, the ketoreductase polypeptides and the methods described herein can be used in producing the protein tyrosine kinase inhibitor compound of structural formula (VII), (VII)

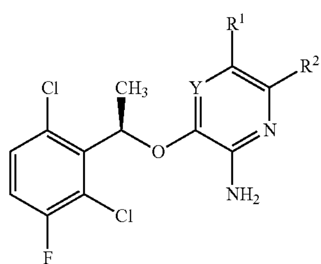

including salts, hydrates, and solvates thereof, as described in references WO04076412 and WO06021884, wherein $R^1$, $R^2$, Y and N are described therein. In some embodiments, for the compound of formula (VII), Y is N or $CR^{12}$;

$R^1$ is selected from hydrogen, halogen, $C_{6-12}$ aryl, 5-12 membered heteroaryl, $C_{3-12}$ cycloalkyl, 3-12 membered heteroalicyclic, $—O(CR^6R^7)_nR^4$, $—C(O)R^4$, $—C(O)OR^4$, —CN, $—NO_2$, $—S(O)_mR^4$, $—SO_2NR^4R^5$, $—C(O)NR^4R^5$, $—NR^4C(O)R^5$, $—C(=NR^6)NR^4R^5$, $C_{1-8}$ alkyl, $C_{2-8}$ alkenyl, and $C_{2-8}$ alkynyl; and each hydrogen in $R^1$ is optionally substituted by one or more $R^3$ groups;

$R^2$ is hydrogen, halogen, $C_{1-2}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, $—S(O)_mR^4$, $—SO_2NR^4R^5$, $—S(O)_2OR^4$, $—NO_2$, $—NR^4R^5$, $—(CR^6R^7)_nOR^4$, —CN, $—C(O)R^4$, $—OC(O)R^4$, $—O(CR^6R^7)_nR^4$, $—NR^4C(O)R^5$, $—(CR^6R^7)_nC(O)OR^4$, $—(CR^6R^7)_nNCR^4R^5$, $—C(=NR_6)NR^4R^5$, $—NR^4C(O)NR^5R^6$, $—NR^4S(O)_pR^5$ or $—C(O)NR^4R^5$, and each hydrogen in $R^2$ is optionally substituted by $R^8$;

each $R^3$ is independently halogen, $C_{1-2}$ alkyl, $C_{2-12}$ alkenyl, $C_{2-12}$ alkynyl, $C_{3-12}$ cycloalkyl, $C_{6-2}$ aryl, 3-12 membered heteroalicyclic, 5-12 membered heteroaryl, $—S(O)_mR^4$, $—SO^2NR^4R^5$, $—S(O)_2OR^4$, $—NO_2$, $—NR^4R^5$, $—(CR^6R^7)_nOR^4$, —CN, $—C(O)R^4$, $—OC(O)R^4$, $—O(CR^6R^7)_nR^4$, $—NR^4C(O)R^5$, $—(CR^6R^7)_nC(O)OR^4$, $—(CR^6R^7)_nOR^4$, $—(CR^6R^7)_nC(O)NR^4R^5$, $—(CR^6R^7)_nNCR^4R^5$, $—C(=NR^6)NR^4R^5$, $—NR^4C(O)NR^5R^6$, $—NR^4S(O)PR^5$ or $—C(O)NR^4R^5$, each hydrogen in $R^3$ is optionally substituted by $R^8$, and $R^3$ groups on adjacent atoms may combine to form a $C_{6-12}$ aryl, 5-12 membered heteroaryl, $C_{3-12}$ cycloalkyl or 3-12 membered heteroalicyclic group;

each $R^4$, $R^5$, $R^6$ and $R^7$ is independently hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl; or any two of $R^4$, $R^5$, $R^6$ and $R^7$ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from N, O, and S; or any two of $R^4$, $R^5$, $R^6$ and $R^7$ bound to the same carbon atom may be combined to form a $C_{3-12}$ cycloalkyl, $C_{6-12}$ aryl, 3-12 membered heteroalicyclic or 5-12 membered heteroaryl group; and each hydrogen in $R^4$, $R^5$, $R^6$ and $R^7$ is optionally substituted by $R^8$;

each $R^8$ is independently halogen, $C_{1-12}$ alkyl, $C_{2-12}$ alkenyl, $C_{2-12}$ alkynyl, $C_{3-12}$ cycloalkyl, C6-12 aryl, 3-12 membered heteroalicyclic, 5-12 membered heteroaryl, $—NH_2$, —CN, —OH, $—O—C_{1-12}$ alkyl, $—O—(CH_2)_nC_{3-12}$ cycloalkyl, $—O—(CH_2)_nC_{6-12}$ aryl, $—O—(CH_2)_n$(3-12 membered heteroalicyclic) or $—O—(CH_2)_n$(5-12 membered heteroaryl); and each hydrogen in $R^8$ is optionally substituted by $R^{11}$;

each $R^9$ and $R^{10}$ is independently hydrogen, halogen, $C_{1-12}$ alkyl, $C_{3-12}$ cycloalkyl, $C_{6-12}$ aryl, 3-12 membered heteroalicyclic, 5-12 membered heteroaryl, $—S(O)_mR^4$, $—SO_2NR^4R^5$, $—S(O)_2OR^4$, $—NO_2$, $—NR^4R^5$, $—(CR^6R^7)_nOR^4$, —CN, $—C(O)R^4$, $—OC(O)R^4$, $—NR^4C(O)R^5$, $—(CR^6R^7)_nC(O)OR^4$, $—(CR^6R^7)_nNCR^4R^5$, $—NR^4C(O)NR^5R^6$, $—NR^4S(O)_pR^5$ or $—C(O)NR^4R^5$; $R^9$ or $R^{10}$ may combine with a ring atom of A or a substituent of A to form a $C_{3-12}$ cycloalkyl, 3-12 membered heteroalicyclic, $C_{6-12}$ aryl or 5-12 membered heteroaryl ring fused to A; and each hydrogen in $R^9$ and $R^{10}$ is optionally substituted by $R^3$;

each $R^{11}$ is independently halogen, $C_{1-12}$ alkyl, $C_{1-12}$ alkoxy, $C_{3-12}$ cycloalkyl, $C_{6-12}$ aryl, 3-12 membered heteroalicyclic, 5-12 membered heteroaryl, $—O—C_{1-12}$ alkyl, $—O—(CH_2)_nC_{3-12}$ cycloalkyl, $—O—(CH_2)_nC_{6-12}$ aryl, $—O—(CH_2)_n$(3-12 membered heteroalicyclic), $—O—(CH_2)_n$(5-12 membered heteroaryl) or —CN, and each hydrogen in $R^{11}$ is optionally substituted by halogen, —OH, —CN, $—C^{1-12}$ alkyl which may be partially or fully halogenated, $—O—C_{1-12}$ alkyl which may be partially or fully halogenated, —CO, —SO or $—SO_2$;

$R^{12}$ is hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, $—S(O)_mR^4$, $—SO_2NR^4R^5$, $—S(O)_2OR^4$, $—NO_2$, $—NR^4R^5$, $—(CR^6R^7)_nOR^4$, —CN, $—C(O)R^4$, $—OC(O)R^4$, $—O(CR^6R^7)_nR^4$, $—NR^4C(O)R^5$, $—(CR^6R^7)_nC(O)OR^4$, $—(CR^6R^7)_nNCR^4R^5$, $—C(=NR^6)NR^4R^5$, $—NR^4C(O)NR^5R^6$, $—NR^4S(O)_pR^5$ or $—C(O)NR^4R^5$, and each hydrogen in $R^{12}$ is optionally substituted by $R^3$;

each $R^{13}$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, $—S(O)_mR^4$, $—SO_2NR^4R^5$, $—S(O)_2OR^4$, $—NO_2$, $—NR^4R^5$, $—(CR^6R^7)_nOR^4$, —CN, $—C(O)R^4$, $—OC(O)R^4$, $—O(CR^6R^7)_nR^4$, $—NR^4C(O)R^5$, $—(CR^6R^7)_nC(O)OR^4$, $—(CR^6R^7)_nOR^4$, $—(CR^6R^7)_nC(O)NR^4R^5$, $—(CR^6R^7)_nNCR^4R^5$, $—C(=NR^6)NR^4R^5$, $—NR^4C(O)NR^5R^6$, $—NR^4S(O)_pR^5$, $—C(O)NR^4R^5$, $—(CR^6R^7)_n$(3-12 membered heteroalicyclic), $—(CR^6R^7)_n(C_{3-12}$ cycloalkyl), $—(CR^6R^7)_n(C_{6-12}$ aryl), $—(CR^6R^7)_n$(5-12 membered heteroaryl), $—(CR^6R^7)_nC(O)NR^4R^5$, or $—(CR^6R^7)_nC(O)R^4$, $R^{13}$ groups on adjacent atoms may combine to form a $C_{6-12}$ aryl, 5-12 membered heteroaryl, $C_{3-12}$ cycloalkyl or 3-12 membered heteroalicyclic group, and each hydrogen in $R^{13}$ is optionally substituted by $R^3$;

wherein, each m is independently 0, 1 or 2; each n is independently 0, 1, 2, 3 or 4; and each p is independently 1 or 2. Descriptions of the various substituents as well as specific compounds encompassed by formula (VII) are described in WO04076412 and WO06021884.

Accordingly, in a method for producing an enantiomerically pure compound of structural formula (VII), a step in the method can comprise reducing or converting a compound of formula (I) to the compound of formula (II) using the ketoreductase polypeptides described herein under reaction conditions suitable for reducing or converting the substrate compound of formula (I) to the product compound of formula (II). Synthesis of the compounds of formula (VII) from the compound of formula (II) are described in the cited references.

In some embodiments, the ketoreductase polypeptides and the methods described herein can be used in producing the protein tyrosine kinase inhibitor compound of structural formula (VIII),

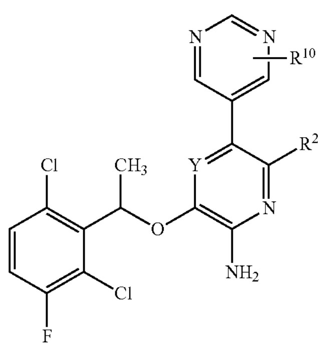

(VIII)

including salts, hydrates and solvates thereof, as described in WO06021886, where $R^{10}$, $R^2$, Y, and N are described therein. In some embodiments, for the compound of formula (VIII), Y is N or $CR^1$;

$R^1$ is hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —$S(O)_mR^4$, —$SO_2NR^4R^5$, —$S(O)_2OR^4$, —$NO_2$, —$NR^4R^5$, —$(CR^6R^7)_nOR^4$, —CN, —$C(O)R^4$, —$OC(O)R^4$, —$O(CR^6R^7)_nR^4$, —$NR^4C(O)R^5$, —$(CR^6R^7)_nC(O)OR^4$, —$(CR^6R^7)_nNCR^4R^5$, —$C(=NR^6)NR^4R^5$, —$NR^4C(O)NR^5R^6$, —$NR^4S(O)_pR^5$ or —$C(O)NR^4R^5$, and each hydrogen in $R^1$ is optionally substituted by $R^3$;

$R^2$ is hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —$S(O)_mR^4$, —$SO_2NR^4R^5$, —$S(O)_2OR^4$, —$NO_2$, —$NR^4R^5$, —$(CR^6R^7)_nOR^4$, —CN, —$C(O)R^4$, —$OC(O)R^4$, —$O(CR^6R^7)_nR^4$, —$NR^4C(O)R^5$, —$(CR^6R^7)_nC(O)OR^4$, —$(CR^6R^7)_nNCR^4R^5$, —$C(=NR^6)NR^4R^5$, —$NR^4C(O)NR^5R^6$, —$NR^4S(O)_pR^5$ or —$C(O)NR^4R^5$, and each hydrogen in $R^2$ is optionally substituted by $R^8$;

each $R^3$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —$S(O)_mR^4$, —$SO_2NR^4R^5$, —$S(O)_2OR^4$, —$NO_2$, —$NR^4R^5$, —$(CR^6R^7)_nOR^4$, —CN, —$C(O)R^4$, —$OC(O)R^4$, —$O(CR^6R^7)_nR^4$, —$NR^4C(O)R^5$, —$(CR^6R^7)_nC(O)OR^4$, —$(CR^6R^7)_nOR^4$, —$(CR^6R^7)_nC(O)NR^4R^5$, —$(CR^6R^7)_nNCR^4R^5$, —$C(=NR^6)NR^4R^5$, —$NR^4C(O)NR^5R^6$, —$NR^4S(O)pR^5$ or —$C(O)NR^4R^5$, each hydrogen in $R^3$ is optionally substituted by $R^8$, and $R^3$ groups on adjacent atoms may combine to form a $C_{6-12}$ aryl, 5-12 membered heteroaryl, $C_{3-12}$ cycloalkyl or 3-12 membered heteroalicyclic group;

each $R^4$, $R^5$, $R^6$ and $R^7$ is independently hydrogen, halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl; or any two of $R^4$, $R^5$, $R^6$ and $R^7$ bound to the same nitrogen atom may, together with the nitrogen to which they are bound, be combined to form a 3 to 12 membered heteroalicyclic or 5-12 membered heteroaryl group optionally containing 1 to 3 additional heteroatoms selected from N, O, and S; or any two of $R^4$, $R^5$, $R^6$ and $R^7$ bound to the same carbon atom may be combined to form a $C_{3-12}$ cycloalkyl, $C_{6-12}$ aryl, 3-12 membered heteroalicyclic or 5-12 membered heteroaryl group; and each hydrogen in $R^4$, $R^5$, $R^6$ and $R^7$ is optionally substituted by $R^8$;

each $R^8$ is independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —$NH_2$, —CN, —OH, —O—$C_{1-12}$ alkyl, —O—$(CH_2)_nC_{3-12}$ cycloalkyl, —O—$(CH_2)_nC_{6-12}$ aryl, —O—$(CH_2)_n$(3-12 membered heteroalicyclic) or —O—$(CH_2)_n$(5-12 membered heteroaryl); and each hydrogen in $R^8$ is optionally substituted by $R^9$;

each $R^9$ is independently halogen, $C_{1-12}$ alkyl, $C_{1-12}$ alkoxy, $C_{3-12}$ cycloalkyl, $C_{6-12}$ aryl, 3-12 membered heteroalicyclic, 5-12 membered heteroaryl, —O—$C_{1-12}$ alkyl, —O—$(CH_2)_nC_{3-12}$ cycloalkyl, —O—$(CH_2)_nC_{6-12}$ aryl, —O—$(CH_2)_n$(3-12 membered heteroalicyclic), —O—$(CH_2)_n$(5-12 membered heteroaryl) or —CN, and each hydrogen in $R^9$ is optionally substituted by halogen, —OH, —CN, —$C_{1-12}$ alkyl which may be partially or fully halogenated, —O—$C_{1-12}$ alkyl which may be partially or fully halogenated, —CO, —SO or —$SO_2$;

$R^{10}$ represents one, two or three optional substituents independently halogen, $C_{1-12}$ alkyl, $C_{2-12}$ alkenyl, $C_{2-12}$ alkynyl, $C_{3-12}$ cycloalkyl, $C_{6-12}$ aryl, 3-12 membered heteroalicyclic, 5-12 membered heteroaryl, —$S(O)_mR^4$, —$SO_2NR^4R^5$, —$S(O)_2OR^4$, —$NO_2$, —$NR^4R^5$, —$(CR^6R^7)_nOR^4$, —CN, —$C(O)R^4$, —$OC(O)R^4$, —$O(CR^6R^7)_nR^4$, —$NR^4C(O)R^5$, —$(CR^6R^7)_nC(O)OR^4$, —$(CR^6R^7)_nOR^4$, —$(CR^6R^7)_nC(O)NR^4R^5$, —$(CR^6R^7)_nNCR^4R^5$, —$C(=NR^6)NR^4R^5$, —$NR^4C(O)NR^5R^6$, —$NR^4S(O)_pR^5$, —$C(O)NR^4R^5$, —$(CR^6R^7)_n$(3-12 membered heteroalicyclic), —$(CR^6R^7)_n$($C_{3-12}$ cycloalkyl), —$(CR^6R^7)_n$($C_{6-12}$ aryl), —$(CR^6R^7)_n$(5-12 membered heteroaryl), or —$(CR^6R^7)_nC(O)NR^4R^5$, and each hydrogen in $R^{10}$ is optionally substituted by $R^3$;

wherein each m is independently 0, 1 or 2; each n is independently 0, 1, 2, 3 or 4; and each p is independently 1 or 2. Descriptions of the various substituents as well as specific compounds encompassed by formula (VIII) are described in WO2006021886.

Accordingly, in a method for producing the compound of structural formula (VIII), a step in the method can comprise reducing or converting a compound of formula (I) to the compound of formula (II) using the ketoreductase polypeptides described herein under reaction conditions suitable for reducing or converting the substrate compound of formula (I) to the product compound of formula (II). Synthesis of the compounds of formula (VIII) from the compound of formula (II) are described in the cited reference.

As is known by those of skill in the art, ketoreductase-catalyzed reduction reactions typically require a cofactor. Reduction reactions catalyzed by the engineered ketoreductase enzymes described herein also typically require a cofactor, although many embodiments of the engineered ketoreductases require far less cofactor than reactions catalyzed with wild-type ketoreductase enzymes. As used herein, the term "cofactor" refers to a non-protein compound that operates in combination with a ketoreductase enzyme. Cofactors suitable for use with the engineered ketoreductase enzymes described herein include, but are not limited to, $NADP^+$ (nicotinamide adenine dinucleotide phosphate), NADPH (the reduced form of $NADP^+$), $NAD^+$ (nicotinamide adenine dinucleotide) and NADH (the reduced form of $NAD^+$). Generally, the reduced form of the cofactor is added to the reaction mixture. The reduced NAD(P)H form can be optionally regenerated from the oxidized $NAD(P)^+$ form using a cofactor regeneration system.

The term "cofactor regeneration system" refers to a set of reactants that participate in a reaction that reduces the oxidized form of the cofactor (e.g., $NADP^+$ to NADPH). Cofactors oxidized by the ketoreductase-catalyzed reduction of the keto substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst, that catalyzes the reduction of the oxidized form of the cofactor by the reductant. Cofactor regeneration systems to regenerate NADH or NADPH from $NAD^+$ or $NADP^+$, respectively, are known in the art and may be used in the methods described herein.

Suitable exemplary cofactor regeneration systems that may be employed include, but are not limited to, glucose and glucose dehydrogenase, formate and formate dehydrogenase, glucose-6-phosphate and glucose-6-phosphate dehydrogenase, a secondary (e.g., isopropanol) alcohol and secondary alcohol dehydrogenase, phosphite and phosphite dehydrogenase, molecular hydrogen and hydrogenase, and the like. These systems may be used in combination with either $NADP^+$/NADPH or $NAD^+$/NADH as the cofactor. Electrochemical regeneration using hydrogenase may also be used as a cofactor regeneration system. See, e.g., U.S. Pat. Nos. 5,538,867 and 6,495,023, both of which are incorporated herein by reference. Chemical cofactor regeneration systems comprising a metal catalyst and a reducing agent (for example, molecular hydrogen or formate) are also suitable. See, e.g., PCT publication WO 2000/053731, which is incorporated herein by reference.

The terms "glucose dehydrogenase" and "GDH" are used interchangeably herein to refer to an $NAD^+$ or $NADP^+$-dependent enzyme that catalyzes the conversion of D-glucose and NAD or NADP to gluconic acid and NADH or NADPH, respectively. Equation (1), below, describes the glucose dehydrogenase-catalyzed reduction of $NAD^+$ or $NADP^+$ by glucose.

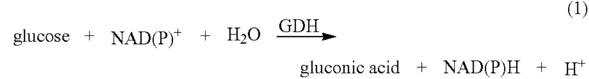

$$\text{glucose} + NAD(P)^+ + H_2O \xrightarrow{GDH} \text{gluconic acid} + NAD(P)H + H^+ \quad (1)$$

Glucose dehydrogenases that are suitable for use in the practice of the methods described herein include both naturally occurring glucose dehydrogenases, as well as non-naturally occurring glucose dehydrogenases. Naturally occurring glucose dehydrogenase encoding genes have been reported in the literature. For example, the *Bacillus subtilis* 61297 GDH gene was expressed in *E. coli* and was reported to exhibit the same physicochemical properties as the enzyme produced in its native host (Vasantha et al., 1983, *Proc. Natl. Acad. Sci. USA* 80:785). The gene sequence of the *B. subtilis* GDH gene, which corresponds to Genbank Acc. No. M12276, was reported by Lampel et al., 1986, *J. Bacteriol.* 166:238-243, and in corrected form by Yamane et al., 1996, *Microbiology* 142:3047-3056 as Genbank Acc. No. D50453. Naturally occurring GDH genes also include those that encode the GDH from *B. cereus* ATCC 14579 (*Nature,* 2003, 423:87-91; Genbank Acc. No. AE017013) and *B. megaterium* (Eur. J. Biochem., 1988, 174:485-490, Genbank Acc. No. X12370; *J. Ferment. Bioeng.,* 1990, 70:363-369, Genbank Acc. No. GI216270). Glucose dehydrogenases from *Bacillus* sp. are provided in PCT publication WO 2005/018579 as SEQ ID NOS: 10 and 12 (encoded by polynucleotide sequences corresponding to SEQ ID NOS: 9 and 11, respectively, of the PCT publication), the disclosure of which is incorporated herein by reference.

Non-naturally occurring glucose dehydrogenases may be generated using known methods, such as, for example, mutagenesis, directed evolution, and the like. GDH enzymes having suitable activity, whether naturally occurring or non-naturally occurring, may be readily identified using the assay described in Example 4 of PCT publication WO 2005/018579, the disclosure of which is incorporated herein by reference. Exemplary non-naturally occurring glucose dehydrogenases are provided in PCT publication WO 2005/018579 as SEQ ID NOS: 62, 64, 66, 68, 122, 124, and 126. The polynucleotide sequences that encode them are provided in PCT publication WO 2005/018579 as SEQ ID NOS: 61, 63, 65, 67, 121, 123, and 125, respectively. All of these sequences are incorporated herein by reference. Additional non-naturally occurring glucose dehydrogenases that are suitable for use in the ketoreductase-catalyzed reduction reactions disclosed herein are provided in U.S. application publication Nos. 2005/0095619 and 2005/0153417, the disclosures of which are incorporated herein by reference.

Glucose dehydrogenases employed in the ketoreductase-catalyzed reduction reactions described herein may exhibit an activity of at least about 10 μmol/min/mg and sometimes at least about $10^2$ μmol/min/mg or about $10^3$ μmol/min/mg, up to about $10^4$ μmol/min/mg or higher in the assay described in Example 4 of PCT publication WO 2005/018579.

The ketoreductase-catalyzed reduction reactions described herein are generally carried out in a solvent. Suitable solvents include water, organic solvents (e.g., ethyl acetate, butyl acetate, 1-octanol, heptane, octane, methyl t-butyl ether (MTBE), toluene, and the like), ionic liquids (e.g., 1-ethyl 4-methylimidazolium tetrafluoroborate, 1-butyl-3-methylimidazolium tetrafluoroborate, 1-butyl-3-methylimidazolium hexafluorophosphate, and the like). In some embodiments, aqueous solvents, including water and aqueous co-solvent systems, are used.

Exemplary aqueous co-solvent systems have water and one or more organic solvent. In general, an organic solvent component of an aqueous co-solvent system is selected such that it does not completely inactivate the ketoreductase enzyme. Appropriate co-solvent systems can be readily identified by measuring the enzymatic activity of the specified engineered ketoreductase enzyme with a defined substrate of interest in the candidate solvent system, utilizing an enzyme activity assay, such as those described herein.

The organic solvent component of an aqueous co-solvent system may be miscible with the aqueous component, providing a single liquid phase, or may be partly miscible or immiscible with the aqueous component, providing two liquid phases. Generally, when an aqueous co-solvent system is employed, it is selected to be biphasic, with water dispersed in an organic solvent, or vice-versa. Generally, when an aqueous co-solvent system is utilized, it is desirable to select an organic solvent that can be readily separated from the aqueous phase. In general, the ratio of water to organic solvent in the co-solvent system is typically in the range of from about 90:10 to about 10:90 (v/v) organic solvent to water, and between 80:20 and 20:80 (v/v) organic solvent to water. The co-solvent system may be pre-formed prior to addition to the reaction mixture, or it may be formed in situ in the reaction vessel.

The aqueous solvent (water or aqueous co-solvent system) may be pH-buffered or unbuffered. Generally, the reduction can be carried out at a pH of about 10 or below, usually in the range of from about 5 to about 10. In some embodiments, the reduction is carried out at a pH of about 9 or below, usually in the range of from about 5 to about 9. In some embodiments, the reduction is carried out at a pH of about 8 or below, often in the range of from about 5 to about 8, and usually in the range of from about 6 to about 8. The reduction may also be carried out at a pH of about 7.8 or below, or 7.5 or below. Alternatively, the reduction may be carried out a neutral pH, i.e., about 7.

During the course of the reduction reactions, the pH of the reaction mixture may change. The pH of the reaction mixture may be maintained at a desired pH or within a desired pH range by the addition of an acid or a base during the course of the reaction. Alternatively, the pH may be controlled by using an aqueous solvent that comprises a buffer. Suitable buffers to maintain desired pH ranges are known in the art and include, for example, phosphate buffer, triethanolamine buffer, and the like. Combinations of buffering and acid or base addition may also be used.

When the glucose/glucose dehydrogenase cofactor regeneration system is employed, the co-production of gluconic acid (pKa=3.6), as represented in equation (1) causes the pH of the reaction mixture to drop if the resulting aqueous gluconic acid is not otherwise neutralized. The pH of the reaction mixture may be maintained at the desired level by standard buffering techniques, wherein the buffer neutralizes the gluconic acid up to the buffering capacity provided, or by the addition of a base concurrent with the course of the conversion. Combinations of buffering and base addition may also be used. Suitable buffers to maintain desired pH ranges are described above. Suitable bases for neutralization of gluconic acid are organic bases, for example amines, alkoxides and the like, and inorganic bases, for example, hydroxide salts (e.g., NaOH), carbonate salts (e.g., $NaHCO_3$), bicarbonate salts (e.g., $K_2CO_3$), basic phosphate salts (e.g., $K_2HPO_4$, $Na_3PO_4$), and the like. The addition of a base concurrent with the course of the conversion may be done manually while monitoring the reaction mixture pH or, more conveniently, by using an automatic titrator as a pH stat. A combination of partial buffering capacity and base addition can also be used for process control.

When base addition is employed to neutralize gluconic acid released during a ketoreductase-catalyzed reduction reaction, the progress of the conversion may be monitored by the amount of base added to maintain the pH. Typically, bases added to unbuffered or partially buffered reaction mixtures over the course of the reduction are added in aqueous solutions.

In some embodiments, the co-factor regenerating system can comprises a formate dehydrogenase. The terms "formate dehydrogenase" and "FDH" are used interchangeably herein to refer to an $NAD^+$ or $NADP^+$-dependent enzyme that catalyzes the conversion of formate and $NAD^+$ or $NADP^+$ to carbon dioxide and NADH or NADPH, respectively. Formate dehydrogenases that are suitable for use as cofactor regenerating systems in the ketoreductase-catalyzed reduction reactions described herein include both naturally occurring formate dehydrogenases, as well as non-naturally occurring formate dehydrogenases. Formate dehydrogenases include those corresponding to SEQ ID NOS: 70 (*Pseudomonas* sp.) and 72 (*Candida boidinii*) of PCT publication WO 2005/018579, which are encoded by polynucleotide sequences corresponding to SEQ ID NOS: 69 and 71, respectively, of PCT publication 2005/018579, the disclosures of which are incorporated herein by reference. Formate dehydrogenases employed in the methods described herein, whether naturally occurring or non-naturally occurring, may exhibit an activity of at least about 1 μmol/min/mg, sometimes at least about 10 μmol/min/mg, or at least about $10^2$ μmol/min/mg, up to about $10^3$ μmol/min/mg or higher, and can be readily screened for activity in the assay described in Example 4 of PCT publication WO 2005/018579.

As used herein, the term "formate" refers to formate anion ($HCO_2^-$), formic acid ($HCO_2H$), and mixtures thereof. Formate may be provided in the form of a salt, typically an alkali or ammonium salt (for example, $HCO_2Na$, $KHCO_2NH_4$, and the like), in the form of formic acid, typically aqueous formic acid, or mixtures thereof. Formic acid is a moderate acid. In aqueous solutions within several pH units of its pKa (pKa=3.7 in water) formate is present as both $HCO_2^-$ and $HCO_2H$ in equilibrium concentrations. At pH values above about pH 4, formate is predominantly present as $HCO_2^-$. When formate is provided as formic acid, the reaction mixture is typically buffered or made less acidic by adding a base to provide the desired pH, typically of about pH 5 or above. Suitable bases for neutralization of formic acid include, but are not limited to, organic bases, for example amines, alkoxides and the like, and inorganic bases, for example, hydroxide salts (e.g., NaOH), carbonate salts (e.g., $NaHCO_3$), bicarbonate salts (e.g., $K_2CO_3$), basic phosphate salts (e.g., $K_2HPO_4$, $Na_3PO_4$), and the like.

For pH values above about pH 5, at which formate is predominantly present as $HCO_2^-$, Equation (2) below, describes the formate dehydrogenase-catalyzed reduction of $NAD^+$ or $NADP^+$ by formate.

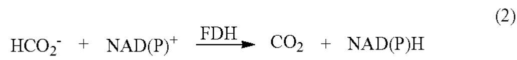

$$HCO_2^- + NAD(P)^+ \xrightarrow{FDH} CO_2 + NAD(P)H \quad (2)$$

When formate and formate dehydrogenase are employed as the cofactor regeneration system, the pH of the reaction mixture may be maintained at the desired level by standard buffering techniques, wherein the buffer releases protons up to the buffering capacity provided, or by the addition of an acid concurrent with the course of the conversion. Suitable acids to add during the course of the reaction to maintain the pH include organic acids, for example carboxylic acids, sulfonic acids, phosphonic acids, and the like, mineral acids, for example hydrohalic acids (such as hydrochloric acid), sulfuric acid, phosphoric acid, and the like, acidic salts, for example dihydrogenphosphate salts (e.g., $KH_2PO_4$), bisulfate salts (e.g., $NaHSO_4$) and the like. Some embodiments utilize formic acid, whereby both the formate concentration and the pH of the solution are maintained.

When acid addition is employed to maintain the pH during a reduction reaction using the formate/formate dehydrogenase cofactor regeneration system, the progress of the conversion may be monitored by the amount of acid added to maintain the pH. Typically, acids added to unbuffered or partially buffered reaction mixtures over the course of conversion are added in aqueous solutions.

The terms "secondary alcohol dehydrogenase" and "sADH" are used interchangeably herein to refer to an $NAD^+$ or $NADP^+$-dependent enzyme that catalyzes the conversion of a secondary alcohol and $NAD^+$ or $NADP^+$ to a ketone and NADH or NADPH, respectively. Equation (3), below, describes the reduction of $NAD^+$ or $NADP^+$ by a secondary alcohol, illustrated by isopropanol.

(3)

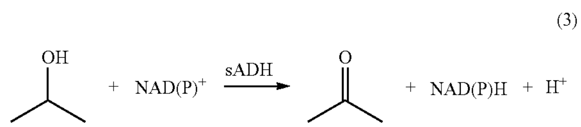

Secondary alcohol dehydrogenases that are suitable for use as cofactor regenerating systems in the ketoreductase-catalyzed reduction reactions described herein include both naturally occurring secondary alcohol dehydrogenases, as well as non-naturally occurring secondary alcohol dehydrogenases. Naturally occurring secondary alcohol dehydrogenases include known alcohol dehydrogenases from, *Thermoanerobium brockii, Rhodococcus etythropolis, Lactobacillus kefir*, and *Lactobacillus brevis*, and non-naturally occurring secondary alcohol dehydrogenases include engineered alcohol dehydrogenases derived therefrom. Secondary alcohol dehydrogenases employed in the methods described herein, whether naturally occurring or non-naturally occurring, may exhibit an activity of at least about 1 μmol/min/mg, sometimes at least about 10 μmol/min/mg, or at least about $10^2$ μmol/min/mg, up to about $10^3$ μmol/min/mg or higher.

Suitable secondary alcohols include lower secondary alkanols and aryl-alkyl carbinols. Examples of lower secondary alcohols include isopropanol, 2-butanol, 3-methyl-2-butanol, 2-pentanol, 3-pentanol, 3,3-dimethyl-2-butanol, and the like. In one embodiment the secondary alcohol is isopropanol. Suitable aryl-akyl carbinols include unsubstituted and substituted 1-arylethanols.

When a secondary alcohol and secondary alcohol dehydrogenase are employed as the cofactor regeneration system, the resulting NAD or NADP is reduced by the coupled oxidation of the secondary alcohol to the ketone by the secondary alcohol dehydrogenase. Some engineered ketoreductases also have activity to dehydrogenate a secondary alcohol reductant. In some embodiments using secondary alcohol as reductant, the engineered ketoreductase and the secondary alcohol dehydrogenase are the same enzyme.

In carrying out embodiments of the ketoreductase-catalyzed reduction reactions described herein employing a cofactor regeneration system, either the oxidized or reduced form of the cofactor may be provided initially. As described above, the cofactor regeneration system converts oxidized cofactor to its reduced form, which is then utilized in the reduction of the ketoreductase substrate.

In some embodiments, cofactor regeneration systems are not used. For reduction reactions carried out without the use of a cofactor regenerating systems, the cofactor is added to the reaction mixture in reduced form.

In some embodiments, when the process is carried out using whole cells of the host organism, the whole cell may natively provide the cofactor. Alternatively or in combination, the cell may natively or recombinantly provide the glucose dehydrogenase.

In carrying out the stereoselective reduction reactions described herein, the engineered ketoreductase enzyme, and any enzymes comprising the optional cofactor regeneration system, may be added to the reaction mixture in the form of the purified enzymes, whole cells transformed with gene(s) encoding the enzymes, and/or cell extracts and/or lysates of such cells. The gene(s) encoding the engineered ketoreductase enzyme and the optional cofactor regeneration enzymes can be transformed into host cells separately or together into the same host cell. For example, in some embodiments one set of host cells can be transformed with gene(s) encoding the engineered ketoreductase enzyme and another set can be transformed with gene(s) encoding the cofactor regeneration enzymes. Both sets of transformed cells can be utilized together in the reaction mixture in the form of whole cells, or in the form of lysates or extracts derived therefrom. In other embodiments, a host cell can be transformed with gene(s) encoding both the engineered ketoreductase enzyme and the cofactor regeneration enzymes.

Whole cells transformed with gene(s) encoding the engineered ketoreductase enzyme and/or the optional cofactor regeneration enzymes, or cell extracts and/or lysates thereof, may be employed in a variety of different forms, including solid (e.g., lyophilized, spray-dried, and the like) or semisolid (e.g., a crude paste).

The cell extracts or cell lysates may be partially purified by precipitation (ammonium sulfate, polyethyleneimine, heat treatment or the like, followed by a desalting procedure prior to lyophilization (e.g., ultrafiltration, dialysis, and the like). Any of the cell preparations may be stabilized by crosslinking using known crosslinking agents, such as, for example, glutaraldehyde or immobilization to a solid phase (e.g., Eupergit C, and the like).

The solid reactants (e.g., enzyme, salts, etc.) may be provided to the reaction in a variety of different forms, including powder (e.g., lyophilized, spray dried, and the like), solution, emulsion, suspension, and the like. The reactants can be readily lyophilized or spray dried using methods and equipment that are known to those having ordinary skill in the art. For example, the protein solution can be frozen at −80° C. in small aliquots, then added to a prechilled lyophilization chamber, followed by the application of a vacuum. After the removal of water from the samples, the temperature is typically raised to 4° C. for two hours before release of the vacuum and retrieval of the lyophilized samples.

The quantities of reactants used in the reduction reaction will generally vary depending on the quantities of product desired, and concomitantly the amount of ketoreductase substrate employed. The following guidelines can be used to determine the amounts of ketoreductase, cofactor, and optional cofactor regeneration system to use. Generally, keto substrates can be employed at a concentration of about 20 to 300 grams/liter using from about 50 mg to about 5 g of ketoreductase and about 10 mg to about 150 mg of cofactor. Those having ordinary skill in the art will readily understand how to vary these quantities to tailor them to the desired level of productivity and scale of production. Appropriate quantities of optional cofactor regeneration system may be readily determined by routine experimentation based on the amount of cofactor and/or ketoreductase utilized. In general, the reductant (e.g., glucose, formate, isopropanol) is utilized at levels above the equimolar level of ketoreductase substrate to achieve essentially complete or near complete conversion of the ketoreductase substrate.

The order of addition of reactants is not critical. The reactants may be added together at the same time to a solvent (e.g., monophasic solvent, biphasic aqueous co-solvent system, and the like), or alternatively, some of the reactants may be added separately, and some together at different time points. For example, the cofactor regeneration system, cofactor, ketoreductase, and ketoreductase substrate may be added first to the solvent.

For improved mixing efficiency when an aqueous co-solvent system is used, the cofactor regeneration system, ketoreductase, and cofactor may be added and mixed into the aqueous phase first. The organic phase may then be added and mixed in, followed by addition of the ketoreductase substrate. Alternatively, the ketoreductase substrate may be premixed in the organic phase, prior to addition to the aqueous phase Suitable conditions for carrying out the ketoreductase-catalyzed reduction reactions described herein include a wide variety of conditions which can be readily optimized by routine experimentation that includes, but is not limited to, contacting the engineered ketoreductase enzyme and substrate at an experimental pH and temperature and detecting product, for example, using the methods described in the Examples provided herein.

The ketoreductase catalyzed reduction is typically carried out at a temperature in the range of from about 15° C. to about 75° C. For some embodiments, the reaction is carried out at a temperature in the range of from about 20° C. to about 55° C. In still other embodiments, it is carried out at a temperature in the range of from about 20° C. to about 45° C. The reaction may also be carried out under ambient conditions.

The reduction reaction is generally allowed to proceed until essentially complete, or near complete, reduction of substrate is obtained. Reduction of substrate to product can be monitored using known methods by detecting substrate and/or product. Suitable methods include gas chromatography, HPLC, and the like. Conversion yields of the alcohol reduction product generated in the reaction mixture are generally greater than about 50%, may also be greater than about 60%, may also be greater than about 70%, may also be greater than about 80%, may also be greater than 90%, and are often greater than about 97%.

7. EXAMPLES

Various features and embodiments of the disclosure are illustrated in the following representative examples, which are intended to be illustrative, and not limiting, In the following descriptions, wherever glucose dehydrogenase (GDH) is used, it is GDH CDX901, obtainable from Julich Chiral Solutions, Jülich, Germany.

7.1 Example 1: Wild-type Ketoreductase Gene Acquisition and Construction of Expression Vectors Ketoreductase (KRED) encoding genes were designed for expression in *E. coli* based on the reported amino acid sequence of the ketoreductase and a codon optimization algorithm as described in Example 1 of U.S. provisional application Ser. No. 60/848,950 and WO2008042876, incorporated herein by reference. Genes were synthesized using oligonucleotides composed of 42 nucleotides and cloned into expression vector pCK110900 (depicted as FIG. 3 in United States Patent Application Publication 20060195947) under the control of a lac promoter. The expression vector also contained the P15a origin of replication and the chloramphenicol resistance gene. Resulting plasmids were transformed into *E. coli* W3110 using standard methods. Codon optimized genes and the encoding polypeptides as well are listed in Table 3. The activity of the wild-type ketoreductases was confirmed as described in U.S. provisional application Ser. No. 60/848,950.

TABLE 3

Abbreviations, source and references for Ketoreductases used

| Keto-reductase abbreviation | Microorganism from which enzyme was originally identified | Genbank Acc. No. | GI no. | Polynucleotide SEQ ID NO. | Polypeptide SEQ ID NO, or Source |
|---|---|---|---|---|---|
| ADH-CM | *Candida magnoliae* | AB036927.1 | 12657576 | SEQ ID No 1 in US Application Publication 20060195947 | SEQ ID No 2 in US Application Publication 20060195947 |
| YDL | *Saccharomyces cerevisiae* | NP_010159.1 | 6320079 | SEQ ID NO: 109 | SEQ ID NO: 110 |
| ADH-LB | *Lactobacillus brevis* | 1NXQ_A | 30749782 | SEQ ID NO: 1 | SEQ ID NO: 2 |
| ADH-RE | *Rhodococcus erythropolis* | AAN73270.1 | 34776951 | SEQ ID NO: 111 | SEQ ID NO112 |
| YGL | *Saccharomyces cerevisiae* | NP_011476 | 6321399 | SEQ ID NO: 113 | SEQ ID NO: 114 |
| YPR | *Saccharomyces cerevisiae* | NP_010656.1 | 6320576 | SEQ ID NO: 115 | SEQ ID NO: 116 |
| GRE | *Saccharomyces cerevisiae* | NP_014490.1 | 6324421 | SEQ ID NO: 117 | SEQ ID NO: 118 |
| ADH-LK | *Lactobacillus kefir* | AAP94029.1 | 33112056 | SEQ ID N: 3 | SEQ ID NO: 4 |
| ADH-SB | *Sporobolomyces salmonicolor* | Q9UUN9 | 30315955 | SEQ ID No 103 | SEQ ID No 104 |
| ADH-SC | *Streptomyces coelicolor* | NP_631415.1 | 21225636 | SEQ ID No 101 | SEQ ID No 102 |
| ADH-TB | *Thermoanaerobium brockii* | X64841.1 | 1771790 | SEQ ID No 107 | SEQ ID No 108 |

TABLE 3-continued

Abbreviations, source and references for Ketoreductases used

| Keto-reductase abbreviation | Microorganism from which enzyme was originally identified | Genbank Acc. No. | GI no. | Polynucleotide SEQ ID NO. | Polypeptide SEQ ID NO, or Source |
|---|---|---|---|---|---|
| ADH-HE | Horse liver | DEHOAL | 625197 | SEQ ID No 105 | SEQ ID NO 106 |
| ADH-CP | *Candida parapsilosis* | BAA24528 | 2815409 | | Julich Chiral Solutions Cat. No. 03.11 |
| DR-LB | *Lactobacillus brevis* diacetyl reductase | ABJ63353.1 | 116098204 | | Julich Chiral Solutions Cat. No. 8.1 |
| ADH-CB | *Candida boidinii* | CAD66648 | 28400789 | | Julich Chiral Solutions Cat. No. 02.10 |
| LDH-LL | *Lactobacillus leichmannii* | | | | Fluka Cat. No. 61306 |

Polynucleotides encoding engineered ketoreductases of the present disclosure were likewise cloned into vector pCK110900 for expression in *E. coli* W3110.

7.2 Example 2: Production of Ketoreductase Powders; Shake Flask Procedure

A single microbial colony of *E. coli* containing a plasmid with the ketoreductase gene of interest was inoculated into 50 ml Luria Bertani broth containing 30 μg/ml chloramphenicol and 1% glucose. Cells were grown overnight (at least 16 hrs) in an incubator at 30° C. with shaking at 250 rpm. The culture was diluted into 250 ml Terrific Broth (12 g/L bacto-tryptone, 24 g/L yeast extract, 4 ml/L glycerol, 65 min potassium phosphate, pH 7.0, 1 min $MgSO_4$, 30 μg/ml chloramphenicol) in 1 liter flask) to an optical density at 600 nm (OD600) of 0.2 and allowed to grow at 30° C. Expression of the ketoreductase gene was induced with 1 min IPTG when the OD600 of the culture is 0.6 to 0.8 and incubated overnight (at least 16 hrs). Cells were harvested by centrifugation (5000 rpm, 15 min, 4° C.) and the supernatant discarded. The cell pellet was resuspended with an equal volume of cold (4° C.) 100 min triethanolamine (chloride) buffer, pH 7.0 (including 2 min $MgSO_4$ in the case of ADH-LK and ADH-LB and engineered ketoreductases derived therefrom), and harvested by centrifugation as above. The washed cells were resuspended in two volumes of the cold triethanolamine (chloride) buffer and passed through a French Press twice at 12000 psi while maintained at 4° C. Cell debris was removed by centrifugation (9000 rpm, 45 min., 4° C.). The clear lysate supernatant was collected and stored at −20° C. Lyophilization of frozen clear lysate provided a dry powder of crude ketoreductase enzyme.

7.3 Example 3: Production of Ketoreductases; Fermentation Procedure

In an aerated agitated 15 L fermenter, 6.0 L of growth medium containing 0.88 g/L ammonium sulfate, 0.98 g/L of sodium citrate; 12.5 g/L of dipotassium hydrogen phosphate trihydrate, 6.25 g/L of potassium dihydrogen phosphate, 6.2 g/L of Tastone-154 yeast extract, 0.083 g/L ferric ammonium citrate, and 8.3 ml/L of a trace element solution containing 2 g/L of calcium chloride dihydrate, 2.2 g/L of zinc sulfate septahydrate, 0.5 g/L manganese sulfate monohydrate, 1 g/L cuprous sulfate heptahydrate, 0.1 g/L ammonium molybdate tetrahydrate and 0.02 g/L sodium tetraborate decahydrate was brought to a temperature of 30° C. The fermenter was inoculated with a late exponential culture of *E. coli* W3110, containing a plasmid with the ketoreductase gene of interest, grown in a shake flask as described in Example 3 to a starting OD600 of 0.5 to 2.0. The fermenter was agitated at 500-1500 rpm and air was supplied to the fermentation vessel at 1.0-15.0 L/min to maintain dissolved oxygen level of 30% saturation or greater. The pH of the culture was controlled at 7.0 by addition of 20% v/v ammonium hydroxide. Growth of the culture was maintained by the addition of a feed solution containing 500 g/L cerelose, 12 g/L ammonium chloride and 10.4 g/L magnesium sulfate heptahydrate. After the culture reached an OD600 of 50, the expression of ketoreductase was induced by the addition of isopropyl-b-D-thiogalactoside (IPTG) to a final concentration of 1 min. The culture was grown for another 14 hours. The culture was then chilled to 4° C. and maintained at 4° C. until harvested. Cells were harvested by centrifugation at 5000 G for 40 minutes in a Sorval RC12BP centrifuge at 4° C. Harvested cells were used directly in the following downstream recovery process or were stored at 4° C. until such use.

The cell pellet was resuspended in 2 volumes of 100 min triethanolamine (chloride) buffer, pH 6.8, at 4° C. to each volume of wet cell paste. The intracellular ketoreductase was released from the cells by passing the suspension through a homogenizer fitted with a two-stage homogenizing valve assembly using a pressure of 12000 psig. The cell homogenate was cooled to 4° C. immediately after disruption. A solution of 10% w/v polyethyleneimine, pH 7.2, was added to the lysate to a final concentration of 0.5% w/v and stirred for 30 minutes. The resulting suspension was clarified by centrifugation at 5000 G in a standard laboratory centrifuge for 30 minutes. The clear supernatant was decanted and concentrated ten fold using a cellulose ultrafiltration membrane with a molecular weight cut off of 30 Kd. The final concentrate was dispensed into shallow containers, frozen at −20° C. and lyophilized to powder. The ketoreductase powder was stored at −80° C.

7.4 Example 4: Analytical Methods to Determine Conversion and Enantiomeric Excess of 2',6'-dichloro-3'-fluoroacetophenone to (5)-1-[2',6'-dichloro-3'-fluorophenyl]-ethanol Reduction of 2',6'-dichloro-3'-fluoroacetophenone and chiral purity of the alcohol product was determined by Reverse Phase Chiral HPLC (4.6×150 mm Chiralpak AD-RH column (no guard cartridge); 50:50 ACN/$H_2O$ at 0.8 mL/min; 25° C.; detection at 254 nm with the following retention times: (S)-alcohol 5.77 min.; (R)-alcohol 6.19 min; ketone 7.49 min) or Normal Phase Chiral HPLC (4.6×250 mm Chiralpak AD column (no guard cartridge); 2:98 IPA/Hexane at 2.5 mL/min at room temperature (not regulated); detection at 220 nm with the following retention times: (S)-alcohol 4.72 min.; (R)-alcohol 5.30 min; ketone 2.03 min).

Alternatively, the following gas chromatographic analytical methods were used: an achiral method using an HP-5 column (30 m×0.25 mm) with a temperature program of 100° C. (1 min) to 200° C. (4 min) at 50° C./min (retention times were 4.33 min for the ketone and 4.70 min for the alcohol) and a chiral method using a Beta Cyclodextrin (DM) column (30 m×0.25 mm) at 165° C. isothermal (retention times were 3.42 min for the ketone, 5.92 min for the R-isomer and 6.25 min for the S-isomer).

7.5 Example 5: Evaluation of Wild-Type Ketoreductases for Reduction of 2',6'-dichloro-3'-fluoroacetophenone KREDs described in Table 3 of Example 1 were screened using stoichiometric NADH or NADPH as co-factors. To each well of a 96-deep-well plate was added 5-10 mg of KRED, 20 mg of NAD(P)H in 500 μL of 100 min pH 7.0 triethanolamine(chloride) buffer and 15 μL of the substrate (~40 g/L of substrate; conversion limited to ~25 by the co-factor). The plate was sealed and shaken for 6 hours. The reactions were quenched by the addition of 1 mL of EtOAc. The conversion and stereopurity of the product were assayed as described in Example 4.

Under these conditions, YDL, YGL, GRE, ADH-RE, ADH-SB, ADH-SC, ADH-HL, LDH-LL, ADH-CP, ADH-CB, and DR-LB gave no detectable conversion with either NADPH or NADH, whereas ADH-LB, and YPR gave <0.5% conversion. ADH-LK converted <1% of the substrate to the chiral alcohol This example demonstrates that wild-type ketoreductases have very little if any activity on 2',6'-dichloro-3'-fluoroacetophenone.

7.6 Example 6: Evaluation of ADH-LK Variants for Reduction of 2',6'-dichloro-3'-fluoroacetophenone Several ADH-LK variants that had been generated as described in U.S. application Ser. No. 60/957,974, filed Aug. 24, 2007 and U.S. application Ser. No. 12/197,286, filed Aug. 24, 2008 converted >0.5% of the substrate to the chiral alcohol when evaluated under the conditions described in Example 5 and as listed in Table 4.

TABLE 4

| SEQ ID NO.[c] | Conversion[a] | Enantiomeric excess[b] |
|---|---|---|
| 4 | 0 | 0 |
| 115 | + | + |
| 117 | + | ++ |
| 111 | + | ++ |
| 119 | ++ | ++ |
| 121 | ++ | ++ |
| 113 | ++ | ++ |
| 6 | ++ | ++ |

[a]0: 0.5-1% conversion: +: 1-20% conversion; ++ >20% conversion

[b]0: <90% e.e. (S-enantiomer); +: 90-99% e.e. (S-enantiomer); ++ >99% e.e. (S-enantiomer).

[c]refers to SEQ ID NOs in U.S. application Ser. No. 60/957,974 and 12/197,286.

This example illustrates that ADH-LK variants in which the tyrosine residue at position 190 is altered to phenylalanine, proline, cysteine or alanine reduced 2',6'-dichloro-3'-fluoroacetophenone to the corresponding S-alcohol.

7.7 Example 7: High Throughput NADPH Fluorescence Prescreen to Identify Enzymes that Reduce 2',6'-dichloro-3'-fluoroacetophenone Plasmid libraries obtained by directed evolution and containing evolved ketoreductase genes were transformed into *E. coli* W3110 and plated on Luria-Bertani (LB) agar medium containing 1% glucose and 30 μg/mL chloramphenicol (CAM). After incubation for at least 16 hrs at 30° C., colonies were picked using a Q-bot® robotic colony picker (Genetix USA, Inc., Beaverton, Oreg.) into 96-well shallow well microtiter plates containing 180 μL Terrific broth (TB), 1% glucose and 30 μg/mL chloramphenicol (CAM). Cells were grown overnight at 30° C. with shaking at 200 rpm. 5 μL of this culture was then transferred into 96-deep well plates containing 380 μL Terrific broth (TB), 1 min $MgSO_4$ and 30 μg/mL CAM. After incubation of deep-well plates at 30° C. with shaking at 250 rpm for 2.5 to 3 hours ($OD_{600}$ 0.6-0.8), recombinant gene expression by the cell cultures was induced by isopropyl thiogalactoside (IPTG) to a final concentration of 1 min. The plates were then incubated at 30° C. with shaking at 250 rpm for 15-17 hrs.

Cells were pelleted via centrifugation, resuspended in 300 μL lysis buffer and lysed by shaking at room temperature for at least 1 hour. The lysis buffer contained 100 min triethanolamine (chloride) buffer, pH 7.0-7.2, 1 mg/mL lysozyme and 750 μg/mL polymixin B sulfate. The plates are then spun in the centrifuge at 4000 RPM for 20 minutes at 4° C., and the clear supernatant (lysate) analyzed in the fluorescent assay.

In 96-well black microtiter plates 20 μl of each lysate (pretreated for 0-24 hrs at 40-50° C., diluted in 100 min triethanolamine(chloride) buffer, pH 7.0, 1 min $MgSO_4$ if necessary) was added to 180 μl of an assay mixture consisting of 100 min triethanolamine(chloride) buffer, pH 7.0, 1 min $MgSO_4$, 0.2 g/L NADPH, 100-600 min glucose, 600-900 min sodium gluconate and 0.2 g/L 2',6'-dichloro-3'-fluoroacetophenone and reaction progress measured by following the decrease in fluorescence of NADPH at 445 nm after excitation at 330 nm in a Flexstation (Molecular Devices, USA).

This example describes the method that was used to identify KRED variants improved for the rate of 2',6'-dichloro-3'-fluoroacetophenone reduction.

7.8 Example 8: Reduction of 2',6'-dichloro-3'-fluoroacetophenone by Engineered Ketoreductases Derived from ADH-LK Improved ADH-LK variants for the reduction of 2',6'-dichloro-3'-fluoroacetophenone to (5)-1-[2',6'-dichloro-3'-fluorophenyl]-ethanol were analyzed in small scale chemical reactions. To a 100 mL three-neck vessel equipped with a PTFE-coated magnetic stirring bar and a pH electrode connected to an automatic titrator for pH-controlled addition of base on-demand via a feeding tube into the vessel, was charged 30 ml 100 min triethanolamine(chloride) buffer (pH 7), 2 min $MgSO_4$), 200 mg KRED with SEQ ID NO. as described in the table below, 50 mg GDH, 15 mg NADP-Na, 3.13 g glucose, 6 g 2',6'-dichloro-3'-fluoroacetophenone (200 g/L) at 25° C. The automatic titrator maintained the pH at 7 by the addition of 4N NaOH, which was continuously recorded. Reaction progress was monitored by the rate and cumulative addition of the base and periodic sampling of the reaction mixture for extraction with ethylacetate and analysis by the method of Example 4.

Table 5 gives the SEQ ID NO. corresponding to the ketoreductase, the number of amino acid mutations from the wild-type ADH-LK and the conversion of 2',6'-dichloro-3'-fluoroacetophenone to (S)-1-[2',6'-dichloro-3'-fluorophenyl]-ethanol. The stereopurity of the S-alcohol was always >99.9%.

TABLE 5

Activity and stability of ADH-LK Variants

| SEQ ID NO. | No. of mutations from ADH-LK | activity | stability |
|---|---|---|---|
| 4 | 0 | – | |
| 6 | 1 | + | |
| 8 | 2 | ++ | + |
| 10 | 2 | ++ | |
| 12 | 2 | + | |
| 14 | 2 | ++ | |
| 16 | 2 | ++ | + |
| 48 | 2 | + | |
| 50 | 2 | + | |
| 52 | 3 | + | |
| 20 | 3 | + | + |
| 18 | 4 | +++ | + |
| 36 | 3 | +++ | |
| 54 | 3 | ++ | + |
| 56 | 3 | ++ | |
| 62 | 3 | ++ | |
| 64 | 3 | ++ | |
| 58 | 3 | ++ | |
| 60 | 2 | ++ | |
| 22 | 3 | ++ | ++ |
| 66 | 3 | ++ | + |
| 68 | 3 | ++ | ++ |
| 70 | 4 | ++ | ++ |
| 72 | 3 | ++ | ++ |
| 32 | 3 | +++ | + |
| 28 | 3 | ++ | + |
| 30 | 3 | ++ | + |
| 34 | 4 | +++ | + |
| 74 | 4 | +++ | + |
| 38 | 4 | +++ | ++ |
| 40 | 5 | +++ | ++ |
| 76 | 5 | +++ | ++ |
| 78 | 5 | +++ | ++ |
| 80 | 5 | +++ | ++ |
| 82 | 5 | +++ | ++ |
| 84 | 8 | +++ | ++ |
| 42 | 6 | +++ | ++ |
| 44 | 6 | +++ | ++ |
| 86 | 7 | +++ | ++ |
| 46 | 6 | +++ | ++ |
| 88 | 6 | +++ | ++ |
| 90 | 6 | +++ | ++ |
| 92 | 6 | +++ | ++ |
| 94 | 6 | +++ | ++ |

a. –: no activity; +: 100-450% the activity of SEQ ID No. 6; ++: 450-1500% the activity of SEQ ID No. 6; +++: >1500% the activity of SEQ ID No. 6.
b. +: measurable activity after 2 hrs at 50° C.; ++: >400% the activity of SEQ ID No. 16 after 2 hrs at 50° C..

This Example illustrates that engineered ketoreductases derived from the wild-type ketoreductase ADH-LK provide improved activity compared to ketoreductase ADH-LK.

7.9 Example 9: Reduction of 2',6'-dichloro-3'-fluoroacetophenone by Engineered Ketoreductases Derived from ADH-LB Improved ADH-LB variants for the reduction of 2',6'-dichloro-3'-fluoroacetophenone to (5)-1-[2',6'-dichloro-3'-fluorophenyl]-ethanol were analyzed in small scale chemical reactions as described for ADH-LK variants in Example 8. Table 6 gives the SEQ ID NO. corresponding to the ketoreductase, the number of amino acid mutations from the wild-type ADH-LK and the conversion of 2',6'-dichloro-3'-fluoroacetophenone to (S)-1-[2',6'-dichloro-3'-fluorophenyl]-ethanol. The stereopurity of the S-alcohol was always >99.9%.

TABLE 6

Activity and stability of ADH-LK Variants

| SEQ ID NO. | No. of mutations from ADH-LK | activity | stability |
|---|---|---|---|
| 4 | 0 | – | |
| 6 | 1 | + | |
| 8 | 2 | ++ | + |
| 10 | 2 | ++ | |
| 12 | 2 | + | |
| 14 | 2 | ++ | |
| 16 | 2 | ++ | + |
| 48 | 2 | + | |
| 50 | 2 | + | |
| 52 | 3 | + | |
| 20 | 3 | + | + |
| 18 | 4 | +++ | + |

a. –: no activity; +: 100-450% the activity of SEQ ID No. 6; ++: 450-1500% the activity of SEQ ID No. 6; +++: >1500% the activity of SEQ ID No. 6.
b. +: measurable activity after 2 hrs at 50° C.; ++: after 2 hrs at 50° C., >400% the activity SEQ ID No. 16 after 2 hrs at 50° C..

This Example illustrates that engineered ketoreductases derived from the wild-type ketoreductase ADH-LB also provide improved activity compared to ketoreductase ADH-LB.

7.10 Example 10: Preparative Scale Production of (S)-1-[2',6'-dichloro-3'-fluorophenyl]-ethanol To a 500 mL jacketed three neck round bottom flask equipped with an Ace Glass mechanical stirrer (75 mm diameter teflon stirrer blade), and a pH electrode connected to an automatic titrator for pH-controlled addition of base on-demand via a delivery tube into the vessel, was added water (120 mL), triethanolamine (1.8 g) and then hydrochloric acid to adjust the pH to 7.0. Magnesium sulfate was added as a 1M solution (120 μL, 0.12 mmoles, 14.4 mg of $MgSO_4$). The solution was heated to 30° C. with heating fluid circulating through the flask's jacket. Glucose (20 g) was added followed by Na-NADP (120 mg), GDH (0.50 g) and KRED having SEQ ID No. 38 (0.50 g). The pH stat was set to maintain the pH at 7.0±0.1 by the addition of 4N NaOH through the delivery tube. 2',6'-dichloro-3'-fluoroacetophenone (50 g) was added to start the reaction. The electrode required periodic rinsing to remove enzyme derived material. Additional glucose was added in portions as the reaction proceeded: 10 g at 104 min (after 17.5 mL of 4 N NaOH had been added), 5 g at 275 min (after 35.2 mL of 4 N NaOH had been added), 5 g at 379 min (after 42 mL of 4 N NaOH had been added), and 8 g at 488 min (after 47 mL of 4 N NaOH had been added). The reaction was stopped after 24 hr. Heptane (150 mL) was then added and the mixture was heated to 40° C. for 45 min. After cooling to 30° C. the resulting mixture was poured into a separatory funnel and the majority of the bottom aqueous layer was drained. The top layer, a heptane emulsion, was filtered (350 mL, 85 mm diameter coarse filter) through a celite pad under vacuum. The filter was washed with heptane (150 mL) and the filtrate was transferred to a separatory funnel and the two phases were separated. The heptane phase was concentrated on a rotary vacuum evaporator (~50° C., ~150 mmHg increasing to 40 mmHg) to yield (S)-1-[2',6'-dichloro-3'-fluorophenyl]-ethanol as an oil (47.8 g, 94%) which crystallized upon standing.

7.11 Example 11: Reduction of 2',6'-Substituted Acetophenones by Engineered Ketoreductases Derived from ADH-LK Wild-type ADH-LK and an ADH-LK variant improved for the reduction of 2',6'-dichloro-3'-fluoroacetophenone to (S)-1-[2',6'-dichloro-3'-fluorophenyl]-ethanol were tested for activity on two other 2',6'-substituted acetophenones. A solution was prepared of 5 mL 100 min triethanolamine (chloride) buffer (pH 7, 2 min $MgSO_4$), 33 mg KRED having SEQ ID No. 10, 8 mg GDH, 3 mg NADP-Na, and 330 mg glucose. 1 ml of this solution was treated with 0.3 ml 1M (sodium)phosphate buffer pH 7 and 20 mg of the 2',6'-substituted acetophenone at 25° C. Reaction samples (24 hr) were analyzed by the methods of Example 5.

Table 7 gives the conversion of the two 2',6'-substituted acetophenones and the enantiomeric purity of the resulting chiral alcohol by ADH-LK and the ADH-K variant with SEQ ID NO 10.

TABKE 7

Activities of ADH-LK and an ADH-LK variant on two 2',6'-substituted acetophenones.

| | Wild-type ADH-LK (SEQ ID NO. 4) | | Engineered KRED SEQ ID NO. 10 | |
|---|---|---|---|---|
| 2',6'-substituted acetophenone | Conversion (%) | Stereopurity (%) | Conversion (%) | Stereopurity (%) |
| 2',6'-dichloroacetophenone | 0 | – | 88 | >99 S |
| 2',6'-dimethoxyacetophenone | 0 | – | 72 | >99 S |

This example shows that an ADH-LK variant containing the Y190P mutation provides improved activity for 2'6'-substituted acetophenones, and provides the corresponding 2'6'-substituted (S)-1-phenethanol.

7.12 Example 12: Reduction of Unsubstituted Acetophenone by ADH-LK and Engineered Ketoreductases Derived from ADH-LK Containing a Mutation of Y190

To each well of a 96-well plates containing 100 μL cell lysate per well, prepared as in Example 7, was added: 50 μL 7 min $Na\text{-}NADP^+$ in 100 min triethanolamine(chloride) buffer pH 7.0, 300 μL isopropanol, and 50 μL 100 mg/ml acetophenone in THF. The plates were sealed and agitated on an orbital shaker at 850 rpm, room temperature, for 24 h. 1 mL of methyl t-butyl ether (MTBE) was added to each well and the plates were sealed and then shaken at 850 rpm for 10 min at room temperature. The plates were centrifuged at 4,000 rpm (3220×g) for 2 min to separate the phases and 50 μL of the organic phase from each well transferred to a well of a shallow well plate containing 150 μL MTBE. The plates were sealed and analyzed by normal-phase HPLC (Daicel Chiralcel OD-H column (4.6×250 mm) equipped with OD-H guard column; 2.5 μL injection; Mobile Phase: 95:5 v/v Heptane—IPA; Flow-rate: 1.5 mL min-1; Column Temperature: 40° C.; Wavelength: 215 nm). Retention times: acetophenone: 3.5 min; (R)-1-phenylethanol: 5.3 min; (S)-1-phenylethanol: 5.8 min.

Table 8 shows the conversion of the acetophenone and the stereomeric purity of the resulting chiral alcohol by ADH-LK and the ADH-LK variants.

TABLE 8

Activity and Stereoselectivity of ADH-LK Variants on Acetophenone

| SEQ ID NO. | Conversion (%) | Enantiomeric excess (%) | R or S |
|---|---|---|---|
| 4 (wild-type) | 94 | 100 | R |
| 14 | 79 | 46 | S |
| 22 | 80 | 35 | S |
| 28 | 80 | 48 | S |
| 32 | 77 | 50 | S |
| 36 | 89 | 86 | S |
| 42 | 90 | 57 | S |
| 44 | 90 | 41 | S |

This example demonstrates that the wild-type *Lactobacillus* ketoreductase is R-selective on acetophenone and the engineered ketoreductases of the invention, derived therefrom are S-selective on acetophenone.

While various specific embodiments have been illustrated and described, it will be appreciated that various changes can be made without departing from the spirit and scope of the invention(s).

All publications, patents, patent applications and other documents cited in this application are hereby incorporated by reference in their entireties for all purposes to the same extent as if each individual publication, patent, patent application or other document were individually indicated to be incorporated by reference for all purposes.

What is claimed is:

1. An engineered polynucleotide encoding a recombinant ketoreductase polypeptide capable of stereoselectively reducing acetophenone to (S)-1-phenethanol, wherein said polypeptide comprises an amino acid sequence that is at least 95% identical to the reference sequence of SEQ ID NO: 119, wherein said ketoreductase polypeptide is capable of reducing acetophenone to (S)-1-phenethanol at a rate greater than the rate capable by the ketoreductase polypeptide having the sequence of SEQ ID NO: 6.

2. The engineered polynucleotide of claim 1, wherein said engineered polynucleotide encodes a recombinant ketoreductase polypeptide capable of stereoselectively reducing the substrate 2',6'-dichloro-3'-fluoroacetophenone to the product (S)-1-(2,6-dichloro-3-fluorophenyl) ethanol with a percent stereomeric excess of at least 99%.

3. The engineered polynucleotide of claim 1, wherein said engineered polynucleotide encodes a recombinant ketoreductase polypeptide capable of reducing the substrate 2',6'-dichloro-3'-fluoroacetophenone to the product (S)-1-(2,6-dichloro-3-fluorophenyl) ethanol at a rate that is at least 450% greater than the rate capable by the ketoreductase polypeptide having the sequence of SEQ ID NO:6.

4. The engineered polynucleotide of claim 1, wherein said engineered polynucleotide encodes a recombinant ketoreductase polypeptide capable of reducing the substrate 2',6'-dichloro-3'-fluoroacetophenone to the product (S)-1-(2,6-dichloro-3-fluorophenyl) ethanol at a rate that is at least 1500% greater than the rate capable by the ketoreductase polypeptide having the sequence of SEQ ID NO:6.

5. The engineered polynucleotide of claim 1, wherein said engineered polynucleotide encodes a recombinant ketoreductase polypeptide comprising a proline at the position corresponding to position 190 of SEQ ID NO:119.

6. An expression vector comprising the engineered polynucleotide of claim 1.

7. The vector of claim 6, wherein said polynucleotide is operably linked to regulatory sequences suitable for expression of said polynucleotide in a suitable host cell.

8. The vector of claim 7, wherein said host cell is a prokaryotic or eukaryotic cell.

9. The vector of claim 8, wherein said host cell is a prokaryotic cell.

10. The vector of claim 9, wherein said host cell is *E. coli.*

11. A host cell comprising the vector of claim 6.

12. A method for producing at least one recombinant ketoreductase polypeptide comprising culturing the host cell of claim 11 under conditions such that a recombinant ketoreductase polypeptide is produced.

13. The method of claim 12, further comprising the step of recovering said at least one recombinant ketoreductase polypeptide.

* * * * *

SEQUENCE LISTING

```
<160> NUMBER OF SEQ ID NOS: 119

<210> SEQ ID NO 1
<211> LENGTH: 762
<212> TYPE: DNA
<213> ORGANISM: Artificial Sequence
<220> FEATURE:
<223> OTHER INFORMATION: Codon Optimized L. Brevis Sequence
```

<400> SEQUENCE: 1

```
atgtctaacc gtctggatgg caaagtagcc atcattaccg gcgggactct gggtatcggt     60

ttggcaatcg ccacgaaatt tgtagaggag ggtgcgaaag taatgattac tggtcgtcac    120

tccgatgtag gtgaaaaggc cgccaaatca gtaggcactc cggatcagat tcagtttttt    180

cagcacgatt catccgatga agatggctgg acgaaactgt tcgacgccac cgagaaagca    240

ttcggcccgg ttagcacctt agtgaacaat gcagggattg cagttaacaa aagcgttgaa    300

gaaactacca cggccgaatg gcgtaaactg ctggccgtta atctggatgg tgtttttttc    360

ggcacccgtc tgggcattca gcgcatgaaa aataaaggct tgggcgctag catcatcaat    420

atgagcagta ttgaggggtt cgtaggcgat ccgagcctgg gggcatacaa cgcttccaag    480

ggggcggtac gtatcatgtc gaaaagcgca gcgctggatt gcgcactgaa ggactacgat    540

gtgcgtgtca acacagtaca tccgggctat atcaagaccc cgctggtcga tgatctgccg    600

ggtgctgagg aagcgatgtc acagcgtacg aaaaccccta tgggccacat tggcgaaccg    660

aatgacatcg catatatctg tgtgtacctg gcatctaatg aatcgaaatt tgcgacgggt    720

tccgaatttg tggtcgacgg cgggtatacc gcacagtaat ga                       762
```

<210> SEQ ID NO 2
<211> LENGTH: 252
<212> TYPE: PRT
<213> ORGANISM: Artificial Sequence
<220> FEATURE:
<223> OTHER INFORMATION: Translation of Codon Optimized L. Brevis Sequence

<400> SEQUENCE: 2

```
Met Ser Asn Arg Leu Asp Gly Lys Val Ala Ile Ile Thr Gly Gly Thr
1               5                   10                  15

Leu Gly Ile Gly Leu Ala Ile Ala Thr Lys Phe Val Glu Glu Gly Ala
            20                  25                  30

Lys Val Met Ile Thr Gly Arg His Ser Asp Val Gly Glu Lys Ala Ala
        35                  40                  45

Lys Ser Val Gly Thr Pro Asp Gln Ile Gln Phe Phe Gln His Asp Ser
    50                  55                  60

Ser Asp Glu Asp Gly Trp Thr Lys Leu Phe Asp Ala Thr Glu Lys Ala
65                  70                  75                  80

Phe Gly Pro Val Ser Thr Leu Val Asn Asn Ala Gly Ile Ala Val Asn
                85                  90                  95

Lys Ser Val Glu Glu Thr Thr Thr Ala Glu Trp Arg Lys Leu Leu Ala
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Ser Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Tyr Ile Lys
            180                 185                 190

Thr Pro Leu Val Asp Asp Leu Pro Gly Ala Glu Glu Ala Met Ser Gln
        195                 200                 205

Arg Thr Lys Thr Pro Met Gly His Ile Gly Glu Pro Asn Asp Ile Ala
```

```
    210                 215                 220

Tyr Ile Cys Val Tyr Leu Ala Ser Asn Glu Ser Lys Phe Ala Thr Gly
225                 230                 235                 240

Ser Glu Phe Val Val Asp Gly Gly Tyr Thr Ala Gln
                245                 250


<210> SEQ ID NO 3
<211> LENGTH: 759
<212> TYPE: DNA
<213> ORGANISM: Artificial Sequence
<220> FEATURE:
<223> OTHER INFORMATION: Codon Optimized L. Kefir Sequence

<400> SEQUENCE: 3

atgaccgatc gtctgaaggg caaagtagcc atcgtaaccg gcgggactct gggtatcggt      60

ttggcaatcg ccgataaatt tgtagaggag ggtgcgaaag tagttattac tggtcgtcac     120

gcggatgtag gtgaaaaggc cgccaaatca atcggcggca ctgatgttat tcgctttgtc     180

cagcacgatg catccgatga agcaggctgg acgaaactgt tcgacaccac cgaggaggca     240

ttcggcccgg ttacgaccgt cgtgaacaat gcagggattg cagtttccaa aagcgttgaa     300

gacactacca cggaggaatg gcgtaaactg ctgtccgtta atctggatgg tgtttttttc     360

ggcacccgtc tgggcattca gcgcatgaaa aataaaggct tgggcgctag catcatcaat     420

atgagcagta ttgaggggtt cgtaggcgat ccgacgctgg gggcatacaa cgcttccaag     480

ggggcggtac gtatcatgtc gaaaagcgca gcgctggatt gcgcactgaa ggactacgat     540

gtgcgtgtca acacagtaca tccgggctat atcaagaccc cgctggtcga tgatctggaa     600

ggtgctgagg aaatgatgtc acagcgtacg aaaaccccta tggccacat tggcgaaccg      660

aatgacatcg catggatctg tgtgtacctg gcatctgacg aatcgaaatt tgcgacgggt     720

gcagaatttg tggtcgacgg cgggtatacc gcacagtga                            759


<210> SEQ ID NO 4
<211> LENGTH: 252
<212> TYPE: PRT
<213> ORGANISM: Artificial Sequence
<220> FEATURE:
<223> OTHER INFORMATION: Translation of Codon Optimized L. kefir
      Sequence

<400> SEQUENCE: 4

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125
```

```
Met Lys Asn Lys Gly Leu Gly Ala Ser Ile Ile Asn Met Ser Ser Ile
    130                 135                 140

Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Tyr Ile Lys
            180                 185                 190

Thr Pro Leu Val Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250


<210> SEQ ID NO 5
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 5

atgaccgatc gtctgaaggg caaagtagcc atcgtaaccg gcgggactct gggtatcggt      60

ttggcaatcg ccgataaatt tgtagaggag ggtgcgaaag tagttattac tggtcgtcac     120

gcggatgtag gtgaaaaggc cgccaaatca atcggcggca ctgatgttat tcgctttgtc     180

cagcacgatg catccgatga agcaggctgg acgaaactgt tcgacaccac cgaggaggca     240

ttcggcccgg ttacgaccgt cgtgaacaat gcagggattg cagtttccaa aagcgttgaa     300

gacactacca cggaggaatg gcgtaaactg ctgtccgtta atctggatgg tgtttttttc     360

ggcacccgtc tgggcattca gcgcatgaaa aataaaggct tgggcgctag catcatcaat     420

atgagcagta ttgaggggtt cgtaggcgat ccgacgctgg gggcatacaa cgcttccaag     480

ggggcggtac gtatcatgtc gaaaagcgca gcgctggatt gcgcactgaa ggactacgat     540

gtgcgtgtca acacagtaca tccgggctgc atcaagaccc cgctggtcga tgatctggaa     600

ggtgctgagg aaatgatgtc acagcgtacg aaaacccccta tgggccacat tggcgaaccg    660

aatgacatcg catggatctg tgtgtacctg gcatctgacg aatcgaaatt tgcgacgggt     720

gcagaatttg tggtcgacgg cgggtatacc gcacagtga                            759


<210> SEQ ID NO 6
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 6

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45
```

```
Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Pro Leu Val Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 7
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 7

```
atgaccgatc gtctgaaggg caaagtagcc atcgtaaccg gcgggactct gggtatcggt     60

ttggcaatcg ccgataaatt tgtagaggag ggtgcgaaag tagttattac tggtcgtcac    120

gcggatgtag gtgaaaaggc cgccaaatca atcggcggca ctgatgttat tcgctttgtc    180

cagcacgatg catccgatga agcaggctgg acgaaactgt tcgacaccac cgaggaggca    240

ttcggcccgg ttacgaccgt cgtgaacaat gcagggattg cagtttccaa aagcgttgaa    300

gacactacca cggaggaatg gcgtaaactg ctgtccgtta atctggatgg tgtttttttc    360

ggcacccgtc tgggcattca gcgcatgaaa aataaaggct tgggcgctag catcatcaat    420

atgagcagta ttgaggggtt cgtaggcgat ccgacgctgg gggcatacaa cgcttccaag    480

gggggcggtac gtatcatgtc gaaaagcgca gcgctggatt gcgcactgaa ggactacgat    540

gtgcgtgtca acacagtaca tccgggcgcg atcaagaccc cgctgatcga tgatctggaa    600

ggtgctgagg aaatgatgtc acagcgtacg aaaaccccta tgggccacat tggcgaaccg    660

aatgacatcg catggatctg tgtgtacctg gcatctgacg aatcgaaatt tgcgacgggt    720

gcagaatttg tggtcgacgg cgggtatacc gcacagtga                          759
```

<210> SEQ ID NO 8
<211> LENGTH: 252
<212> TYPE: PRT

```
<213> ORGANISM: Artificial Sequence
<220> FEATURE:
<223> OTHER INFORMATION: Variant of L. kefir

<400> SEQUENCE: 8

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Ala Ile Lys
            180                 185                 190

Thr Pro Leu Ile Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250


<210> SEQ ID NO 9
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 9

atgaccgatc gtctgaaggg caaagtagcc atcgtaaccg gcgggactct gggtatcggt      60

ttggcaatcg ccgataaatt tgtagaggag ggtgcgaaag tagttattac tggtcgtcac     120

gcggatgtag gtgaaaaggc cgccaaatca atcggcggca ctgatgttat tcgctttgtc     180

cagcacgatg catccgatga agcaggctgg acgaaactgt tcgacaccac cgaggaggca     240

ttcggcccgg ttacgaccgt cgtgaacaat gcagggattg cagtttccaa aagcgttgaa     300

gacactacca cggaggaatg gcgtaaactg ctgtccgtta atctggatgg tgtttttttc     360

ggcacccgtc tgggcattca gcgcatgaaa aataaaggct tgggcgctag catcatcaat     420

atgagcagta ttgaggggtt cgtaggcgat ccgacgctgg gggcatacaa cgcttccaag     480
```

ggggcggtac gtatcatgtc gaaaagcgca gcgctggatt gcgcactgaa ggactacgat 540
gtgcgtgtca acacagtaca tccgggcccg atcaagaccc cgctgatcga tgatctggaa 600
ggtgctgagg aaatgatgtc acagcgtacg aaaaccccta tgggccacat tggcgaaccg 660
aatgacatcg catggatctg tgtgtacctg gcatctgacg aatcgaaatt tgcgacgggt 720
gcagaatttg tggtcgacgg cgggtatacc gcacagtga 759

<210> SEQ ID NO 10
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 10

Met Thr Asp Arg Leu Lys Gly Lys Val Ala Ile Val Thr Gly Gly Thr
1 5 10 15

Leu Gly Ile Gly Leu Ala Ile Ala Asp Lys Phe Val Glu Glu Gly Ala
20 25 30

Lys Val Val Ile Thr Gly Arg His Ala Asp Val Gly Glu Lys Ala Ala
35 40 45

Lys Ser Ile Gly Gly Thr Asp Val Ile Arg Phe Val Gln His Asp Ala
50 55 60

Ser Asp Glu Ala Gly Trp Thr Lys Leu Phe Asp Thr Thr Glu Glu Ala
65 70 75 80

Phe Gly Pro Val Thr Thr Val Val Asn Asn Ala Gly Ile Ala Val Ser
85 90 95

Lys Ser Val Glu Asp Thr Thr Thr Glu Glu Trp Arg Lys Leu Leu Ser
100 105 110

Val Asn Leu Asp Gly Val Phe Phe Gly Thr Arg Leu Gly Ile Gln Arg
115 120 125

Met Lys Asn Lys Gly Leu Gly Ala Ser Ile Ile Asn Met Ser Ser Ile
130 135 140

Glu Gly Phe Val Gly Asp Pro Thr Leu Gly Ala Tyr Asn Ala Ser Lys
145 150 155 160

Gly Ala Val Arg Ile Met Ser Lys Ser Ala Ala Leu Asp Cys Ala Leu
165 170 175

Lys Asp Tyr Asp Val Arg Val Asn Thr Val His Pro Gly Pro Ile Lys
180 185 190

Thr Pro Leu Ile Asp Asp Leu Glu Gly Ala Glu Glu Met Met Ser Gln
195 200 205

Arg Thr Lys Thr Pro Met Gly His Ile Gly Glu Pro Asn Asp Ile Ala
210 215 220

Trp Ile Cys Val Tyr Leu Ala Ser Asp Glu Ser Lys Phe Ala Thr Gly
225 230 235 240

Ala Glu Phe Val Val Asp Gly Gly Tyr Thr Ala Gln
245 250

<210> SEQ ID NO 11
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 11

```
atgaccgatc gtctgaaggg caaagtagcc atcgtaaccg gcgggactct gggtatcggt      60

ttggcaatcg ccgataaatt tgtagaggag ggtgcgaaag tagttattac tggtcgtcac     120

gcggatgtag gtgaaaaggc cgccaaatca atcggcggca ctgatgttat tcgctttgtc     180

cagcacgatg catccgatga agcaggctgg acgaaactgt tcgacaccac cgaggaggca     240

ttcggcccgg ttacgaccgt cgtgaacaat gcagggattg cagtttccag aagcgttgaa     300

gacactacca cggaggaatg gcgtaaactg ctgtccgtta atctggatgg tgtttttttc     360

ggcacccgtc tgggcattca gcgcatgaaa aataaaggct tgggcgctag catcatcaat     420

atgagcagta ttgaggggtt cgtaggcgat ccgacgctgg gggcatacaa cgcttccaag     480

ggggcggtac gtatcatgtc gaaaagcgca gcgctggatt gcgcactgaa ggactacgat     540

gtgcgtgtca acacagtaca tccgggctgt atcaagaccc cgctggtcga tgatctggaa     600

ggtgctgagg aaatgatgtc acagcgtacg aaaaccccta tgggccacat tggcgaaccg     660

aatgacatcg catggatctg tgtgtacctg gcatctgacg aatcgaaatt tgcgacgggt     720

gcagaatttg tggtcgacgg cgggtatacc gcacagtga                            759
```

```
<210> SEQ ID NO 12
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 12

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Arg Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Cys Ile Lys
            180                 185                 190

Thr Pro Leu Val Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
```

```
225                 230                 235                 240

Ala Glu Phe Val Val Asp Gly Gly Tyr Thr Ala Gln
                245                 250


<210> SEQ ID NO 13
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 13

atgaccgatc gtctgaaggg caaagtagcc atcgtaaccg gcgggactct gggtatcggt      60

ttggcaatcg ccgataaatt tgtagaggag ggtgcgaaag tagttattac tggtcgtcac     120

gcggatgtag gtgaaaaggc cgccaaatca atcggcggca ctgatgttat tcgctttgtc     180

cagcacgatg catccgatga agcaggctgg acgaaactgt tcgacaccac cgaggaggca     240

ttcggcccgg ttacgaccgt cgtgaacaat gcagggattg cagtttccaa aagcgttgaa     300

gacactacca cggaggaatg gcgtaaactg ctgtccgtta atctggatgg tgtttttttc     360

ggcacccgtc tgggcattca gcgcatgaaa aataaaggct tgggcgctag catcatcaat     420

atgagcagta ttgaggggtt cgtaggcgat ccgacgctgg gggcatacaa cgcttccaag     480

ggggcggtac gtatcatgtc gaaaagcgca gcgctggatt gcgcactgaa ggactacgat     540

gtgcgtgtca acacagtaca tccgggcccc atcaagaccc cgctgctcga tgatctggaa     600

ggtgctgagg aaatgatgtc acagcgtacg aaaaccccta tgggccacat tggcgaaccg     660

aatgacatcg catggatctg tgtgtacctg gcatctgacg aatcgaaatt tgcgacgggt     720

gcagaatttg tggtcgacgg cgggtatacc gcacagtga                            759


<210> SEQ ID NO 14
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 14

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Leu Gly Ala Tyr Asn Ala Ser Lys
```

```
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250


<210> SEQ ID NO 15
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 15

atgaccgatc gtctgaaggg caaagtagcc atcgtaaccg gcgggactct gggtatcggt      60

ttggcaatcg ccgataaatt tgtagaggag ggtgcgaaag tagttattac tggtcgtcac     120

gcggatgtag gtgaaaaggc cgccaaatca atcggcggca ctgatgttat tcgctttgtc     180

cagcacgatg catccgatga agcaggctgg acgaaactgt tcgacaccac cgaggaggca     240

ttcggcccgg ttacgaccgt cgtgaacaat gcagggattg cagtttccaa aagcgttgaa     300

gacactacca cggaggaatg gcgtaaactg ctgtccgtta atctggatgg tgtttttttc     360

ggcacccgtc tgggcattca gcgcatgaaa aataaaggct tgggcgctag catcatcaat     420

atgagcagta ttgaggggtt cgtaggcgat ccgacgctgg gggcatacaa cgcttccaag     480

ggggcggtac gtatcatgtc gaaaagcgca gcgctggatt gcgcactgaa ggactacgat     540

gtgcgtgtca acacagtaca tccgggcgcc atcaagaccc cgctgctaga tgatctggaa     600

ggtgctgagg aaatgatgtc acagcgtacg aaaaccccta tgggccacat tggcgaaccg     660

aatgacatcg catggatctg tgtgtacctg gcatctgacg aatcgaaatt tgcgacgggt     720

gcagaatttg tggtcgacgg cgggtatacc gcacagtga                            759


<210> SEQ ID NO 16
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 16

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
```

```
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Ala Ile Lys
            180                 185                 190

Thr Pro Leu Leu Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 17
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 17

```
atgaccgatc gtctgaaggg caaagtagcc atcgtaaccg gcgggactct gggtatcggt     60

ttggcaatcg ccgataaatt tgtagaggag ggtgcgaaag tagttattac tggtcgtcac    120

gcggatgtag gtgaaaaggc cgccaaatca atcggcggca ctgatgttat tcgctttgtc    180

cagcacgatg catccgatga agcaggctgg acgaaactgt tcgacaccac cgaggaggca    240

ttcggcccgg ttacgaccgt cgtgaacaat gcagggattg cagtttccaa aagcgttgaa    300

gacactacca cggaggaatg gcgtaaactg ctgtccgtta atctggatgg tgtttttttc    360

ggcacccgtc tgggcattca gcgcatgaaa aataaaggct tgggcgctag catcatcaat    420

atgagcagta ttgaggggtt cgtaggcgat ccgatgctgg gggcatacaa cgcttccaag    480

gggggcggtac gtatcatgtc gaaaagcgca gcgctggatt gcgcactgaa ggactacgat    540

gtgcgtgtca acacagtaca tccgggcccg atcaagaccc cgctgatcga tgatctggaa    600

ggtgctgagg aaaggatgtc acagcgtacg aaaacccccta tgggccacat tggcgaaccg    660

aatgacatcg catggatctg tgtgtacctg gcatctgacg aatcgaaatt tgcgacgggt    720

gcagaatttg tggtcgacgg cgggtatacc gcacagtga                           759
```

<210> SEQ ID NO 18
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 18

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Met Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Ile Asp Asp Leu Glu Gly Ala Glu Glu Arg Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 19
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 19

```
atgaccgatc gtctgaaggg caaagtagcc atcgtaaccg gcgggactct gggtatcggt     60

ttggcaatcg ccgataaatt tgtagaggag ggtgcgaaag tagttattac tggtcgtcac    120

gcggatgtag gtgaaaaggc cgccaaatca atcggcggca ctgatgttat tcgctttgtc    180

cagcacgatg catccgatga agcaggctgg acgaaactgt tcgacaccac cgaggaggca    240

ttcggcccgg ttacgaccgt cgtgaacaat gcagggattg caatttccaa aagcgttgaa    300

gacactacca cggaggaatg gcgtaaactg ctgtccgtta atctggatgg tgtttttttc    360

ggcacccgtc tgggcattca gcgcatgaaa aataaaggct tgggcgctag catcatcaat    420

atgagcagta ttgaggggtt cgtaggcgat ccgacgctgg gggcatacaa cgcttccaag    480

ggggcggtac gtatcatgtc gaaaagcgca gcgctggatt gcgcactgaa ggactacgat    540

gtgcgtgtca acacagtaca tccgggcccg atcaagaccc cgctgatcga tgatctggaa    600
```

```
ggtgctgagg aaatgatgtc acagcgtacg aaaaccccta tgggccacat tggcgaaccg    660

aatgacatcg catggatctg tgtgtacctg gcatctgacg aatcgaaatt tgcgacgggt    720

gcagaatttg tggtcgacgg cgggtatacc gcacagtga                           759


<210> SEQ ID NO 20
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 20

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Ile Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Ile Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250


<210> SEQ ID NO 21
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 21

atgaccgatc gtctgaaggg caaagtagcc atcgtaaccg gcgggactct gggtatcggt     60

ttggcaatcg ccgataaatt tgtagaggag ggtgcgaaag tagttattac tggtcgtcac    120
```

```
gcggatgtag gtgaaaaggc cgccaaatca atcggcggca ctgatgttat tcgctttgtc    180

cagcacgatg catccgatga agcaggctgg acgaaactgt tcgacaccac cgaggaggca    240

ttcggcccgg ttacgaccgt cgtgaacaat gcagggattg cagtttccaa aagcgttgaa    300

gacactacca cggaggaatg gcgtaaactg ctgtccgtta atctggatgg tgtttttttc    360

ggcacccgtc tgggcattca gcgcatgaaa aataaaggct tgggcgctag catcatcaat    420

atgagcagta ttgaggggct ggtaggcgat ccgacgctgg gggcatacaa cgcttccaag    480

ggggcggtac gtatcatgtc gaaaagcgca gcgctggatt gcgcactgaa ggactacgat    540

gtgcgtgtca acacagtaca tccgggcccc atcaagaccc cgctgctcga tgatctggaa    600

ggtgctgagg aaatgatgtc acagcgtacg aaaaccccta tgggccacat tggcgaaccg    660

aatgacatcg catggatctg tgtgtacctg gcatctgacg aatcgaaatt tgcgacgggt    720

gcagaatttg tggtcgacgg cgggtatacc gcacagtga                           759
```

<210> SEQ ID NO 22
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 22

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 23
<211> LENGTH: 759
<212> TYPE: DNA
<213> ORGANISM: Artificial Sequence
<220> FEATURE:
<223> OTHER INFORMATION: Variant of L. brevis

<400> SEQUENCE: 23

```
atgtctaacc gtctggatgg caaagtagcc atcattaccg gcgggactct gggtatcggt     60

ttggcaatcg ccacgaaatt tgtagaggag ggtgcgaaag taatgattac tggtcgtcac    120

tccgatgtag gtgaaaaggc cgccaaatca gtaggcactc cggatcagat tcagtttttt    180

cagcacgatt catccgatga agatggctgg acgaaactgt tcgacgccac cgagaaagca    240

ttcggcccgg ttagcacctt agtgaacaat gcagggattg cagttaacaa aagcgttgaa    300

gaaactacca cggccgaatg gcgtaaactg ctggccgtta atctggatgg tgtttttttc    360

ggcacccgtc tgggcattca gcgcatgaaa aataaaggct tgggcgctag catcatcaat    420

atgagcagta ttgaggggtt cgtaggcgat ccgagcctgg gggcatacaa cgcttccaag    480

ggggcggtac gtatcatgtc gaaaagcgca gcgctggatt gcgcactgaa ggactacgat    540

gtgcgtgtca acacagtaca tccgggcccg atcaagaccc cgctgctgga tgatctgccg    600

ggtgctgagg aagcgatgtc acagcgtacg aaaaccccta tgggccacat tggcgaaccg    660

aatgacatcg catatatctg tgtgtacctg gcatctaatg aatcgaaatt tgcgacgggt    720

tccgaatttg tggtcgacgg cgggtatacc gcacagtaa                           759
```

<210> SEQ ID NO 24
<211> LENGTH: 252
<212> TYPE: PRT
<213> ORGANISM: Artificial Sequence
<220> FEATURE:
<223> OTHER INFORMATION: Variant of L. brevis

<400> SEQUENCE: 24

```
Met Ser Asn Arg Leu Asp Gly Lys Val Ala Ile Ile Thr Gly Gly Thr
1               5                   10                  15

Leu Gly Ile Gly Leu Ala Ile Ala Thr Lys Phe Val Glu Glu Gly Ala
            20                  25                  30

Lys Val Met Ile Thr Gly Arg His Ser Asp Val Gly Glu Lys Ala Ala
        35                  40                  45

Lys Ser Val Gly Thr Pro Asp Gln Ile Gln Phe Phe Gln His Asp Ser
    50                  55                  60

Ser Asp Glu Asp Gly Trp Thr Lys Leu Phe Asp Ala Thr Glu Lys Ala
65                  70                  75                  80

Phe Gly Pro Val Ser Thr Leu Val Asn Asn Ala Gly Ile Ala Val Asn
                85                  90                  95

Lys Ser Val Glu Glu Thr Thr Thr Ala Glu Trp Arg Lys Leu Leu Ala
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Ser Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175
```

```
Lys Asp Tyr Asp Val Arg Val Asn Thr Val His Pro Gly Pro Ile Lys
            180                 185                 190

Thr Pro Leu Leu Asp Asp Leu Pro Gly Ala Glu Glu Ala Met Ser Gln
        195                 200                 205

Arg Thr Lys Thr Pro Met Gly His Ile Gly Glu Pro Asn Asp Ile Ala
    210                 215                 220

Tyr Ile Cys Val Tyr Leu Ala Ser Asn Glu Ser Lys Phe Ala Thr Gly
225                 230                 235                 240

Ser Glu Phe Val Val Asp Gly Gly Tyr Thr Ala Gln
                245                 250


<210> SEQ ID NO 25
<211> LENGTH: 759
<212> TYPE: DNA
<213> ORGANISM: Artificial Sequence
<220> FEATURE:
<223> OTHER INFORMATION: Variant of L. brevis

<400> SEQUENCE: 25

atgtctaacc gtctggatgg caaagtagcc atcattaccg gcgggactct gggtatcggt     60

ttggcaatcg ccacgaaatt tgtagaggag ggtgcgaaag taatgattac tggtcgtcac    120

tccgatgtag gtgaaaaggc cgccaaatca gtaggcactc cggatcagat tcagtttttt    180

cagcacgatt catccgatga agatggctgg acgaaactgt tcgacgccac cgagaaagca    240

ttcggcccgg ttagcacctt agtgaacaat gcagggattg cagttaacaa aagcgttgaa    300

gaaactacca cggccgaatg gcgtaaactg ctggccgtta atctggatgg tgtttttttc    360

ggcacccgtc tgggcattca gcgcatgaaa aataaaggct tgggcgctag catcatcaat    420

atgagcagta ttgaggggtt cgtaggcgat ccgagcctgg gggcatacaa cgcttccaag    480

ggggcggtac gtatcatgtc gaaaagcgca gcgctggatt gcgcactgaa ggactacgat    540

gtgcgtgtca acacagtaca tccgggcgcg atcaagaccc cgctgctgga tgatctgccg    600

ggtgctgagg aagcgatgtc acagcgtacg aaaacccccta tgggccacat tggcgaaccg    660

aatgacatcg catatatctg tgtgtacctg gcatctaatg aatcgaaatt tgcgacgggt    720

tccgaatttg tggtcgacgg cgggtatacc gcacagtaa                           759


<210> SEQ ID NO 26
<211> LENGTH: 252
<212> TYPE: PRT
<213> ORGANISM: Artificial Sequence
<220> FEATURE:
<223> OTHER INFORMATION: Variant of L. brevis

<400> SEQUENCE: 26

Met Ser Asn Arg Leu Asp Gly Lys Val Ala Ile Ile Thr Gly Gly Thr
1               5                   10                  15

Leu Gly Ile Gly Leu Ala Ile Ala Thr Lys Phe Val Glu Glu Gly Ala
            20                  25                  30

Lys Val Met Ile Thr Gly Arg His Ser Asp Val Gly Glu Lys Ala Ala
        35                  40                  45

Lys Ser Val Gly Thr Pro Asp Gln Ile Gln Phe Phe Gln His Asp Ser
    50                  55                  60

Ser Asp Glu Asp Gly Trp Thr Lys Leu Phe Asp Ala Thr Glu Lys Ala
65                  70                  75                  80

Phe Gly Pro Val Ser Thr Leu Val Asn Asn Ala Gly Ile Ala Val Asn
                85                  90                  95
```

```
Lys Ser Val Glu Glu Thr Thr Thr Ala Glu Trp Arg Lys Leu Leu Ala
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Ser Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Ala Ile Lys
            180                 185                 190

Thr Pro Leu Leu Asp Asp Leu Pro Gly Ala Glu Glu Ala Met Ser Gln
        195                 200                 205

Arg Thr Lys Thr Pro Met Gly His Ile Gly Glu Pro Asn Asp Ile Ala
    210                 215                 220

Tyr Ile Cys Val Tyr Leu Ala Ser Asn Glu Ser Lys Phe Ala Thr Gly
225                 230                 235                 240

Ser Glu Phe Val Val Asp Gly Gly Tyr Thr Ala Gln
                245                 250


<210> SEQ ID NO 27
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 27

atgaccgatc gtctgaaggg caaagtagcc atcgtaaccg gcgggactct gggtatcggt      60

ttggcaatcg ccgataaatt tgtagaggag ggtgcgaaag tagttattac tggtcgtcac     120

gcggatgtag gtgaaaaggc cgccaaatca atcggcggca ctgatgttat tcgctttgtc     180

cagcacgatg catccgatga agcaggctgg acgaaactgt tcgacaccac cgaggaggca     240

ttcggcccgg ttacgaccgt cgtgaacaat gcagggattg cagtttccaa aagcgttgaa     300

gacactacca cggaggaatg gcgtaaactg ctgtccgtta atctggatgg tgtttttttc     360

ggcacccgtc tgggcattca gcgcatgaaa aataaaggct tgggcgctag catcatcaat     420

atgagcagta ttgaggggtt cgtaggcgat ccgacgctgg gggcatacaa cgcttccaag     480

ggggcggtac gtatcatgtc gaaaagcgca gcgctggatt gcgcactgaa ggactacgat     540

gtgcgtgtca acacagtaca tccgggcccc atcaagaccc cgctgctcga tgatctggaa     600

ggtatggagg aaatgatgtc acagcgtacg aaaaccccta tgggccacat tggcgaaccg     660

aatgacatcg catggatctg tgtgtacctg gcatctgacg aatcgaaatt tgcgacgggc     720

gcagaatttg tggtcgacgg cgggtatacc gcacagtga                          759


<210> SEQ ID NO 28
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 28

Met Thr Asp Arg Leu Lys Gly Lys Val Ala Ile Val Thr Gly Gly Thr
1               5                   10                  15
```

```
Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Met Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 29
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 29

```
atgaccgatc gtctgaaggg caaagtagcc atcgtaaccg gcgggactct gggtatcggt     60

ttggcaatcg ccgataaatt tgtagaggag ggtgcgaaag tagttattac tggtcgtcac    120

gcggatgtag gtgaaaaggc cgccaaatca atcggcggca ctgatgttat tcgctttgtc    180

cagcacgatg catccgatga agcaggctgg acgaaactgt tcgacaccac cgaggaggca    240

ttcggcccgg ttacgaccgt cgtgaacaat gcagggattg cagtttccaa aagcgttgaa    300

gacactacca cggaggaatg gcgtaaactg ctgtccgtta atctggatgg tgtttttttc    360

ggcacccgtc tgggcattca gcgcatgaaa aataaaggct tgggcgctag catcatcaat    420

atgagcagta ttgaggggtt cgtaggcgat ccgacgctgg gggcatacaa cgcttccaag    480

gggcggtac gtatcatgtc gaaaagcgca gcgctggatt gcgcactgaa ggactacgat    540

gtgcgtgtca acacagtaca tccgggcgcc atcaagaccc cgctgctcga tgatctggaa    600

ggttacgagg aaatgatgtc acagcgtacg aaaaccccta tgggccacat tggcgaaccg    660

aatgacatcg catggatctg tgtgtacctg gcatctgacg aatcgaaatt tgcgacgggt    720
```

gcagaatttg tggtcgacgg cgggtatacc gcacagtga 759

<210> SEQ ID NO 30
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 30

Met Thr Asp Arg Leu Lys Gly Lys Val Ala Ile Val Thr Gly Gly Thr
1 5 10 15

Leu Gly Ile Gly Leu Ala Ile Ala Asp Lys Phe Val Glu Glu Gly Ala
20 25 30

Lys Val Val Ile Thr Gly Arg His Ala Asp Val Gly Glu Lys Ala Ala
35 40 45

Lys Ser Ile Gly Gly Thr Asp Val Ile Arg Phe Val Gln His Asp Ala
50 55 60

Ser Asp Glu Ala Gly Trp Thr Lys Leu Phe Asp Thr Thr Glu Glu Ala
65 70 75 80

Phe Gly Pro Val Thr Thr Val Val Asn Asn Ala Gly Ile Ala Val Ser
85 90 95

Lys Ser Val Glu Asp Thr Thr Thr Glu Glu Trp Arg Lys Leu Leu Ser
100 105 110

Val Asn Leu Asp Gly Val Phe Phe Gly Thr Arg Leu Gly Ile Gln Arg
115 120 125

Met Lys Asn Lys Gly Leu Gly Ala Ser Ile Ile Asn Met Ser Ser Ile
130 135 140

Glu Gly Phe Val Gly Asp Pro Thr Leu Gly Ala Tyr Asn Ala Ser Lys
145 150 155 160

Gly Ala Val Arg Ile Met Ser Lys Ser Ala Ala Leu Asp Cys Ala Leu
165 170 175

Lys Asp Tyr Asp Val Arg Val Asn Thr Val His Pro Gly Ala Ile Lys
180 185 190

Thr Pro Leu Leu Asp Asp Leu Glu Gly Tyr Glu Glu Met Met Ser Gln
195 200 205

Arg Thr Lys Thr Pro Met Gly His Ile Gly Glu Pro Asn Asp Ile Ala
210 215 220

Trp Ile Cys Val Tyr Leu Ala Ser Asp Glu Ser Lys Phe Ala Thr Gly
225 230 235 240

Ala Glu Phe Val Val Asp Gly Gly Tyr Thr Ala Gln
245 250

<210> SEQ ID NO 31
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 31
atgaccgatc gtctgaaggg caaagtagcc atcgtaaccg gcgggactct gggtatcggt 60
ttggcaatcg ccgataaatt tgtagaggag ggtgcgaaag tagttattac tggtcgtcac 120
gcggatgtag gtgaaaaggc cgccaaatca atcggcggca ctgatgttat tcgctttgtc 180
cagcacgatg catccgatga agcaggctgg acgaaactgt tcgacaccac cgaggaggca 240

```
ttcggcccgg ttacgaccgt cgtgaacaat gcagggattg cagtttccaa aagcgttgaa    300

gacactacca cggaggaatg gcgtaaactg ctgtccgtta atctggatgg tgtttttttc    360

ggcacccgtc tgggcattca gcgcatgaaa aataaaggct tgggcgctag catcatcaat    420

atgagcagta ttgaggggtt cgtaggcgat ccgacgctgg gggcatacaa cgcttccaag    480

ggggcggtac gtatcatgtc gaaaagcgca gcgctggatt gcgcactgaa ggactacgat    540

gtgcgtgtca acacagtaca tccgggcccc atcaagaccc cgctgctcga tgatctggaa    600

ggttgggagg aaatgatgtc acagcgtacg aaaaccccta tgggccacat tggcgaaccg    660

aatgacatcg catggatctg tgtgtacctg gcatctgacg aatcgaaatt tgcgacgggt    720

gcagaatttg tggtcgacgg cgggtatacc gcacagtga                            759
```

<210> SEQ ID NO 32
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 32

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Trp Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 33
<211> LENGTH: 759

```
<212> TYPE: DNA
<213> ORGANISM: Artificial Sequence
<220> FEATURE:
<223> OTHER INFORMATION: Variant of L. kefir

<400> SEQUENCE: 33

atgaccgatc gtctgaaggg caaagtagcc atcgtaaccg gcgggactct gggtatcggt     60

ttggcaatcg ccgataaatt tgtagaggag ggtgcgaaag tagttattac tggtcgtcac    120

gcggatgtag gtgaaaaggc cgccaaatca atcggcggca ctgatgttat tcgctttgtc    180

cagcacgatg catccgatga agcaggctgg acgaaactgt tcgacaccac cgaggaggca    240

ttcggcccgg ttacgaccgt cgtgaacaat gcagggattg tagtttccaa aagcgttgaa    300

gacactacca cggaggaatg gcgtaaactg ctgtccgtta atctggatgg tgtttttttc    360

ggcacccgtc tgggcattca gcgcatgaaa aataaaggct tgggcgctag catcatcaat    420

atgagcagta ttgaggggtt cgtaggcgat ccgacgctgg gggcatacaa cgcttccaag    480

gggcggtac gtatcatgtc gaaaagcgca gcgctggatt gcgcactgaa ggactacgat    540

gtgcgtgtca acacagtaca tccgggcgcc atcaagaccc cgctgctcga tgatctggaa    600

ggtgctgagg aagtgatgtc acagcgtacg aaaacccccta tggcccacat tggcgaaccg    660

aatgacatcg catggatctg tgtgtacctg gcatctgacg aatcgaaatt tgcgacgggt    720

gcagaatttg tggtcgacgg cgggtatacc gcacagtga                           759


<210> SEQ ID NO 34
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 34

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Val Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Ala Ile Lys
            180                 185                 190
```

```
Thr Pro Leu Leu Asp Asp Leu Glu Gly Ala Glu Glu Val Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250


<210> SEQ ID NO 35
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 35

atgaccgatc gtctgaaggg caaagtagcc atcgtaaccg gcgggactct gggtatcggt     60

ttggcaatcg ccgataaatt tgtagaggag ggtgcgaaag tagttattac tggtcgtcac    120

gcggatgtag gtgaaaaggc cgccaaatca atcggcggca ctgatgttat tcgctttgtc    180

cagcacgatg catccgatga agcaggctgg acgaaactgt tcgacaccac cgaggaggca    240

ttcggcccgg ttacgaccgt cgtgaacaat gcagggattg cagtttccaa aagcgttgaa    300

gacactacca cggaggaatg gcgtaaactg ctgtccgtta atctggatgg tgtttttttc    360

ggcacccgtc tgggcattca gcgcatgaaa aataaaggct tgggcgctag catcatcaat    420

atgagcagta ttgaggggtt cgtaggcgat ccgacgctgg gggcatacaa cgcttccaag    480

ggggcggtac gtatcatgtc gaaaagcgca gcgctggatt gcgcactgaa ggactacgat    540

gtgcgtgtca acacagtaca tccgggcccc atcaagaccc cgctgctcga tgatctggaa    600

ggtgctgagg aaatgtattc acagcgtacg aaaaccccta tgggccacat tggcgaaccg    660

aatgacatcg catggatctg tgtgtacctg gcatctgacg aatcgaaatt tgcgacgggt    720

gcagaatttg tggtcgacgg cgggtatacc gcacagtga                           759


<210> SEQ ID NO 36
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 36

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110
```

```
Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Ala Glu Glu Met Tyr Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250


<210> SEQ ID NO 37
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 37

atgaccgatc gtctgaaggg caaagtagcc atcgtaaccg gcgggactct gggtatcggt     60

ttggcaatcg ccgataaatt tgtagaggag ggtgcgaaag tagttattac tggtcgtcac    120

gcggatgtag gtgaaaaggc cgccaaatca atcggcggca ctgatgttat tcgctttgtc    180

cagcacgatg catccgatga agcaggctgg acgaaactgt tcgacaccac cgaggaggca    240

ttcggcccgg ttacgaccgt cgtgaacaat gcagggattg cagtttccaa aagcgttgaa    300

gacactacca cggaggaatg gcgtaaactg ctgtccgtta atctggatgg tgtttttttc    360

ggcacccgtc tgggcattca gcgcatgaaa aataaaggct tgggcgctag catcatcaat    420

atgagcagta ttgaggggct cgtaggcgat ccgacgctgg gggcatacaa cgcttccaag    480

ggggcggtac gtatcatgtc gaaaagcgca gcgctggatt gcgcactgaa ggactacgat    540

gtgcgtgtca acacagtaca tccgggcccc atcaagaccc cgctgctcga tgatctggaa    600

ggttgggagg aaatgatgtc acagcgtacg aaaaccccta tgggccacat tggcgaaccg    660

aatgacatcg catggatctg tgtgtacctg gcatctgacg aatcgaaatt tgcgacgggt    720

gcagaatttg tggtcgacgg cgggtatacc gcacagtga                          759


<210> SEQ ID NO 38
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 38

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30
```

```
Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Trp Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 39
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 39

```
atgaccgatc gtctgaagca taaagtagcc atcgtaaccg gcgggactct gggtatcggt     60

ttggcaatcg ccgataaatt tgtagaggag ggtgcgaaag tagttattac tggtcgtcac    120

gcggatgtag gtgaaaaggc cgccaaatca atcggcggca ctgatgttat tcgctttgtc    180

cagcacgatg catccgatga agcaggctgg acgaaactgt tcgacaccac cgaggaggca    240

ttcggcccgg ttacgaccgt cgtgaacaat gcagggattg cagtttccaa aagcgttgaa    300

gacactacca cggaggaatg gcgtaaactg ctgtccgtta atctggatgg tgtttttttc    360

ggcacccgtc tgggcattca gcgcatgaaa aataaaggct tgggcgctag catcatcaat    420

atgagcagta ttgaggggct cgtaggcgat ccgacgctgg gggcatacaa cgcttccaag    480

ggggcggtac gtatcatgtc gaaaagcgca gcgctggatt gcgcactgaa ggactacgat    540

gtgcgtgtca acacagtaca tccgggcccc atcaagaccc cgctgctcga tgatctggaa    600

ggttgggagg aaatgatgtc acagcgtacg aaaacccccta tgggccacat tggcgaaccg    660

aatgacatcg catggatctg tgtgtacctg gcatctgacg aatcgaaatt tgcgacgggt    720

gcagaatttg tggtcgacgg cgggtatacc gcacagtga                           759
```

```
<210> SEQ ID NO 40
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 40

Met Thr Asp Arg Leu Lys His Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Trp Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250


<210> SEQ ID NO 41
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 41

atgaccgatc gtctgaagca taaagtagcc atcgtaaccg gcgggacact gggtatcggt      60

ttggcaatcg ccgataaatt tgtagaggag ggtgcgaaag tagttattac tggtcgtcac     120

gcggatgtag gtgaaaaggc cgccaaatca atcggcggca ctgatgttat tcgctttgtc     180

cagcacgatg catccgatga agcaggctgg acgaaactgt tcgacaccac cgaggaggca     240

ttcggcccgg ttacgaccgt cgtgaacaat gcagggattg tagtttccaa aagcgttgaa     300

gacactacca cggaggaatg gcgtaaactg ctgtccgtta atctggatgg tgtttttttc     360
```

```
ggcacccgtc tgggcattca gcgcatgaaa aataaaggct tgggcgctag catcatcaat    420

atgagcagta ttgaggggct cgtaggcgat ccgacgctgg gggcatacaa cgcttccaag    480

ggggcggtac gtatcatgtc gaaaagcgca gcgctggatt gcgcactgaa ggactacgat    540

gtgcgtgtca acacagtaca tccgggcccc atcaagaccc cgctgctcga tgatctggaa    600

ggttgggagg aaatgatgtc acagcgtacg aaaacccccta tgggccacat tggcgaaccg    660

aatgacatcg catggatctg tgtgtacctg gcatctgacg aatcgaaatt tgcgacgggt    720

gcagaatttg tggtcgacgg cgggtatacc gcacagtga                            759


<210> SEQ ID NO 42
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 42

Met Thr Asp Arg Leu Lys His Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Val Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Trp Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250


<210> SEQ ID NO 43
<211> LENGTH: 759
<212> TYPE: DNA
<213> ORGANISM: Artificial Sequence
<220> FEATURE:
<223> OTHER INFORMATION: Variant of L. kefir
```

<400> SEQUENCE: 43

```
atgaccgatc gtctgaagca taaagtagcc atcgtaaccg gcgggacact gggtatcggt     60
ttggcaatcg ccgataaatt tgtagaggag ggtgcgaaag tagttattac tggtcgtcac    120
gcggatgtag gtgaaaaggc cgccaaatca atcggcggca ctgatgttat tcgctttgtc    180
cagcacgatg catccgatga agcaggctgg acgaaactgt tcgacaccac cgaggaggca    240
ttcggcccgg ttacgaccgt cgtgaacaat gcagggattg cagttgaaaa aagcgttgaa    300
gacactacca cggaggaatg gcgtaaactg ctgtccgtta atctggatgg tgtttttttc    360
ggcacccgtc tgggcattca gcgcatgaaa aataaaggct tgggcgctag catcatcaat    420
atgagcagta ttgaggggct cgtaggcgat ccgacgctgg gggcatacaa cgcttccaag    480
ggggcggtac gtatcatgtc gaaaagcgca gcgctggatt gcgcactgaa ggactacgat    540
gtgcgtgtca acacagtaca tccgggcccc atcaagaccc cgctgctcga tgatctggaa    600
ggttgggagg aaatgatgtc acagcgtacg aaaacccccta tgggccacat tggcgaaccg    660
aatgacatcg catggatctg tgtgtacctg gcatctgacg aatcgaaatt tgcgacgggt    720
gcagaatttg tggtcgacgg cgggtatacc gcacagtga                           759
```

<210> SEQ ID NO 44
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 44

```
Met Thr Asp Arg Leu Lys His Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Glu
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Trp Glu Glu Met Met Ser Gln
        195                 200                 205

Arg Thr Lys Thr Pro Met Gly His Ile Gly Glu Pro Asn Asp Ile Ala
```

```
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250


<210> SEQ ID NO 45
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 45

atgaccgatc gtctgaagca taaagtagcc atcgtaaccg gcgggacact gggtatcggt      60

ttggcaatcg ccgataaatt tgtagaggag ggtgcgaaag tagttattac tggtcgtcac     120

gcggatgtag gtgaaaaggc cgccaaatca atcggcggca ctgatgttat tcgctttgtc     180

cagcacgatg cgtccgatga agcaggctgg acgaaactgt tcgacaccac cgaggaggca     240

ttcggcccgg ttacgaccgt cgtgaacaat gcagggattg cagttacaaa aagcgttgaa     300

gacactacca cggaggaatg gcgtaaactg ctgtccgtta atctggatgg tgttttttc      360

ggcacccgtc tgggcattca gcgcatgaaa aataaaggct tgggcgctag catcatcaat     420

atgagcagta ttgaggggct cgtaggcgat ccgacgctgg gggcatacaa cgcttccaag     480

ggggcggtac gtatcatgtc gaaaagcgca gcgctggatt gcgcactgaa ggactacgat     540

gtgcgtgtca acacagtaca tccgggcccc atcaagaccc cgctgctcga tgatctggaa     600

ggttgggagg aaatgatgtc acagcgtacg aaaacccccta tgggccacat tggcgaaccg    660

aatgacatcg catggatctg tgtgtacctg gcatctgacg aatcgaaatt tgcgacgggt     720

gcagaatttg tggtcgacgg cgggtatacc gcacagtga                            759


<210> SEQ ID NO 46
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 46

Met Thr Asp Arg Leu Lys His Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Thr
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
```

```
    130                 135                 140

Glu Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Trp Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250


<210> SEQ ID NO 47
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 47

atgaccgatc gtctgaaggg caaagtagcc atcgtaaccg gcgggactct gggtatcggt      60

ttggcaatcg ccgataaatt tgtagaggag ggtgcgaaag tagttattac tggtcgtcac     120

gcggatgtag gtgaaaaggc cgccaaatca atcggcggca ctgatgttat tcgctttgtc     180

cagcacgatg catccgatga agcaggctgg acgaaactgt tcgacaccac cgaggaggca     240

ttcggcccgg ttacgaccgt cgtgaacaat gcagggattg cagtttccaa aagcgttgaa     300

gacactacca cggaggaatg gcgtaaactg ctgtccgtta atctggatgg tgtttttttc     360

ggcacccgtc tgggcattca gcgcatgaaa aataaaggct tgggcgctag catcatcaat     420

atgagcagta ttgaggggtt cgtaggcgat ccgacgctgg gggcatacaa cgcttccaag     480

ggggcggtac gtatcatgtc gaaaagcgca gcgctggatt gcgcactgaa ggactacgat     540

gtgcgtgtca acacagtaca tccgggccca atcaagaccc cgctgatgga tgatctggaa     600

ggtgctgagg aaatgatgtc acagcgtacg aaaaccccta tgggccacat tggcgaaccg     660

aatgacatcg catggatctg tgtgtacctg gcatctgacg aatcgaaatt tgcgacgggt     720

gcagaatttg tggtcgacgg cggtatacc gcacagtga                            759


<210> SEQ ID NO 48
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 48

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
```

```
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Met Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 49
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 49

```
atgaccgatc gtctgaaggg caaagtagcc atcgtaaccg gcgggactct gggtatcggt     60

ttggcaatcg ccgataaatt tgtagaggag ggtgcgaaag tagttattac tggtcgtcac    120

gcggatgtag gtgaaaaggc cgccaaatca atcggcggca ctgatgttat tcgctttgtc    180

cagcacgatg catccgatga agcaggctgg acgaaactgt tcgacaccac cgaggaggca    240

ttcggcccgg ttacgaccgt cgtgaacaat gcagggattg cagtttccaa aagcgttgaa    300

gacactacca cggaggaatg gcgtaaactg ctgtccgtta atctggatgg tgtttttttc    360

ggcacccgtc tgggcattca gcgcatgaaa aataaaggct tgggcgctag catcatcaat    420

atgagcagta ttgaggggtt cgtaggcgat ccgacgctgg gggcatacaa cgcttccaag    480

ggggcggtac gtatcatgtc gaaaagcgca gcgctggatt gcgcactgaa ggactacgat    540

gtgcgtgtca acacagtaca tccgggcccg atcaagaccc cgctgttcga tgatctggaa    600

ggtgctgagg aaatgatgtc acagcgtacg aaaaccccta tgggccacat tggcgaaccg    660

aatgacatcg catggatctg tgtgtacctg gcatctgacg aatcgaaatt tgcgacgggt    720

gcagaatttg tggtcgacgg cgggtatacc gcacagtga                           759
```

<210> SEQ ID NO 50
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 50

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Phe Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 51
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 51

```
atgaccgatc gtctgaaggg caaagtagcc atcgtaaccg gcgggactct gggtatcggt     60

ttggcaatcg ccgataaatt tgtagaggag ggtgcgaaag tagttattac tggtcgtcac    120

gcggatgtag gtgaaaaggc cgccaaatca atcggcggca ctgatgttat tcgctttgtc    180

cagcacgatg catccgatga agcaggctgg acgaaactgt tcgacaccac cgaggaggca    240

ttcggcccgg ttacgaccgt cgtgaacaat gcagggattg cagtttccaa aagcgttgaa    300

gacactacca cggaggaatg gcgtaaactg ctgtccgtta atctggatgg tgtttttttc    360

ggcacccgtc tgagcattca gcgcatgaaa aataaaggct tgggcgctag catcatcaat    420

atgagcagta ttgaggggtt cgtaggcgat ccgacgctgg gggcatacaa cgcttccaag    480
```

```
ggggcggtac gtatcatgtc gaaaagcgca gcgctggatt gcgcactgaa ggactacgat    540

gtgcgtgtca acacagtaca tccgggccca atcaagaccc cgctgctcga tgatctggaa    600

ggtgctgagg aaatgatgtc acagcgtacg aaaaccccta tgggccacat tggcgaaccg    660

aatgacatcg catggatctg tgtgtacctg gcatctgacg aatcgaaatt tgcgacgggt    720

gcagaatttg tggtcgacgg cgggtatacc gcacagtga                            759
```

<210> SEQ ID NO 52
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 52

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Ser Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 53
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 53

```
atgaccgatc gtctgaagaa caaagtagcc atcgtaaccg gcgggactct gggtatcggt     60
```

```
ttggcaatcg ccgataaatt tgtagaggag ggtgcgaaag tagttattac tggtcgtcac    120
gcggatgtag gtgaaaaggc cgccaaatca atcggcggca ctgatgttat tcgctttgtc    180
cagcacgatg catccgatga agcaggctgg acgaaactgt tcgacaccac cgaggaggca    240
ttcggcccgg ttacgaccgt cgtgaacaat gcagggattg cagtttccaa aagcgttgaa    300
gacactacca cggaggaatg gcgtaaactg ctgtccgtta atctggatgg tgtttttttc    360
ggcacccgtc tgggcattca gcgcatgaaa aataaaggct tgggcgctag catcatcaat    420
atgagcagta ttgaggggtt cgtaggcgat ccgacgctgg gggcatacaa cgcttccaag    480
ggggcggtac gtatcatgtc gaaaagcgca gcgctggatt gcgcactgaa ggactacgat    540
gtgcgtgtca acacagtaca tccgggcgcc atcaagaccc cgctgctaga tgatctggaa    600
ggtgctgagg aaatgatgtc acagcgtacg aaaacccctc tgggccacat tggcgaaccg    660
aatgacatcg catggatctg tgtgtacctg gcatctgacg aatcgaaatt tgcgacgggt    720
gcagaatttg tggtcgacgg cgggtatacc gcacagtga                            759
```

<210> SEQ ID NO 54
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 54

```
Met Thr Asp Arg Leu Lys Asn Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Ala Ile Lys
            180                 185                 190

Thr Pro Leu Leu Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240
```

```
Ala Glu Phe Val Val Asp Gly Gly Tyr Thr Ala Gln
                245                 250


<210> SEQ ID NO 55
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 55

atgaccgatc gtctgaagca caaagtagcc atcgtaaccg gcgggactct gggtatcggt      60

ttggcaatcg ccgataaatt tgtagaggag ggtgcgaaag tagttattac tggtcgtcac     120

gcggatgtag gtgaaaaggc cgccaaatca atcggcggca ctgatgttat tcgctttgtc     180

cagcacgatg catccgatga agcaggctgg acgaaactgt tcgacaccac cgaggaggca     240

ttcggcccgg ttacgaccgt cgtgaacaat gcagggattg cagtttccaa aagcgttgaa     300

gacactacca cggaggaatg gcgtaaactg ctgtccgtta atctggatgg tgtttttttc     360

ggcacccgtc tgggcattca gcgcatgaaa aataaaggct tgggcgctag catcatcaat     420

atgagcagta ttgaggggtt cgtaggcgat ccgacgctgg gggcatacaa cgcttccaag     480

ggggcggtac gtatcatgtc gaaaagcgca gcgctggatt gcgcactgaa ggactacgat     540

gtgcgtgtca acacagtaca tccgggcccc atcaagaccc cgctgctaga tgatctggaa     600

ggtgctgagg aaatgatgtc acagcgtacg aaaaccccta tgggccacat tggcgaaccg     660

aatgacatcg catggatctg tgtgtacctg gcatctgacg aatcgaaatt tgcgacgggt     720

gcagaatttg tggtcgacgg cgggtatacc gcacagtga                            759


<210> SEQ ID NO 56
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 56

Met Thr Asp Arg Leu Lys His Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Leu Gly Ala Tyr Asn Ala Ser Lys
145                 150                 155                 160
```

```
Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 57
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 57

```
atgaccgatc gtctgaaggg caaagtagcc atcgtaaccg gcgggagtct gggtatcggt     60

ttggcaatcg ccgataaatt tgtagaggag ggtgcgaaag tagttattac tggtcgtcac    120

gcggatgtag gtgaaaaggc cgccaaatca atcggcggca ctgatgttat tcgctttgtc    180

cagcacgatg catccgatga agcaggctgg acgaaactgt tcgacaccac cgaggaggca    240

ttcggcccgg ttacgaccgt cgtgaacaat gcagggattg cagtttccaa aagcgttgaa    300

gacactacca cggaggaatg gcgtaaactg ctgtccgtta atctggatgg tgtttttttc    360

ggcacccgtc tgggcattca gcgcatgaaa aataaaggct tgggcgctag catcatcaat    420

atgagcagta ttgaggggtt cgtaggcgat ccgacgctgg gggcatacaa cgcttccaag    480

ggggcggtac gtatcatgtc gaaaagcgca gcgctggatt gcgcactgaa ggactacgat    540

gtgcgtgtca acacagtaca tccgggcccc atcaagaccc cgctgctcga tgatctggaa    600

ggtgctgagg aaatgatgtc acagcgtacg aaaaccccta tgggccacat tggcgaaccg    660

aatgacatcg catggatctg tgtgtacctg gcatctgacg aatcgaaatt tgcgacgggt    720

gcagaatttg tggtcgacgg cgggtatacc gcacagtga                            759
```

<210> SEQ ID NO 58
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 58

```
Met Thr Asp Arg Leu Lys Gly Lys Val Ala Ile Val Thr Gly Gly Ser
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80
```

```
Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 59
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 59

```
atgaccgatc gtctgaaggg caaagtagcc atcgtaaccg gcgggacact gggtatcggt      60

ttggcaatcg ccgataaatt tgtagaggag ggtgcgaaag tagttattac tggtcgtcac     120

gcggatgtag gtgaaaaggc cgccaaatca atcggcggca ctgatgttat tcgctttgtc     180

cagcacgatg catccgatga agcaggctgg acgaaactgt tcgacaccac cgaggaggca     240

ttcggcccgg ttacgaccgt cgtgaacaat gcagggattg cagtttccaa aagcgttgaa     300

gacactacca cggaggaatg gcgtaaactg ctgtccgtta atctggatgg tgtttttttc     360

ggcacccgtc tgggcattca gcgcatgaaa aataaaggct tgggcgctag catcatcaat     420

atgagcagta ttgaggggtt cgtaggcgat ccgacgctgg gggcatacaa cgcttccaag     480

gggggcggtac gtatcatgtc gaaaagcgca gcgctggatt gcgcactgaa ggactacgat     540

gtgcgtgtca acacagtaca tccgggcccc atcaagaccc cgctgctcga tgatctggaa     600

ggtgctgagg aaatgatgtc acagcgtacg aaaaccccta tgggccacat tggcgaaccg     660

aatgacatcg catggatctg tgtgtacctg gcatctgacg aatcgaaatt tgcgacgggt     720

gcagaatttg tggtcgacgg cgggtatacc gcacagtga                           759
```

<210> SEQ ID NO 60
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 60

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 61
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 61

```
atgaccgatc gtctgaaggg caaagtagcc atcgtaaccg gcgggactct gggtatcggt     60

ttggcaatcg ccgataaatt tgtagaggag ggtgcgaaag tagttattac tggtcgtcac    120

gcggatgtag gtgaaaaggc cgccaaatca atcggcggca ctgatgttat tcgctttgtc    180

cagcacgatg catccgatga agcaggctgg acgaaactgt tcgacaccac cgaggaggca    240

ttcggcccgg ttacgaccgt cgtgaacaat gcagggattg cactgtccaa aagcgttgaa    300

gacactacca cggaggaatg gcgtaaactg ctgtccgtta atctggatgg tgtttttttc    360

ggcacccgtc tgggcattca gcgcatgaaa aataaaggct tgggcgctag catcatcaat    420

atgagcagta ttgaggggtt cgtaggcgat ccgacgctgg gggcatacaa cgcttccaag    480

ggggcggtac gtatcatgtc gaaaagcgca gcgctggatt gcgcactgaa ggactacgat    540

gtgcgtgtca acacagtaca tccgggcccc atcaagaccc cgctgctaga tgatctggaa    600
```

ggtgctgagg aaatgatgtc acagcgtacg aaaaccccta tgggccacat tggcgaaccg 660
aatgacatcg catggatctg tgtgtacctg gcatctgacg aatcgaaatt tgcgacgggt 720
gcagaatttg tggtcgacgg cgggtatacc gcacagtga 759

<210> SEQ ID NO 62
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 62

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Leu Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 63
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 63
atgaccgatc gtctgaaggg caaagtagcc atcgtaaccg gcgggactct gggtatcggt 60
ttggcaatcg ccgataaatt tgtagaggag ggtgcgaaag tagttattac tggtcgtcac 120
gcggatgtag gtgaaaaggc cgccaaatca atcggcggca ctgatgttat tcgctttgtc 180

```
cagcacgatg catccgatga agcaggctgg acgaaactgt tcgacaccac cgaggaggca    240

ttcggcccgg ttacgaccgt cgtgaacaat gcagggattg caatttccaa aagcgttgaa    300

gacactacca cggaggaatg gcgtaaactg ctgtccgtta atctggatgg tgttttttc     360

ggcacccgtc tgggcattca gcgcatgaaa aataaaggct tgggcgctag catcatcaat    420

atgagcagta ttgaggggtt cgtaggcgat ccgacgctgg gggcatacaa cgcttccaag    480

ggggcggtac gtatcatgtc gaaaagcgca gcgctggatt gcgcactgaa ggactacgat    540

gtgcgtgtca acacagtaca tccgggcccc atcaagaccc cgctgctcga tgatctggaa    600

ggtgctgagg aaatgatgtc acagcgtacg aaaaccccta tggccacat tggcgaaccg     660

aatgacatcg catggatctg tgtgtacctg gcatctgacg aatcgaaatt tgcgacgggt    720

gcagaatttg tggtcgacgg cgggtatacc gcacagtga                           759
```

```
<210> SEQ ID NO 64
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 64

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Ile Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 65
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 65

```
atgaccgatc gtctgaaggg caaagtagcc atcgtaaccg gcgggactct gggtatcggt     60

ttggcaatcg ccgataaatt tgtagaggag ggtgcgaaag tagttattac tggtcgtcac    120

gcggatgtag gtgaaaaggc cgccaaatca atcggcggca ctgatgttat tcgctttgtc    180

cagcacgatg catccgatga agcaggctgg acgaaactgt tcgacaccac cgaggaggca    240

ttcggcccgg ttacgaccgt cgtgaacaat gcagggattg cagtttccaa aagcgttgaa    300

gacactacca cggaggaatg gcgtaaactg ctgtccgtta atctggatgg tgtttttttc    360

ggcacccgtc tgggcattca gcgcatgaaa aataaaggct tgggcgctag catcatcaat    420

atgagcagta ttgaggggca ggtaggcgat ccgacgctgg gggcatacaa cgcttccaag    480

ggggcggtac gtatcatgtc gaaaagcgca gcgctggatt gcgcactgaa ggactacgat    540

gtgcgtgtca acacagtaca tccgggcgcc atcaagaccc cgctgctaga tgatctggaa    600

ggtgctgagg aaatgatgtc acagcgtacg aaaaccccta tgggccacat tggcgaaccg    660

aatgacatcg catggatctg tgtgtacctg gcatctgacg aatcgaaatt tgcgacgggt    720

gcagaatttg tggtcgacgg cgggtatacc gcacagtga                           759
```

<210> SEQ ID NO 66
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 66

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Gln Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175
```

```
Lys Asp Tyr Asp Val Arg Val Asn Thr Val His Pro Gly Ala Ile Lys
            180                 185                 190

Thr Pro Leu Leu Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250


<210> SEQ ID NO 67
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 67

atgaccgatc gtctgaaggg caaagtagcc atcgtaaccg gcgggactct gggtatcggt      60

ttggcaatcg ccgataaatt tgtagaggag ggtgcgaaag tagttattac tggtcgtcac     120

gcggatgtag gtgaaaaggc cgccaaatca atcggcggca ctgatgttat tcgctttgtc     180

cagcacgatg catccgatga agcaggctgg acgaaactgt tcgacaccac cgaggaggca     240

ttcggcccgg ttacgaccgt cgtgaacaat gcagggattg cagtttccaa aagcgttgaa     300

gacactacca cggaggaatg gcgtaaactg ctgtccgtta atctggatgg tgtttttttc     360

ggcacccgtc tgggcattca gcgcatgaaa aataaaggct tgggcgctag catcatcaat     420

atgagcagta ttgaggggat agtaggcgat ccgacgctgg gggcatacaa cgcttccaag     480

ggggcggtac gtatcatgtc gaaaagcgca gcgctggatt gcgcactgaa ggactacgat     540

gtgcgtgtca acacagtaca tccgggcccc atcaagaccc cgctgctcga tgatctggaa     600

ggtgctgagg aaatgatgtc acagcgtacg aaaaccccta tgggccacat tggcgaaccg     660

aatgacatcg catggatctg tgtgtacctg gcatctgacg aatcgaaatt tgcgacgggt     720

gcagaatttg tggtcgacgg cgggtatacc gcacagtga                            759


<210> SEQ ID NO 68
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 68

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95
```

```
Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Ile Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 69
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 69

```
atgaccgatc gtctgaaggg caaagtagcc atcgtaaccg gcgggactct gggtatcggt     60

ttggcaatcg ccgataaatt tgtagaggag ggtgcgaaag tagttattac tggtcgtcac    120

gcggatatag gtgaaaaggc cgccaaatca atcggcggca ctgatgttat tcgctttgtc    180

cagcacgatg catccgatga agcaggctgg acgaaactgt tcgacaccac cgaggaggca    240

ttcggcccgg ttacgaccgt cgtgaacaat gcagggattg cagtttccaa aagcgttgaa    300

gacactacca cggaggaatg gcgtaaactg ctgtccgtta atctggatgg tgtttttttc    360

ggcacccgtc tgggcattca gcgcatgaaa aataaaggct tgggcgctag catcatcaat    420

atgagcagta ttgaggggtt ggtaggcgat ccgacgctgg gggcatacaa cgcttccaag    480

ggggcggtac gtatcatgtc gaaaagcgca gcgctggatt gcgcactgaa ggactacgat    540

gtgcgtgtca acacagtaca tccgggcccc atcaagaccc cgctgctcga tgatctggaa    600

ggtgctgagg aaatgatgtc acagcgtacg aaaacccccta tgggccacat tggcgaaccg    660

aatgacatcg catggatctg tgtgtacctg gcatctgacg aatcgaaatt tgcgacgggt    720

gcagaatttg tggtcgacgg cgggtatacc gcacagtga                           759
```

<210> SEQ ID NO 70
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 70

```
Met Thr Asp Arg Leu Lys Gly Lys Val Ala Ile Val Thr Gly Gly Thr
1               5                   10                  15
```

```
Leu Gly Ile Gly Leu Ala Ile Ala Asp Lys Phe Val Glu Glu Gly Ala
            20                  25                  30

Lys Val Val Ile Thr Gly Arg His Ala Asp Ile Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 71
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 71

```
atgaccgatc gtctgaaggg caaagtagcc atcgtaaccg gcgggactct gggtatcggt     60

ttggcaatcg ccgataaatt tgtagaggag ggtgcgaaag tagttattac tggtcgtcac    120

gcggatgtag gtgaaaaggc cgccaaatca atcggcggca ctgatgttat tcgctttgtc    180

cagcacgatg catccgatga agcaggctgg acgaaactgt tcgacaccac cgaggaggca    240

ttcggcccgg ttacgaccgt cgtgaacaat gcagggattg cagtttccaa aagcgtcgaa    300

gacactacca cggaggaatg gcgtaaactg ctgtccgtta atctggatgg tgtttttttc    360

ggcacccgtc tgggcattca gcgcatgaaa aataaaggct tgggcgctag catcatcaat    420

atgagcagta ttgaggggct tgtaggcgat ccgacgctgg gggcatacaa cgcttccaag    480

gggcggtac gtatcatgtc gaaaagcgca gcgctggatt gcgcactgaa ggactacgat    540

gtgcgtgtca acacagtaca tccgggcgcc atcaagaccc cgctgctaga tgatctggaa    600

ggtgctgagg aaatgatgtc acagcgtacg aaaaccccta tgggccacat tggcgaaccg    660

aatgacatcg catggatctg tgtgtacctg gcatctgacg aatcgaaatt tgcgacgggt    720
```

```
gcagaatttg tggtcgacgg cgggtatacc gcacagtga                          759


<210> SEQ ID NO 72
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 72

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Ala Ile Lys
            180                 185                 190

Thr Pro Leu Leu Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250


<210> SEQ ID NO 73
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 73

atgaccgatc gtctgaaggg caaagtagcc atcgtaaccg gcgggacact gggtatcggt      60

ttggcaatcg ccgataaatt tgtagaggag ggtgcgaaag tagttattac tggtcgtcac     120

gcggatgtag gtgaaaaggc cgccaaatca atcggcggca ctgatgttat tcgctttgtc     180

cagcacgatg catccgatga agcaggctgg acgaaactgt tcgacaccac cgaggaggca     240

ttcggcccgg ttacgaccgt cgtgaacaat gcagggattg cagtttccag aagcgttgaa     300
```

```
gacactacca cggaggaatg gcgtaaactg ctgtccgtta atctggatgg tgtttttttc    360

ggcacccgtc tgggcattca gcgcatgaaa aataaaggct tgggcgctag catcatcaat    420

atgagcagta ttgaggggat agtaggcgat ccgacgctgg gggcatacaa cgcttccaag    480

ggggcggtac gtatcatgtc gaaaagcgca gcgctggatt gcgcactgaa ggactacgat    540

gtgcgtgtca acacagtaca tccgggcccc atcaagaccc cgctgctcga tgatctggaa    600

ggtgctgagg aaatgatgtc acagcgtacg aaaacccccta tgggccacat tggcgaaccg    660

aatgacatcg catggatctg tgtgtacctg gcatctgacg aatcgaaatt tgcgacgggt    720

gcagaatttg tggtcgacgg cgggtatacc gcacagtga                           759

<210> SEQ ID NO 74
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 74

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Arg Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Ile Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 75
<211> LENGTH: 759
<212> TYPE: DNA
```

```
<213> ORGANISM: Artificial Sequence
<220> FEATURE:
<223> OTHER INFORMATION: Variant of L. kefir

<400> SEQUENCE: 75

atgaccgatc gtctgaagac caaagtagcc atcgtaaccg gcgggactct gggtatcggt     60

ttggcaatcg ccgataaatt tgtagaggag ggtgcgaaag tagttattac tggtcgtcac    120

gcggatgtag gtgaaaaggc cgccaaatca atcggcggca ctgatgttat tcgctttgtc    180

cagcacgatg catccgatga agcaggctgg acgaaactgt tcgacaccac cgaggaggca    240

ttcggcccgg ttacgaccgt cgtgaacaat gcagggattg cagtttccaa aagcgttgaa    300

gacactacca cggaggaatg gcgtaaactg ctgtccgtta atctggatgg tgtttttttc    360

ggcacccgtc tgggcattca gcgcatgaaa aataaaggct tgggcgctag catcatcaat    420

atgagcagta ttgaggggct cgtaggcgat ccgacgctgg gggcatacaa cgcttccaag    480

ggggcggtac gtatcatgtc gaaaagcgca gcgctggatt gcgcactgaa ggactacgat    540

gtgcgtgtca acacagtaca tccgggcccc atcaagaccc cgctgctcga tgatctggaa    600

ggttgggagg aaatgatgtc acagcgtacg aaaaccccta tgggccacat tggcgaaccg    660

aatgacatcg catggatctg tgtgtacctg gcatctgacg aatcgaaatt tgcgacgggt    720

gcagaatttg tggtcgacgg cgggtatacc gcacagtga                           759


<210> SEQ ID NO 76
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 76

Met Thr Asp Arg Leu Lys Thr Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Trp Glu Glu Met Met Ser Gln
```

```
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250


<210> SEQ ID NO 77
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 77

atgaccgatc gtctgaagcc caaagtagcc atcgtaaccg gcgggactct gggtatcggt      60

ttggcaatcg ccgataaatt tgtagaggag ggtgcgaaag tagttattac tggtcgtcac     120

gcggatgtag gtgaaaaggc cgccaaatca atcggcggca ctgatgttat tcgctttgtc     180

cagcacgatg catccgatga agcaggctgg acgaaactgt tcgacaccac cgaggaggca     240

ttcggcccgg ttacgaccgt cgtgaacaat gcagggattg cagtttccaa aagcgttgaa     300

gacactacca cggaggaatg gcgtaaactg ctgtccgtta atctggatgg tgtttttttc     360

ggcacccgtc tgggcattca gcgcatgaaa aataaaggct tgggcgctag catcatcaat     420

atgagcagta ttgaggggct cgtaggcgat ccgacgctgg gggcatacaa cgcttccaag     480

ggggcggtac gtatcatgtc gaaaagcgca gcgctggatt gcgcactgaa ggactacgat     540

gtgcgtgtca acacagtaca tccgggcccc atcaagaccc cgctgctcga tgatctggaa     600

ggttgggagg aaatgatgtc acagcgtacg aaaacccccta tgggccacat tggcgaaccg     660

aatgacatcg catggatctg tgtgtacctg gcatctgacg aatcgaaatt tgcgacgggt     720

gcagaatttg tggtcgacgg cgggtatacc gcacagtga                           759


<210> SEQ ID NO 78
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 78

Met Thr Asp Arg Leu Lys Pro Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
```

```
        115                 120                 125

Met Lys Asn Lys Gly Leu Gly Ala Ser Ile Ile Asn Met Ser Ser Ile
    130                 135                 140

Glu Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Trp Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 79
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 79

```
atgaccgatc gtctgaagtg gaaagtagcc atcgtaaccg gcgggactct gggtatcggt     60

ttggcaatcg ccgataaatt tgtagaggag ggtgcgaaag tagttattac tggtcgtcac    120

gcggatgtag gtgaaaaggc cgccaaatca atcggcggca ctgatgttat tcgctttgtc    180

cagcacgatg catccgatga agcaggctgg acgaaactgt tcgacaccac cgaggaggca    240

ttcggcccgg ttacgaccgt cgtgaacaat gcagggattg cagtttccaa aagcgttgaa    300

gacactacca cggaggaatg gcgtaaactg ctgtccgtta atctggatgg tgtttttttc    360

ggcacccgtc tgggcattca gcgcatgaaa aataaaggct tgggcgctag catcatcaat    420

atgagcagta ttgaggggct cgtaggcgat ccgacgctgg gggcatacaa cgcttccaag    480

ggggcggtac gtatcatgtc gaaaagcgca gcgctggatt gcgcactgaa ggactacgat    540

gtgcgtgtca acacagtaca tccgggcccc atcaagaccc cgctgctcga tgatctggaa    600

ggttgggagg aaatgatgtc acagcgtacg aaaaccccta tgggccacat tggcgaaccg    660

aatgacatcg catggatctg tgtgtacctg gcatctgacg aatcgaaatt tgcgacgggt    720

gcagaatttg tggtcgacgg cgggtatacc gcacagtga                           759
```

<210> SEQ ID NO 80
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 80

```
Met Thr Asp Arg Leu Lys Trp Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
```

```
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Trp Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250


<210> SEQ ID NO 81
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 81

atgaccgatc gtctgaagcg taaagtagcc atcgtaaccg gcgggactct gggtatcggt      60

ttggcaatcg ccgataaatt tgtagaggag ggtgcgaaag tagttattac tggtcgtcac     120

gcggatgtag gtgaaaaggc cgccaaatca atcggcggca ctgatgttat tcgctttgtc     180

cagcacgatg catccgatga agcaggctgg acgaaactgt tcgacaccac cgaggaggca     240

ttcggcccgg ttacgaccgt cgtgaacaat gcagggattg cagtttccaa aagcgttgaa     300

gacactacca cggaggaatg gcgtaaactg ctgtccgtta atctggatgg tgttttttc      360

ggcacccgtc tgggcattca gcgcatgaaa aataaaggct tgggcgctag catcatcaat     420

atgagcagta ttgaggggct cgtaggcgat ccgacgctgg gggcatacaa cgcttccaag     480

ggggcggtac gtatcatgtc gaaaagcgca gcgctggatt gcgcactgaa ggactacgat     540

gtgcgtgtca acacagtaca tccgggcccc atcaagaccc cgctgctcga tgatctggaa     600

ggttgggagg aaatgatgtc acagcgtacg aaaacccta tgggccacat tggcgaaccg      660

aatgacatcg catggatctg tgtgtacctg gcatctgacg aatcgaaatt tgcgacgggt     720

gcagaatttg tggtcgacgg cgggtatacc gcacagtga                            759


<210> SEQ ID NO 82
```

<211> LENGTH: 252
<212> TYPE: PRT
<213> ORGANISM: Artificial Sequence
<220> FEATURE:
<223> OTHER INFORMATION: Variant of L. kefir

<400> SEQUENCE: 82

```
Met Thr Asp Arg Leu Lys Arg Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Trp Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 83
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 83

```
atgaccgatc gtctgaagca taaagtagcc atcgtaaccg gcgggacact gggtatcggt     60

ttggcaatcg ccgataaatt tgtagaggag ggtgcgaaag tagttattac tggtcgtcac    120

gcggatgtag gtgaaaaggc cgccaaatca atcggcggca ctgatgttat tcgctttgtc    180

cagcacgatg catccgatga agcaggctgg acgaaactgt tcgacaccac cgaggaggca    240

ttcggcccgg ttacgaccgt cgtgaacaat gcagggattt gcgtttccaa aagcgttgaa    300

gacactacca cggaggaatg gcgtaaactg ctgtccgtta atctggatgg tgtttttttc    360

ggcacccgtc tgggcattca gcgcatgaaa aataaaggct tgggcgctag catcatcaat    420
```

```
atgagcagta ttgaggggct cgtattccat ccgacgctgg gggcatacaa cgcttccaag    480

ggggcggtac gtatcatgtc gaaaagcgca gcgctggatt gcgcactgaa ggactacgat    540

gtgcgtgtca acacagtaca tccgggcccc atcaagaccc cgctgctcga tgatctggaa    600

ggttgggagg aaatgatgtc acagcgtacg aaaaccccta tgggccacat tggcgaaccg    660

aatgacatcg catggatctg tgtgtacctg gcatctgacg aatcgaaatt tgcgacgggt    720

gcagaatttg tggtcgacgg cgggtatacc gcacagtga                           759
```

```
<210> SEQ ID NO 84
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 84

Met Thr Asp Arg Leu Lys His Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Cys Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Leu Val Phe His Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Trp Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250


<210> SEQ ID NO 85
<211> LENGTH: 759
<212> TYPE: DNA
<213> ORGANISM: Artificial Sequence
<220> FEATURE:
<223> OTHER INFORMATION: Variant of L. kefir
```

<400> SEQUENCE: 85

```
atgaccgatc gtctgaagca taaagtagcc atcgtaaccg gcgggacact gggtatcggt     60
ttggcaatcg ccgataaatt tgtagaggag ggtgcgaaag tagttattac tggtcgtcac    120
gcggatgtag gtgaaaaggc cgccaaatca atcggcggca ctgatgttat tcgctttgtc    180
cagcacgatg catccgatga agcaggctgg acgaaactgt tcgacaccac cgaggaggca    240
ttcggcccgg ttacgaccgt cgtgaacaat gcagggattg cagttactaa aagcgttgaa    300
gacactacca cggaggaatg gcgtaaactg ctgtccgtta atctggatgg tgtttttgtc    360
ggcacccgtc tgggcattca gcgcatgaaa aataaaggct tgggcgctag catcatcaat    420
atgagcagta ttgaggggct cgtaggcgat ccgacgctgg gggcatacaa cgcttccaag    480
ggggcggtac gtatcatgtc gaaaagcgca gcgctggatt gcgcactgaa ggactacgat    540
gtgcgtgtca acacagtaca tccgggcccc atcaagaccc cgctgctcga tgatctggaa    600
ggttgggagg aaatgatgtc acagcgtacg aaaaccccta tgggccacat tggcgaaccg    660
aatgacatcg catggatctg tgtgtacctg gcatctgacg aatcgaaatt tgcgacgggt    720
gcagaatttg tggtcgacgg cgggtatacc gcacagtga                           759
```

<210> SEQ ID NO 86
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 86

```
Met Thr Asp Arg Leu Lys His Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Thr
                85                  90                  95

Lys Ser Val Glu Asp Thr Thr Thr Glu Glu Trp Arg Lys Leu Leu Ser
            100                 105                 110

Val Asn Leu Asp Gly Val Phe Val Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Trp Glu Glu Met Met Ser Gln
        195                 200                 205

Arg Thr Lys Thr Pro Met Gly His Ile Gly Glu Pro Asn Asp Ile Ala
    210                 215                 220
```

```
Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250


<210> SEQ ID NO 87
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 87

atgaccgatc gtctgaagca taaagtagcc atcgtaaccg gcgggacact gggtatcggt      60

ttggcaatcg ccgataaatt tgtagaggag ggtgcgaaag tagttattac tggtcgtcac     120

gcggatgtag gtgaaaaggc cgccaaatca atcggcggca ctgatgttat tcgctttgtc     180

cagcacgatg catccgatga agcaggctgg acgaaactgt tcgacaccac cgaggaggca     240

ttcggcccgg ttacgaccgt cgtgaacaat gcagggattg cagtttccgt gagcgttgaa     300

gacactacca cggaggaatg gcgtaaactg ctgtccgtta atctggatgg tgttttcttc     360

ggcacccgtc tgggcattca gcgcatgaaa aataaaggct tgggcgctag catcatcaat     420

atgagcagta ttgaggggct cgtaggcgat ccgacgctgg gggcatacaa cgcttccaag     480

ggggcggtac gtatcatgtc gaaaagcgca gcgctggatt gcgcactgaa ggactacgat     540

gtgcgtgtca acacagtaca tccgggcccc atcaagaccc cgctgctcga tgatctggaa     600

ggttgggagg aaatgatgtc acagcgtacg aaaaccccta tgggccacat tggcgaaccg     660

aatgacatcg catggatctg tgtgtacctg gcatctgacg aatcgaaatt tgcgacgggt     720

gcagaatttg tggtcgacgg cgggtatacc gcacagtga                            759


<210> SEQ ID NO 88
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 88

Met Thr Asp Arg Leu Lys His Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Val Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140
```

```
Glu Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Trp Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 89
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 89

```
atgaccgatc gtctgaagca taaagtagcc atcgtaaccg gcgggacact gggtatcggt      60

ttggcaatcg ccgataaatt tgtagaggag ggtgcgaaag tagttattac tggtcgtcac     120

gcggatgtag gtgaaaaggc cgccaaatca atcggcggca ctgatgttat tcgctttgtc     180

cagcacgatg catccgatga agcaggctgg acgaaactgt tcgacaccac cgaggaggca     240

ttcggcccgg ttacgaccgt cgtgaacaat gcagggattg cagtttccat gagcgttgaa     300

gacactacca cggaggaatg gcgtaaactg ctgtccgtta atctggatgg tgtttttttc     360

ggcacccgtc tgggcattca gcgcatgaaa aataaaggct tgggcgctag catcatcaat     420

atgagcagta ttgaggggct cgtaggcgat ccgacgctgg gggcatacaa cgcttccaag     480

ggggcggtac gtatcatgtc gaaaagcgca gcgctggatt gcgcactgaa ggactacgat     540

gtgcgtgtca acacagtaca tccgggcccc atcaagaccc cgctgctcga tgatctggaa     600

ggttgggagg aaatgatgtc acagcgtacg aaaacccccta tgggccacat tggcgaaccg     660

aatgacatcg catggatctg tgtgtacctg gcatctgacg aatcgaaatt tgcgacgggt     720

gcagaatttg tggtcgacgg cgggtatacc gcacagtga                            759
```

<210> SEQ ID NO 90
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 90

```
Met Thr Asp Arg Leu Lys His Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60
```

```
Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Met Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Trp Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

```
<210> SEQ ID NO 91
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 91

atgaccgatc gtctgaagca taaagtagcc atcgtaaccg gcgggacact gggtatcggt     60

ttggcaatcg ccgataaatt tgtagaggag ggtgcgaaag tagttattac tggtcgtcac    120

gcggatgtag gtgaaaaggc cgccaaatca atcggcggca ctgatgttat tcgctttgtc    180

cagcacgatg catccgatga agcaggctgg acgaaactgt tcgacaccac cgaggaggca    240

ttcggcccgg ttacgaccgt cgtgaacaat gcagggattg cagtttccac gagcgttgaa    300

gacactacca cggaggaatg gcgtaaactg ctgtccgtta atctggatgg tgttttttc    360

ggcacccgtc tgggcattca gcgcatgaaa aataaaggct tgggcgctag catcatcaat    420

atgagcagta ttgaggggct cgtaggcgat ccgacgctgg gggcatacaa cgcttccaag    480

ggggcggtac gtatcatgtc gaaaagcgca gcgctggatt gcgcactgaa ggactacgat    540

gtgcgtgtca acacagtaca tccgggcccc atcaagaccc cgctgctcga tgatctggaa    600

ggttgggagg aaatgatgtc acagcgtacg aaaaccccta tgggccacat tggcgaaccg    660

aatgacatcg catggatctg tgtgtacctg gcatctgacg aatcgaaatt tgcgacgggt    720

gcagaatttg tggtcgacgg cgggtatacc gcacagtga                           759

<210> SEQ ID NO 92
<211> LENGTH: 252
<212> TYPE: PRT
<213> ORGANISM: Artificial Sequence
<220> FEATURE:
```

<223> OTHER INFORMATION: Variant of L. kefir

<400> SEQUENCE: 92

```
Met Thr Asp Arg Leu Lys His Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Thr Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Trp Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 93
<211> LENGTH: 759
<212> TYPE: DNA
<213> ORGANISM: Artificial Sequence
<220> FEATURE:
<223> OTHER INFORMATION: Variant of L. kefir

<400> SEQUENCE: 93

```
atgaccgatc gtctgaagca taaagtagcc atcgtaaccg gcgggacact gggtatcggt     60

ttggcaatcg ccgataaatt tgtagaggag ggtgcgaaag tagttattac tggtcgtcac    120

gcggatgtag gtgaaaaggc cgccaaatca atcggcggca ctgatgttat tcgctttgtc    180

cagcacgatg catccgatga agcaggctgg acgaaactgt tcgacaccac cgaggaggca    240

ttcggcccgg ttacgaccgt cgtgaacaat gcagggattg cagtttccat cagcgttgaa    300

gacactacca cggaggaatg gcgtaaactg ctgtccgtta atctggatgg tgtttttttc    360

ggcacccgtc tgggcattca gcgcatgaaa aataaaggct tgggcgctag catcatcaat    420

atgagcagta ttgaggggct cgtaggcgat ccgacgctgg gggcatacaa cgcttccaag    480

ggggcggtac gtatcatgtc gaaaagcgca gcgctggatt gcgcactgaa ggactacgat    540
```

```
gtgcgtgtca acacagtaca tccgggcccc atcaagaccc cgctgctcga tgatctggaa    600

ggttgggagg aaatgatgtc acagcgtacg aaaaccccta tgggccacat tggcgaaccg    660

aatgacatcg catggatctg tgtgtacctg gcatctgacg aatcgaaatt tgcgacgggt    720

gcagaatttg tggtcgacgg cgggtatacc gcacagtga                           759
```

<210> SEQ ID NO 94
<211> LENGTH: 252
<212> TYPE: PRT
<213> ORGANISM: Artificial Sequence
<220> FEATURE:
<223> OTHER INFORMATION: Variant of L. kefir

<400> SEQUENCE: 94

```
Met Thr Asp Arg Leu Lys His Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Ile Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Leu Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Trp Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 95
<211> LENGTH: 252
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is a polar, non-polar, acidic, aromatic,
      constrained, or basic residue

```
<220> FEATURE:
<221> NAME/KEY: MISC_FEATURE
<222> LOCATION: (16)..(16)
<223> OTHER INFORMATION: Xaa is a polar residue
<220> FEATURE:
<221> NAME/KEY: MISC_FEATURE
<222> LOCATION: (43)..(43)
<223> OTHER INFORMATION: Xaa is a nonpolar or polar residue
<220> FEATURE:
<221> NAME/KEY: MISC_FEATURE
<222> LOCATION: (60)..(60)
<223> OTHER INFORMATION: Xaa is an aromatic, non-polar, or aliphatic
      residue
<220> FEATURE:
<221> NAME/KEY: MISC_FEATURE
<222> LOCATION: (94)..(94)
<223> OTHER INFORMATION: Xaa is an aliphatic, non-polar, or cysteine
      residue
<220> FEATURE:
<221> NAME/KEY: MISC_FEATURE
<222> LOCATION: (95)..(95)
<223> OTHER INFORMATION: Xaa is a non-polar or aliphatic residue
<220> FEATURE:
<221> NAME/KEY: MISC_FEATURE
<222> LOCATION: (96)..(96)
<223> OTHER INFORMATION: Xaa is an acidic or polar residue
<220> FEATURE:
<221> NAME/KEY: MISC_FEATURE
<222> LOCATION: (97)..(97)
<223> OTHER INFORMATION: Xaa is an basic, aliphatic, non-polar, or polar
      residue
<220> FEATURE:
<221> NAME/KEY: MISC_FEATURE
<222> LOCATION: (120)..(120)
<223> OTHER INFORMATION: Xaa is aromatic, aliphatic, or non-polar
      residue
<220> FEATURE:
<221> NAME/KEY: MISC_FEATURE
<222> LOCATION: (125)..(125)
<223> OTHER INFORMATION: Xaa is a polar or non-polar residue
<220> FEATURE:
<221> NAME/KEY: MISC_FEATURE
<222> LOCATION: (142)..(142)
<223> OTHER INFORMATION: Xaa is a polar residue
<220> FEATURE:
<221> NAME/KEY: MISC_FEATURE
<222> LOCATION: (147)..(147)
<223> OTHER INFORMATION: Xaa is an aromatic, aliphatic, polar, or non-
      polar residue
<220> FEATURE:
<221> NAME/KEY: MISC_FEATURE
<222> LOCATION: (149)..(149)
<223> OTHER INFORMATION: Xaa is a non-polar or aromatic residue
<220> FEATURE:
<221> NAME/KEY: MISC_FEATURE
<222> LOCATION: (150)..(150)
<223> OTHER INFORMATION: Xaa is an acidic or constrained residue
<220> FEATURE:
<221> NAME/KEY: MISC_FEATURE
<222> LOCATION: (152)..(152)
<223> OTHER INFORMATION: Xaa is a polar or non-polar residue
<220> FEATURE:
<221> NAME/KEY: MISC_FEATURE
<222> LOCATION: (190)..(190)
<223> OTHER INFORMATION: Xaa is a non-aromatic residue
<220> FEATURE:
<221> NAME/KEY: MISC_FEATURE
<222> LOCATION: (196)..(196)
<223> OTHER INFORMATION: Xaa is an aliphatic, non-polar, or aromatic
      residue
<220> FEATURE:
<221> NAME/KEY: MISC_FEATURE
<222> LOCATION: (202)..(202)
<223> OTHER INFORMATION: Xaa is an aromatic, non-polar, or aliphatic
      residue
<220> FEATURE:
<221> NAME/KEY: MISC_FEATURE
<222> LOCATION: (205)..(205)
<223> OTHER INFORMATION: Xaa is a basic, nonpolar or aliphatic residue
```

```
<220> FEATURE:
<221> NAME/KEY: MISC_FEATURE
<222> LOCATION: (206)..(206)
<223> OTHER INFORMATION: Xaa is an aromatic or non-polar residue

<400> SEQUENCE: 95

Met Ser Asn Arg Leu Asp Xaa Lys Val Ala Ile Ile Thr Gly Gly Xaa
1               5                   10                  15

Leu Gly Ile Gly Leu Ala Ile Ala Thr Lys Phe Val Glu Glu Gly Ala
            20                  25                  30

Lys Val Met Ile Thr Gly Arg His Ser Asp Xaa Gly Glu Lys Ala Ala
        35                  40                  45

Lys Ser Val Gly Thr Pro Asp Gln Ile Gln Phe Xaa Gln His Asp Ser
    50                  55                  60

Ser Asp Glu Asp Gly Trp Thr Lys Leu Phe Asp Ala Thr Glu Lys Ala
65                  70                  75                  80

Phe Gly Pro Val Ser Thr Leu Val Asn Asn Ala Gly Ile Xaa Xaa Xaa
                85                  90                  95

Xaa Ser Val Glu Glu Thr Thr Thr Ala Glu Trp Arg Lys Leu Leu Ala
            100                 105                 110

Val Asn Leu Asp Gly Val Phe Xaa Gly Thr Arg Leu Xaa Ile Gln Arg
        115                 120                 125

Met Lys Asn Lys Gly Leu Gly Ala Ser Ile Ile Asn Met Xaa Ser Ile
    130                 135                 140

Glu Gly Xaa Val Xaa Xaa Pro Xaa Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Xaa Ile Lys
            180                 185                 190

Thr Pro Leu Xaa Asp Asp Leu Pro Gly Xaa Glu Glu Xaa Xaa Ser Gln
        195                 200                 205

Arg Thr Lys Thr Pro Met Gly His Ile Gly Glu Pro Asn Asp Ile Ala
    210                 215                 220

Tyr Ile Cys Val Tyr Leu Ala Ser Asn Glu Ser Lys Phe Ala Thr Gly
225                 230                 235                 240

Ser Glu Phe Val Val Asp Gly Gly Tyr Thr Ala Gln
                245                 250


<210> SEQ ID NO 96
<211> LENGTH: 252
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is a polar, non-polar, acidic, aromatic,
      constrained, or basic residue
<220> FEATURE:
<221> NAME/KEY: MISC_FEATURE
<222> LOCATION: (16)..(16)
<223> OTHER INFORMATION: Xaa is a polar residue
<220> FEATURE:
<221> NAME/KEY: MISC_FEATURE
<222> LOCATION: (43)..(43)
<223> OTHER INFORMATION: Xaa is a nonpolar or polar residue
<220> FEATURE:
<221> NAME/KEY: MISC_FEATURE
<222> LOCATION: (60)..(60)
<223> OTHER INFORMATION: Xaa is an aromatic, non-polar, or aliphatic
```

```
      residue
<220> FEATURE:
<221> NAME/KEY: MISC_FEATURE
<222> LOCATION: (94)..(94)
<223> OTHER INFORMATION: Xaa is an aliphatic, non-polar, or cysteine
      residue
<220> FEATURE:
<221> NAME/KEY: MISC_FEATURE
<222> LOCATION: (95)..(95)
<223> OTHER INFORMATION: Xaa is a non-polar or aliphatic residue
<220> FEATURE:
<221> NAME/KEY: MISC_FEATURE
<222> LOCATION: (96)..(96)
<223> OTHER INFORMATION: Xaa is an acidic or polar residue
<220> FEATURE:
<221> NAME/KEY: MISC_FEATURE
<222> LOCATION: (97)..(97)
<223> OTHER INFORMATION: Xaa is an basic, aliphatic, non-polar, or polar
      residue
<220> FEATURE:
<221> NAME/KEY: MISC_FEATURE
<222> LOCATION: (120)..(120)
<223> OTHER INFORMATION: Xaa is aromatic, aliphatic, or non-polar
      residue
<220> FEATURE:
<221> NAME/KEY: MISC_FEATURE
<222> LOCATION: (125)..(125)
<223> OTHER INFORMATION: Xaa is a polar or non-polar residue
<220> FEATURE:
<221> NAME/KEY: MISC_FEATURE
<222> LOCATION: (142)..(142)
<223> OTHER INFORMATION: Xaa is a polar residue
<220> FEATURE:
<221> NAME/KEY: MISC_FEATURE
<222> LOCATION: (147)..(147)
<223> OTHER INFORMATION: Xaa is an aromatic, aliphatic, polar, or non-
      polar residue
<220> FEATURE:
<221> NAME/KEY: MISC_FEATURE
<222> LOCATION: (149)..(149)
<223> OTHER INFORMATION: Xaa is a non-polar or aromatic residue
<220> FEATURE:
<221> NAME/KEY: MISC_FEATURE
<222> LOCATION: (150)..(150)
<223> OTHER INFORMATION: Xaa is an acidic or constrained residue
<220> FEATURE:
<221> NAME/KEY: MISC_FEATURE
<222> LOCATION: (152)..(152)
<223> OTHER INFORMATION: Xaa is a polar or non-polar residue
<220> FEATURE:
<221> NAME/KEY: MISC_FEATURE
<222> LOCATION: (190)..(190)
<223> OTHER INFORMATION: Xaa is a non-aromatic residue
<220> FEATURE:
<221> NAME/KEY: MISC_FEATURE
<222> LOCATION: (196)..(196)
<223> OTHER INFORMATION: Xaa is an aliphatic, non-polar, or aromatic
      residue
<220> FEATURE:
<221> NAME/KEY: MISC_FEATURE
<222> LOCATION: (202)..(202)
<223> OTHER INFORMATION: Xaa is an aromatic, non-polar, or aliphatic
      residue
<220> FEATURE:
<221> NAME/KEY: MISC_FEATURE
<222> LOCATION: (205)..(205)
<223> OTHER INFORMATION: Xaa is a basic, nonpolar or aliphatic residue
<220> FEATURE:
<221> NAME/KEY: MISC_FEATURE
<222> LOCATION: (206)..(206)
<223> OTHER INFORMATION: Xaa is an aromatic or non-polar residue

<400> SEQUENCE: 96

Met Thr Asp Arg Leu Lys Xaa Lys Val Ala Ile Val Thr Gly Gly Xaa
1               5                   10                  15

Leu Gly Ile Gly Leu Ala Ile Ala Asp Lys Phe Val Glu Glu Gly Ala
            20                  25                  30
```

```
Lys Val Val Ile Thr Gly Arg His Ala Asp Xaa Gly Glu Lys Ala Ala
        35                  40                  45

Lys Ser Ile Gly Gly Thr Asp Val Ile Arg Phe Xaa Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Xaa Xaa Xaa
                85                  90                  95

Xaa Ser Val Glu Asp Thr Thr Thr Glu Glu Trp Arg Lys Leu Leu Ser
            100                 105                 110

Val Asn Leu Asp Gly Val Phe Xaa Gly Thr Arg Leu Xaa Ile Gln Arg
        115                 120                 125

Met Lys Asn Lys Gly Leu Gly Ala Ser Ile Ile Asn Met Xaa Ser Ile
    130                 135                 140

Glu Gly Xaa Val Xaa Xaa Pro Xaa Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Xaa Ile Lys
            180                 185                 190

Thr Pro Leu Xaa Asp Asp Leu Glu Gly Xaa Glu Glu Xaa Xaa Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 97
<211> LENGTH: 759
<212> TYPE: DNA
<213> ORGANISM: Lactobacillus Minor

<400> SEQUENCE: 97

```
atgaccgatc ggttgaaggg gaaagtagca attgtaactg gcggtacctt gggaattggc      60

ttggcaatcg ctgataagtt tgttgaagaa ggcgcaaagg ttgttattac cggccgtcac     120

gctgatgtag gtgaaaaagc tgccagatca atcggcggca cagacgttat ccgttttgtc     180

caacacgatg cttctgatga aaccggctgg actaagttgt ttgatacgac tgaagaagca     240

tttggcccag ttaccacggt tgtcaacaat gccggaattg cggtcagcaa gagtgttgaa     300

gataccacaa ctgaagaatg gcgcaagctg ctctcagtta acttggatgg tgtcttcttc     360

ggtacccgtc ttggaatcca acgtatgaag aataaaggac tcggagcatc aatcatcaat     420

atgtcatcta tcgaaggttt tgttggtgat ccagctctgg gtgcatacaa cgcttcaaaa     480

ggtgctgtca gaattatgtc taaatcagct gccttggatt gcgctttgaa ggactacgat     540

gttcgggtta acactgttca tccaggttat atcaagacac cattggttga cgatcttgaa     600

ggggcagaag aaatgatgtc acagcggacc aagacaccaa tgggtcatat cggtgaacct     660

aacgatatcg cttggatctg tgtttacctg gcatctgacg aatctaaatt tgccactggt     720

gcagaattcg ttgtcgacgg agggtacacc gcccaatag                            759
```

<210> SEQ ID NO 98

<211> LENGTH: 252
<212> TYPE: PRT
<213> ORGANISM: Lactobacillus Minor

<400> SEQUENCE: 98

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Arg Ser Ile Gly Gly Thr Asp Val Ile Arg Phe Val Gln His Asp Ala
    50                  55                  60

Ser Asp Glu Thr Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Ala Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Tyr Ile Lys
            180                 185                 190

Thr Pro Leu Val Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 99
<211> LENGTH: 1011
<212> TYPE: DNA
<213> ORGANISM: Artificial Sequence
<220> FEATURE:
<223> OTHER INFORMATION: SADH from C. parapsilosis

<400> SEQUENCE: 99

```
atgtcaattc catcaagcca gtacggattc gtattcaata agcaatcagg acttaatttg      60

agaaatgatt tgcctgtcca caagcccaaa gcgggtcaat tgttgttgaa agttgatgct     120

gttggattgt gtcattctga tttacatgtc atttacgaag ggttggattg tggtgataat     180

tatgtcatgg gacatgaaat tgctggaact gttgctgctg tgggtgatga tgtcattaac     240

tacaaggttg gtgatcgtgt tgcctgtgtc ggacccaatg gatgtggtgg gtgcaagtat     300

tgtcgtggtg ccattgacaa tgtatgtaaa aacgcatttg gtgattggtt cggattgggg     360

tacgatggtg ggtatcaaca gtacttgttg gttactagac cacgtaactt gtctcgtatc     420

ccagataacg tatctgcaga cgtggctgcg gcttcaactg atgctgtatt gacaccatat     480
```

```
cacgcaatca agatggctca agtgtcacca acttcgaata tcttgcttat tggtgctggt    540

ggattgggtg gaaatgcaat tcaagttgcc aaggcatttg gtgcgaaagt tactgttttg    600

gacaaaaaaa aggaggctcg tgaccaagca aagaagttgg gtgctgatgc agtttatgaa    660

acattgccag aatccatttc tcctggctct ttttcagcat gttttgattt tgtttcagtg    720

caagctacat ttgatgtatg tcaaaagtat gttgaaccaa agggtgtaat tatgcccgtg    780

ggactcggtg ctcctaattt atcgtttaat ttgggagatt tggcattgag agaaattcga    840

atcttgggta gtttttgggg aactactaat gatttggatg atgttttgaa attggttagt    900

gaaggtaaag ttaaacccgt tgtgagaagt gccaaattga aggaattgcc agagtatatt    960

gaaaaattga gaaacaatgc ttatgaaggt agagttgttt ttaatccata g            1011
```

```
<210> SEQ ID NO 100
<211> LENGTH: 336
<212> TYPE: PRT
<213> ORGANISM: Artificial Sequence
<220> FEATURE:
<223> OTHER INFORMATION: SADH from C. parapsilosis

<400> SEQUENCE: 100

Met Ser Ile Pro Ser Ser Gln Tyr Gly Phe Val Phe Asn Lys Gln Ser
1               5                   10                  15

Gly Leu Asn Leu Arg Asn Asp Leu Pro Val His Lys Pro Lys Ala Gly
            20                  25                  30

Gln Leu Leu Leu Lys Val Asp Ala Val Gly Leu Cys His Ser Asp Leu
        35                  40                  45

His Val Ile Tyr Glu Gly Leu Asp Cys Gly Asp Asn Tyr Val Met Gly
    50                  55                  60

His Glu Ile Ala Gly Thr Val Ala Ala Val Gly Asp Asp Val Ile Asn
65                  70                  75                  80

Tyr Lys Val Gly Asp Arg Val Ala Cys Val Gly Pro Asn Gly Cys Gly
                85                  90                  95

Gly Cys Lys Tyr Cys Arg Gly Ala Ile Asp Asn Val Cys Lys Asn Ala
            100                 105                 110

Phe Gly Asp Trp Phe Gly Leu Gly Tyr Asp Gly Gly Tyr Gln Gln Tyr
        115                 120                 125

Leu Leu Val Thr Arg Pro Arg Asn Leu Ser Arg Ile Pro Asp Asn Val
    130                 135                 140

Ser Ala Asp Val Ala Ala Ala Ser Thr Asp Ala Val Leu Thr Pro Tyr
145                 150                 155                 160

His Ala Ile Lys Met Ala Gln Val Ser Pro Thr Ser Asn Ile Leu Leu
                165                 170                 175

Ile Gly Ala Gly Gly Leu Gly Gly Asn Ala Ile Gln Val Ala Lys Ala
            180                 185                 190

Phe Gly Ala Lys Val Thr Val Leu Asp Lys Lys Lys Glu Ala Arg Asp
        195                 200                 205

Gln Ala Lys Lys Leu Gly Ala Asp Ala Val Tyr Glu Thr Leu Pro Glu
    210                 215                 220

Ser Ile Ser Pro Gly Ser Phe Ser Ala Cys Phe Asp Phe Val Ser Val
225                 230                 235                 240

Gln Ala Thr Phe Asp Val Cys Gln Lys Tyr Val Glu Pro Lys Gly Val
                245                 250                 255

Ile Met Pro Val Gly Leu Gly Ala Pro Asn Leu Ser Phe Asn Leu Gly
            260                 265                 270
```

```
Asp Leu Ala Leu Arg Glu Ile Arg Ile Leu Gly Ser Phe Trp Gly Thr
        275                 280                 285

Thr Asn Asp Leu Asp Asp Val Leu Lys Leu Val Ser Glu Gly Lys Val
    290                 295                 300

Lys Pro Val Val Arg Ser Ala Lys Leu Lys Glu Leu Pro Glu Tyr Ile
305                 310                 315                 320

Glu Lys Leu Arg Asn Asn Ala Tyr Glu Gly Arg Val Val Phe Asn Pro
                325                 330                 335


<210> SEQ ID NO 101
<211> LENGTH: 1041
<212> TYPE: DNA
<213> ORGANISM: Artificial Sequence
<220> FEATURE:
<223> OTHER INFORMATION: Codon optimized ADH from S. coelicolor

<400> SEQUENCE: 101

atgaaggcac tgcagtaccg caccatcggc gccccgcccg aggtcgtcac cgtcccggac      60

ccggagccgg gccccggcca ggtgctgttg aaggtgaccg cggccggagt ctgccactcc     120

gacatcgcgg tgatgagctg gcccgccgag ggcttcccgt acgagctgcc gctcaccctc     180

ggccacgagg gcgtcggcac cgtggccgcg ctcggcgccg gggtgacggg gctcgccgag     240

ggcgacgcgg tcgccgtgta cgggccctgg ggctgcggca cctgcgccaa gtgcgcggag     300

ggcaaggaga actactgcct gcgcgccgac gagctgggca tccgtccgcc ggggctcggg     360

cgtccggggt ccatggccga gtacctgctg atcgacgacc cccggcacct ggtcccgctg     420

gacgggctcg acccggtcgc ggcggtgccg ctcaccgacg ccggactgac gccgtaccac     480

gcgatcaagc ggtcgctgcc caagctggtc cccggctcca ccgcggtggt catcggcacc     540

ggtggtctcg gccacgtcgc catccagctg ctgcgcgccc tgacgtccgc ccgggtggtc     600

gccctggacg tcagcgagga gaagctgcgc ctcgcccgtg cggtgggcgc gcacgaggcg     660

gtgctgtcgg acgcgaaggc cgcggacgcg gtgcgcgaga tcaccggcgg tctcggtgcc     720

gaggccgtgt tcgacttcgt cggcgtggcg cccaccgtgc agaccgccgg agccgtcgcg     780

gccgtcgagg gcgatgtcac cctggtcggc atcggcggcg gatcgctgcc cgtcggcttc     840

ggcatgctgc cgttcgaggt gtcggtcaac gccccctact ggggcagccg cagcgagctg     900

accgaggtgc tgaacctggc ccgctccggt gccgtgtcgg tgcacaccga gacgtactcc     960

ctggacgacg ccccgctcgc ctacgagcgg ctgcacgagg gcagggtcaa cggccgcgcg    1020

gtgatcctgc cccacggctg a                                              1041


<210> SEQ ID NO 102
<211> LENGTH: 346
<212> TYPE: PRT
<213> ORGANISM: Artificial Sequence
<220> FEATURE:
<223> OTHER INFORMATION: ADH from S. coelicolor

<400> SEQUENCE: 102

Met Lys Ala Leu Gln Tyr Arg Thr Ile Gly Ala Pro Pro Glu Val Val
1               5                   10                  15

Thr Val Pro Asp Pro Glu Pro Gly Pro Gly Gln Val Leu Leu Lys Val
            20                  25                  30

Thr Ala Ala Gly Val Cys His Ser Asp Ile Ala Val Met Ser Trp Pro
        35                  40                  45

Ala Glu Gly Phe Pro Tyr Glu Leu Pro Leu Thr Leu Gly His Glu Gly
```

```
    50                  55                  60

Val Gly Thr Val Ala Ala Leu Gly Ala Gly Val Thr Gly Leu Ala Glu
65                  70                  75                  80

Gly Asp Ala Val Ala Val Tyr Gly Pro Trp Gly Cys Gly Thr Cys Ala
                85                  90                  95

Lys Cys Ala Glu Gly Lys Glu Asn Tyr Cys Leu Arg Ala Asp Glu Leu
            100                 105                 110

Gly Ile Arg Pro Pro Gly Leu Gly Arg Pro Gly Ser Met Ala Glu Tyr
        115                 120                 125

Leu Leu Ile Asp Asp Pro Arg His Leu Val Pro Leu Asp Gly Leu Asp
    130                 135                 140

Pro Val Ala Ala Val Pro Leu Thr Asp Ala Gly Leu Thr Pro Tyr His
145                 150                 155                 160

Ala Ile Lys Arg Ser Leu Pro Lys Leu Val Pro Gly Ser Thr Ala Val
                165                 170                 175

Val Ile Gly Thr Gly Gly Leu Gly His Val Ala Ile Gln Leu Leu Arg
            180                 185                 190

Ala Leu Thr Ser Ala Arg Val Val Ala Leu Asp Val Ser Glu Glu Lys
        195                 200                 205

Leu Arg Leu Ala Arg Ala Val Gly Ala His Glu Ala Val Leu Ser Asp
    210                 215                 220

Ala Lys Ala Ala Asp Ala Val Arg Glu Ile Thr Gly Gly Leu Gly Ala
225                 230                 235                 240

Glu Ala Val Phe Asp Phe Val Gly Val Ala Pro Thr Val Gln Thr Ala
                245                 250                 255

Gly Ala Val Ala Ala Val Glu Gly Asp Val Thr Leu Val Gly Ile Gly
            260                 265                 270

Gly Gly Ser Leu Pro Val Gly Phe Gly Met Leu Pro Phe Glu Val Ser
        275                 280                 285

Val Asn Ala Pro Tyr Trp Gly Ser Arg Ser Glu Leu Thr Glu Val Leu
    290                 295                 300

Asn Leu Ala Arg Ser Gly Ala Val Ser Val His Thr Glu Thr Tyr Ser
305                 310                 315                 320

Leu Asp Asp Ala Pro Leu Ala Tyr Glu Arg Leu His Glu Gly Arg Val
                325                 330                 335

Asn Gly Arg Ala Val Ile Leu Pro His Gly
            340                 345


<210> SEQ ID NO 103
<211> LENGTH: 1032
<212> TYPE: DNA
<213> ORGANISM: Artificial Sequence
<220> FEATURE:
<223> OTHER INFORMATION: Codon optimized ADH from S. salmonicolor

<400> SEQUENCE: 103

atggcaaaga tcgacaacgc agttctgccg gagggttctc tggtgctggt caccggcgcg      60

aacggctttg tcgctagcca tgtggtcgaa caactgctgg aacacggcta taaggtgcgc     120

ggcactgctc gctctgcctc caaactggcg aacctgcaga aacgttggga cgccaaatac     180

cctggtcgtt tcgagactgc cgttgttgaa gacatgctga agcagggtgc atatgatgaa     240

gttattaaag gcgcggcagg tgtcgcccac atcgcgtccg tggtcagctt ttctaacaaa     300

tatgatgagg tggtaactcc tgcgatcggt ggcacgctga atgccctgcg tgccgcagct     360

gctacgcctt ccgtgaaacg ttttgtgctg accagcagca ctgtttctgc actgattcca     420
```

```
aaacctaacg tcgaaggtat ttatctggat gagaagagct ggaacctgga aagcattgat    480

aaggctaaaa ccctgcctga atctgatccg cagaaaagcc tgtgggtcta cgccgcaagc    540

aaaacggaag cggaactggc tgcctggaaa ttcatggacg aaaacaaacc gcactttact    600

ctgaatgccg ttctgccaaa ctacactatc ggtaccattt ttgacccaga aacccaatcc    660

ggttccactt ccggctggat gatgtctctg ttcaatggcg aagtatctcc ggcactggcg    720

ctgatgccgc cgcagtacta tgtctctgca gttgatatcg gtctgctgca cctgggttgt    780

ctggttctgc cgcaaatcga acgccgtcgt gtttacggca ccgcaggcac ctttgattgg    840

aacaccgttc tggcgacctt ccgtaaactg tatccgtcca agacgttccc ggctgacttt    900

ccggatcagg gccaggatct gtccaaattt gataccgccc cgagcctgga gattctgaaa    960

tccctgggcc gccctggctg gcgtagcatc gaggaatcta tcaaagatct ggtgggttcc   1020

gagaccgcct aa                                                        1032
```

<210> SEQ ID NO 104
<211> LENGTH: 343
<212> TYPE: PRT
<213> ORGANISM: Artificial Sequence
<220> FEATURE:
<223> OTHER INFORMATION: ADH from S. salmonicolor

<400> SEQUENCE: 104

```
Met Ala Lys Ile Asp Asn Ala Val Leu Pro Glu Gly Ser Leu Val Leu
1               5                   10                  15

Val Thr Gly Ala Asn Gly Phe Val Ala Ser His Val Val Glu Gln Leu
            20                  25                  30

Leu Glu His Gly Tyr Lys Val Arg Gly Thr Ala Arg Ser Ala Ser Lys
        35                  40                  45

Leu Ala Asn Leu Gln Lys Arg Trp Asp Ala Lys Tyr Pro Gly Arg Phe
    50                  55                  60

Glu Thr Ala Val Val Glu Asp Met Leu Lys Gln Gly Ala Tyr Asp Glu
65                  70                  75                  80

Val Ile Lys Gly Ala Ala Gly Val Ala His Ile Ala Ser Val Val Ser
                85                  90                  95

Phe Ser Asn Lys Tyr Asp Glu Val Val Thr Pro Ala Ile Gly Gly Thr
            100                 105                 110

Leu Asn Ala Leu Arg Ala Ala Ala Ala Thr Pro Ser Val Lys Arg Phe
        115                 120                 125

Val Leu Thr Ser Ser Thr Val Ser Ala Leu Ile Pro Lys Pro Asn Val
    130                 135                 140

Glu Gly Ile Tyr Leu Asp Glu Lys Ser Trp Asn Leu Glu Ser Ile Asp
145                 150                 155                 160

Lys Ala Lys Thr Leu Pro Glu Ser Asp Pro Gln Lys Ser Leu Trp Val
                165                 170                 175

Tyr Ala Ala Ser Lys Thr Glu Ala Glu Leu Ala Ala Trp Lys Phe Met
            180                 185                 190

Asp Glu Asn Lys Pro His Phe Thr Leu Asn Ala Val Leu Pro Asn Tyr
        195                 200                 205

Thr Ile Gly Thr Ile Phe Asp Pro Glu Thr Gln Ser Gly Ser Thr Ser
    210                 215                 220

Gly Trp Met Met Ser Leu Phe Asn Gly Glu Val Ser Pro Ala Leu Ala
225                 230                 235                 240

Leu Met Pro Pro Gln Tyr Tyr Val Ser Ala Val Asp Ile Gly Leu Leu
```

```
            245                 250                 255

His Leu Gly Cys Leu Val Leu Pro Gln Ile Glu Arg Arg Arg Val Tyr
            260                 265                 270

Gly Thr Ala Gly Thr Phe Asp Trp Asn Thr Val Leu Ala Thr Phe Arg
        275                 280                 285

Lys Leu Tyr Pro Ser Lys Thr Phe Pro Ala Asp Phe Pro Asp Gln Gly
    290                 295                 300

Gln Asp Leu Ser Lys Phe Asp Thr Ala Pro Ser Leu Glu Ile Leu Lys
305                 310                 315                 320

Ser Leu Gly Arg Pro Gly Trp Arg Ser Ile Glu Glu Ser Ile Lys Asp
                325                 330                 335

Leu Val Gly Ser Glu Thr Ala
            340
```

<210> SEQ ID NO 105
<211> LENGTH: 1125
<212> TYPE: DNA
<213> ORGANISM: Artificial Sequence
<220> FEATURE:
<223> OTHER INFORMATION: Codon optimized ADH from Horse Liver, E form

<400> SEQUENCE: 105

```
atgagcacag cagggaaagt aattaaatgc aaagcagctg tgctgtggga ggaaaagaaa      60

ccattttcca ttgaggaggt ggaggtcgca cctccgaagg cccatgaagt ccgtattaag     120

atggtggcca cagggatctg tcgctcagat gaccacgtgg ttagtgggac cctggtcaca     180

cctctgcctg tgatcgcagg ccatgaggca gctggcattg tggagagcat cggggaaggc     240

gtcactacag tacgtccagg tgataaagtc atcccactgt ttactcctca gtgtgggaaa     300

tgccgtgttt gtaaacaccc tgaaggcaac ttctgcttga aaaatgatct gagcatgcct     360

cgtgggacca tgcaggatgg taccagccgt ttcacctgcc gtgggaagcc tatccaccac     420

ttcctgggca ccagcacctt ctcccagtac accgtggtgg acgagatctc agtggccaag     480

atcgatgcgg cctcaccgct ggagaaagtc tgtctgattg gctgtgggtt ttctactggt     540

tatgggtctg cagtcaaggt tgccaaggtc acccagggct ccacctgtgc cgtgtttggc     600

ctgggggggg tgggcctgtc tgttatcatg ggctgtaaag cagccggggc ggcccgtatc     660

attggggtgg acatcaacaa agacaagttt gcaaaggcca aagaagtggg tgccactgag     720

tgtgtcaacc ctcaggacta caagaaacct atccaggagg tgctgacaga aatgagcaat     780

gggggcgtgg atttttcatt tgaagtcatt ggtcgtctgg acaccatggt gactgccttg     840

tcatgctgtc aagaagcata tggtgtgagc gtcatcgtag gggtacctcc tgattcccaa     900

aatctgtcta tgaatcctat gttgctgctg agtgggcgta cctggaaagg ggctattttt     960

ggtggtttta agagtaaaga ttctgtccct aaactggtgg ccgattttat ggctaaaaag    1020

tttgcactgg atcctttaat cacccatgtt ttacctttg aaaaaattaa tgaagggttt    1080

gacctgctgc gctctgggga gagtatccgt accatcctga cgttt                   1125
```

<210> SEQ ID NO 106
<211> LENGTH: 375
<212> TYPE: PRT
<213> ORGANISM: Artificial Sequence
<220> FEATURE:
<223> OTHER INFORMATION: ADH from Horse Liver, E form

<400> SEQUENCE: 106

```
Met Ser Thr Ala Gly Lys Val Ile Lys Cys Lys Ala Ala Val Leu Trp
```

-continued

```
1               5                   10                  15

Glu Glu Lys Lys Pro Phe Ser Ile Glu Glu Val Glu Val Ala Pro Pro
            20                  25                  30

Lys Ala His Glu Val Arg Ile Lys Met Val Ala Thr Gly Ile Cys Arg
        35                  40                  45

Ser Asp Asp His Val Val Ser Gly Thr Leu Val Thr Pro Leu Pro Val
    50                  55                  60

Ile Ala Gly His Glu Ala Ala Gly Ile Val Glu Ser Ile Gly Glu Gly
65                  70                  75                  80

Val Thr Thr Val Arg Pro Gly Asp Lys Val Ile Pro Leu Phe Thr Pro
                85                  90                  95

Gln Cys Gly Lys Cys Arg Val Cys Lys His Pro Glu Gly Asn Phe Cys
            100                 105                 110

Leu Lys Asn Asp Leu Ser Met Pro Arg Gly Thr Met Gln Asp Gly Thr
        115                 120                 125

Ser Arg Phe Thr Cys Arg Gly Lys Pro Ile His His Phe Leu Gly Thr
    130                 135                 140

Ser Thr Phe Ser Gln Tyr Thr Val Val Asp Glu Ile Ser Val Ala Lys
145                 150                 155                 160

Ile Asp Ala Ala Ser Pro Leu Glu Lys Val Cys Leu Ile Gly Cys Gly
                165                 170                 175

Phe Ser Thr Gly Tyr Gly Ser Ala Val Lys Val Ala Lys Val Thr Gln
            180                 185                 190

Gly Ser Thr Cys Ala Val Phe Gly Leu Gly Gly Val Gly Leu Ser Val
        195                 200                 205

Ile Met Gly Cys Lys Ala Ala Gly Ala Ala Arg Ile Ile Gly Val Asp
    210                 215                 220

Ile Asn Lys Asp Lys Phe Ala Lys Ala Lys Glu Val Gly Ala Thr Glu
225                 230                 235                 240

Cys Val Asn Pro Gln Asp Tyr Lys Lys Pro Ile Gln Glu Val Leu Thr
                245                 250                 255

Glu Met Ser Asn Gly Gly Val Asp Phe Ser Phe Glu Val Ile Gly Arg
            260                 265                 270

Leu Asp Thr Met Val Thr Ala Leu Ser Cys Cys Gln Glu Ala Tyr Gly
        275                 280                 285

Val Ser Val Ile Val Gly Val Pro Pro Asp Ser Gln Asn Leu Ser Met
    290                 295                 300

Asn Pro Met Leu Leu Leu Ser Gly Arg Thr Trp Lys Gly Ala Ile Phe
305                 310                 315                 320

Gly Gly Phe Lys Ser Lys Asp Ser Val Pro Lys Leu Val Ala Asp Phe
                325                 330                 335

Met Ala Lys Lys Phe Ala Leu Asp Pro Leu Ile Thr His Val Leu Pro
            340                 345                 350

Phe Glu Lys Ile Asn Glu Gly Phe Asp Leu Leu Arg Ser Gly Glu Ser
        355                 360                 365

Ile Arg Thr Ile Leu Thr Phe
    370                 375
```

<210> SEQ ID NO 107
<211> LENGTH: 1056
<212> TYPE: DNA
<213> ORGANISM: Artificial Sequence
<220> FEATURE:
<223> OTHER INFORMATION: Codon optimized ADH-TB from T brockii

<400> SEQUENCE: 107

```
atgaaaggct tcgccatgct gagcatcggc aaagtgggtt ggattgaaaa agaaaaaccg      60
gcgccaggcc cgttcgatgc aattgtgcgc cctctggcag tagcgccgtg taccagcgat     120
attcatactg tgtttgaagg tgccattggc gagcgtcaca atatgattct gggccatgaa     180
gccgttggtg aagttgttga ggttggcagc gaagtgaagg atttcaaacc gggcgatcgc     240
gttgtcgttc cagcgattac cccggattgg cgcaccagcg aagtccagcg cggctaccat     300
cagcactctg gcggcatgct ggccggctgg aaattcagca atgtaaagga tggtgtgttc     360
ggtgaatttt ttcacgttaa cgacgcagac atgaatctgg cgcacctgcc gaaagaaatc     420
ccgctggaag cagcggttat gattccggat atgatgacca cgggttttca cggcgcagag     480
ctggcggaca ttgaactggg cgctacggta gccgtactgg gcatcggtcc ggtgggcctg     540
atggcagttg caggcgctaa gctgcgcggc gcaggtcgta ttattgccgt tggttctcgc     600
ccggtgtgtg tggacgccgc taagtattat ggtgcaacgg acattgtcaa ttacaaggac     660
ggcccaattg aatctcagat catgaacctg acggaaggta aaggcgttga cgccgcgatt     720
atcgctggcg gcaacgccga catcatggcg accgcagtta aaatcgtcaa gccaggtggt     780
actattgcta acgtcaacta cttcggcgaa ggtgaggtcc tgcctgtccc acgtctggaa     840
tggggttgcg gtatggcaca taaaaccatt aaaggtggcc tgtgcccagg cggccgtctg     900
cgtatggaac gcctgatcga tctggtcttc tacaaacgcg tggatcctag caaactggtg     960
actcacgttt tccgcggctt tgataacatc gaaaaagctt ttatgctgat gaaagataaa    1020
ccgaaagatc tgattaaacc ggttgtcatc ctggct                              1056
```

<210> SEQ ID NO 108
<211> LENGTH: 352
<212> TYPE: PRT
<213> ORGANISM: Artificial Sequence
<220> FEATURE:
<223> OTHER INFORMATION: ADH-TB from T brockii

<400> SEQUENCE: 108

```
Met Lys Gly Phe Ala Met Leu Ser Ile Gly Lys Val Gly Trp Ile Glu
1               5                   10                  15

Lys Glu Lys Pro Ala Pro Gly Pro Phe Asp Ala Ile Val Arg Pro Leu
            20                  25                  30

Ala Val Ala Pro Cys Thr Ser Asp Ile His Thr Val Phe Glu Gly Ala
        35                  40                  45

Ile Gly Glu Arg His Asn Met Ile Leu Gly His Glu Ala Val Gly Glu
    50                  55                  60

Val Val Glu Val Gly Ser Glu Val Lys Asp Phe Lys Pro Gly Asp Arg
65                  70                  75                  80

Val Val Val Pro Ala Ile Thr Pro Asp Trp Arg Thr Ser Glu Val Gln
                85                  90                  95

Arg Gly Tyr His Gln His Ser Gly Gly Met Leu Ala Gly Trp Lys Phe
            100                 105                 110

Ser Asn Val Lys Asp Gly Val Phe Gly Glu Phe Phe His Val Asn Asp
        115                 120                 125

Ala Asp Met Asn Leu Ala His Leu Pro Lys Glu Ile Pro Leu Glu Ala
    130                 135                 140

Ala Val Met Ile Pro Asp Met Met Thr Thr Gly Phe His Gly Ala Glu
145                 150                 155                 160

Leu Ala Asp Ile Glu Leu Gly Ala Thr Val Ala Val Leu Gly Ile Gly
```

```
                165                 170                 175

Pro Val Gly Leu Met Ala Val Ala Gly Ala Lys Leu Arg Gly Ala Gly
            180                 185                 190

Arg Ile Ile Ala Val Gly Ser Arg Pro Val Cys Val Asp Ala Ala Lys
        195                 200                 205

Tyr Tyr Gly Ala Thr Asp Ile Val Asn Tyr Lys Asp Gly Pro Ile Glu
    210                 215                 220

Ser Gln Ile Met Asn Leu Thr Glu Gly Lys Gly Val Asp Ala Ala Ile
225                 230                 235                 240

Ile Ala Gly Gly Asn Ala Asp Ile Met Ala Thr Ala Val Lys Ile Val
                245                 250                 255

Lys Pro Gly Gly Thr Ile Ala Asn Val Asn Tyr Phe Gly Glu Gly Glu
            260                 265                 270

Val Leu Pro Val Pro Arg Leu Glu Trp Gly Cys Gly Met Ala His Lys
        275                 280                 285

Thr Ile Lys Gly Gly Leu Cys Pro Gly Gly Arg Leu Arg Met Glu Arg
    290                 295                 300

Leu Ile Asp Leu Val Phe Tyr Lys Arg Val Asp Pro Ser Lys Leu Val
305                 310                 315                 320

Thr His Val Phe Arg Gly Phe Asp Asn Ile Glu Lys Ala Phe Met Leu
                325                 330                 335

Met Lys Asp Lys Pro Lys Asp Leu Ile Lys Pro Val Val Ile Leu Ala
            340                 345                 350
```

<210> SEQ ID NO 109
<211> LENGTH: 939
<212> TYPE: DNA
<213> ORGANISM: Artificial Sequence
<220> FEATURE:
<223> OTHER INFORMATION: YDL ADH from Saccharomyces cervisiae

<400> SEQUENCE: 109

```
atgtcttttc accaacagtt tttcacgctg aacaacggca ataaaatccc ggcgattgcc     60

atcatcggca ctggtacacg ttggtataaa aatgaagaaa ctgacgcgac cttctccaat    120

agtctggttg aacaaatcgt gtatgcgttg aaactgccgg ggattatcca catcgacgcc    180

gcggagattt atcgcaccta cccggaagtg ggtaaagcac tgtccctgac cgaaaagcct    240

cgtaacgcga tttttctgac ggataaatat tctccgcaga ttaaaatgag tgactcccct    300

gcggacggtc tggatttagc attgaagaaa atgggtacag attatgttga tttatatctg    360

ttacattccc cgtttgtttc gaaggaagtg aatggcttaa gcttagaaga ggcttggaaa    420

gatatggagc agttatacaa aagtggtaaa gctaaaaaca tcggggtttc caatttcgca    480

gtggaagacc tgcaacgtat cctgaaagtc gctgaagtta aacctcaggt caaccagatt    540

gagttctctc cgttcctgca aaaccaaaca ccaggcattt ataaattctg tcaggagcac    600

gatatcctgg tggaagcata ttctccgctg ggcccgctgc agaagaaaac cgcgcaggat    660

gacagccaac catttttga gtacgtcaaa gaattgagcg aaaaatacat caaatccgag     720

gcccagatca tcctgcgctg ggtcactaaa cgcggtgtgc tgccagttac cacctcttca    780

aagcctcagc gcattagcga tgctcagaac ctgttttcct tcgacctgac agcggaagag    840

gttgataaaa tcacggagct gggtctggaa catgaaccgc tgcgcctgta ctggaataaa    900

ttgtatggca aatataacta cgccgcccag aaagtgtaa                           939
```

<210> SEQ ID NO 110

```
<211> LENGTH: 312
<212> TYPE: PRT
<213> ORGANISM: Artificial Sequence
<220> FEATURE:
<223> OTHER INFORMATION: YDL ADH from Saccharomyces cervisiae

<400> SEQUENCE: 110

Met Ser Phe His Gln Gln Phe Phe Thr Leu Asn Asn Gly Asn Lys Ile
1               5                   10                  15

Pro Ala Ile Ala Ile Ile Gly Thr Gly Thr Arg Trp Tyr Lys Asn Glu
            20                  25                  30

Glu Thr Asp Ala Thr Phe Ser Asn Ser Leu Val Glu Gln Ile Val Tyr
        35                  40                  45

Ala Leu Lys Leu Pro Gly Ile Ile His Ile Asp Ala Ala Glu Ile Tyr
    50                  55                  60

Arg Thr Tyr Pro Glu Val Gly Lys Ala Leu Ser Leu Thr Glu Lys Pro
65                  70                  75                  80

Arg Asn Ala Ile Phe Leu Thr Asp Lys Tyr Ser Pro Gln Ile Lys Met
                85                  90                  95

Ser Asp Ser Pro Ala Asp Gly Leu Asp Leu Ala Leu Lys Lys Met Gly
            100                 105                 110

Thr Asp Tyr Val Asp Leu Tyr Leu Leu His Ser Pro Phe Val Ser Lys
        115                 120                 125

Glu Val Asn Gly Leu Ser Leu Glu Glu Ala Trp Lys Asp Met Glu Gln
    130                 135                 140

Leu Tyr Lys Ser Gly Lys Ala Lys Asn Ile Gly Val Ser Asn Phe Ala
145                 150                 155                 160

Val Glu Asp Leu Gln Arg Ile Leu Lys Val Ala Glu Val Lys Pro Gln
                165                 170                 175

Val Asn Gln Ile Glu Phe Ser Pro Phe Leu Gln Asn Gln Thr Pro Gly
            180                 185                 190

Ile Tyr Lys Phe Cys Gln Glu His Asp Ile Leu Val Glu Ala Tyr Ser
        195                 200                 205

Pro Leu Gly Pro Leu Gln Lys Lys Thr Ala Gln Asp Asp Ser Gln Pro
    210                 215                 220

Phe Phe Glu Tyr Val Lys Glu Leu Ser Glu Lys Tyr Ile Lys Ser Glu
225                 230                 235                 240

Ala Gln Ile Ile Leu Arg Trp Val Thr Lys Arg Gly Val Leu Pro Val
                245                 250                 255

Thr Thr Ser Ser Lys Pro Gln Arg Ile Ser Asp Ala Gln Asn Leu Phe
            260                 265                 270

Ser Phe Asp Leu Thr Ala Glu Glu Val Asp Lys Ile Thr Glu Leu Gly
        275                 280                 285

Leu Glu His Glu Pro Leu Arg Leu Tyr Trp Asn Lys Leu Tyr Gly Lys
    290                 295                 300

Tyr Asn Tyr Ala Ala Gln Lys Val
305                 310


<210> SEQ ID NO 111
<211> LENGTH: 1047
<212> TYPE: DNA
<213> ORGANISM: Artificial Sequence
<220> FEATURE:
<223> OTHER INFORMATION: ADH from Rhodococcus erythropolis

<400> SEQUENCE: 111

atgaaagcca ttcagtacac tcgtatcggt gcggaaccag aactgactga aatcccgaag      60
```

```
ccggaaccgg gcccgggcga agtactgctg gaagtcacgg cagctggcgt gtgccattcc    120

gatgatttca ttatgtctct gccggaagaa cagtacacct acggcctgcc gctgaccctg    180

ggtcatgaag gtgctggtaa agttgccgca gttggcgaag gtgttgaagg gttggatatt    240

ggcaccaatg tggttgtgta cggcccatgg ggttgtggca actgttggca ttgcagtcag    300

ggcctggaga actattgctc ccgtgcgcag gaactgggta ttaacccgcc tggtctgggt    360

gctccggggg ctttggcaga atttatgatt gtcgactcac cacgtcattt ggtcccgatt    420

ggcgatttag accctgttaa aactgttccg ttgactgatg cgggcctgac cccataccat    480

gcaatcaaac gctccctgcc gaaactgcgc ggcggctctt atgcagtagt gatcggtacg    540

ggtggcctgg gccacgtggc tatccaactg ctgcgtcatt tatctgctgc aacggtgatc    600

gccttggacg tttctgccga taaactggaa ctggctacca aagtcggcgc acatgaagta    660

gtcctgtctg ataaagatgc agcggagaat gtgcgtaaaa ttactggtag ccaaggtgca    720

gctttggtgt tggattttgt gggctatcag cctaccattg acaccgccat ggcagtggcg    780

ggcgtgggct ctgacgtcac cattgttggt atcggtgatg gccaggcaca tgcgaaagtt    840

ggtttcttcc agagtcctta tgaggcatcg gttacggtac cttattgggg cgctcgtaat    900

gaactgatcg aattgatcga tctggcgcat gctggtattt tcgacattgc cgttgagacc    960

ttctctttgg ataatggtgc agaggcctat cgtcgcctgg ctgcgggcac actgtcaggc   1020

cgtgcggtag tcgtcccggg cctgtaa                                       1047
```

```
<210> SEQ ID NO 112
<211> LENGTH: 348
<212> TYPE: PRT
<213> ORGANISM: Artificial Sequence
<220> FEATURE:
<223> OTHER INFORMATION: ADH from Rhodococcus erythropolis

<400> SEQUENCE: 112

Met Lys Ala Ile Gln Tyr Thr Arg Ile Gly Ala Glu Pro Glu Leu Thr
1               5                   10                  15

Glu Ile Pro Lys Pro Glu Pro Gly Pro Gly Glu Val Leu Leu Glu Val
            20                  25                  30

Thr Ala Ala Gly Val Cys His Ser Asp Asp Phe Ile Met Ser Leu Pro
        35                  40                  45

Glu Glu Gln Tyr Thr Tyr Gly Leu Pro Leu Thr Leu Gly His Glu Gly
    50                  55                  60

Ala Gly Lys Val Ala Ala Val Gly Glu Gly Val Glu Gly Leu Asp Ile
65                  70                  75                  80

Gly Thr Asn Val Val Val Tyr Gly Pro Trp Gly Cys Gly Asn Cys Trp
                85                  90                  95

His Cys Ser Gln Gly Leu Glu Asn Tyr Cys Ser Arg Ala Gln Glu Leu
            100                 105                 110

Gly Ile Asn Pro Pro Gly Leu Gly Ala Pro Gly Ala Leu Ala Glu Phe
        115                 120                 125

Met Ile Val Asp Ser Pro Arg His Leu Val Pro Ile Gly Asp Leu Asp
    130                 135                 140

Pro Val Lys Thr Val Pro Leu Thr Asp Ala Gly Leu Thr Pro Tyr His
145                 150                 155                 160

Ala Ile Lys Arg Ser Leu Pro Lys Leu Arg Gly Gly Ser Tyr Ala Val
                165                 170                 175

Val Ile Gly Thr Gly Gly Leu Gly His Val Ala Ile Gln Leu Leu Arg
```

```
            180                 185                 190

His Leu Ser Ala Ala Thr Val Ile Ala Leu Asp Val Ser Ala Asp Lys
        195                 200                 205

Leu Glu Leu Ala Thr Lys Val Gly Ala His Glu Val Val Leu Ser Asp
    210                 215                 220

Lys Asp Ala Ala Glu Asn Val Arg Lys Ile Thr Gly Ser Gln Gly Ala
225                 230                 235                 240

Ala Leu Val Leu Asp Phe Val Gly Tyr Gln Pro Thr Ile Asp Thr Ala
                245                 250                 255

Met Ala Val Ala Gly Val Gly Ser Asp Val Thr Ile Val Gly Ile Gly
            260                 265                 270

Asp Gly Gln Ala His Ala Lys Val Gly Phe Phe Gln Ser Pro Tyr Glu
        275                 280                 285

Ala Ser Val Thr Val Pro Tyr Trp Gly Ala Arg Asn Glu Leu Ile Glu
    290                 295                 300

Leu Ile Asp Leu Ala His Ala Gly Ile Phe Asp Ile Ala Val Glu Thr
305                 310                 315                 320

Phe Ser Leu Asp Asn Gly Ala Glu Ala Tyr Arg Arg Leu Ala Ala Gly
                325                 330                 335

Thr Leu Ser Gly Arg Ala Val Val Val Pro Gly Leu
            340                 345
```

<210> SEQ ID NO 113
<211> LENGTH: 1047
<212> TYPE: DNA
<213> ORGANISM: Artificial Sequence
<220> FEATURE:
<223> OTHER INFORMATION: YGL ADH from Saccharomyces cervisiae

<400> SEQUENCE: 113

```
atgaccacgg aaaaaaccgt agtgttcgtg tcaggcgcga ccggttttat tgctctgcac      60

gtggtagatg acctgctgaa aactggttac aaagtaattg gttccggtcg ttctcaggaa     120

aaaaatgacg gtttgctgaa gaagttcaag tccaacccga atctgagcat ggaaattgtg     180

gaagatattg cggcaccaaa cgccttcgat aaagtattcc agaaacatgg taaagaaatt     240

aaagtggtcc tgcatatcgc gtccccggtc catttcaaca ctaccgattt cgaaaaagac     300

ttactgatcc cggcggtaaa cggtaccaaa tctattttgg aagcaattaa gaactatgcc     360

gcagacaccg tggaaaaagt ggttattact tcatctgttg ccgcgttggc ctctccgggt     420

gatatgaaag ataccagctt cgtggttaac gaagaatcct ggaataaaga cacctgggaa     480

tcgtgtcagg cgaatgctgt gtccgcttat tgcggttcta aaaaattcgc agagaaaacg     540

gcgtgggact tcttggaaga aaaccagagc agcattaaat ttactctgtc cacgattaac     600

ccaggcttcg tttttggtcc gcagctgttc gccgactcct tgcgcaatgg tattaactct     660

agcagtgcga ttattgcgaa cctggtgtcg tataaattag gggataactt ctacaattat     720

agcggcccgt ttatcgacgt ccgtgacgtt tccaaagctc atctgctggc atttgagaaa     780

cctgaatgcg ccggtcagcg cctgtttctg tgcgaggata tgttctgttc ccaggaagcc     840

ctggacattc tgaacgaaga atttccacag ctgaagggca agatcgcaac gggcgaacct     900

ggcagcggct cgaccttcct gactaaaaat tgttgcaaat gcgacaatcg taaaactaaa     960

aacttgctgg gcttccagtt caacaaattc cgcgactgca ttgtcgatac tgcgtcccag    1020

ttgctggaag tgcaaagcaa aagctaa                                        1047
```

```
<210> SEQ ID NO 114
<211> LENGTH: 348
<212> TYPE: PRT
<213> ORGANISM: Artificial Sequence
<220> FEATURE:
<223> OTHER INFORMATION: YGL ADH from Saccharomyces cervisiae

<400> SEQUENCE: 114

Met Thr Thr Glu Lys Thr Val Val Phe Val Ser Gly Ala Thr Gly Phe
1               5                   10                  15

Ile Ala Leu His Val Val Asp Asp Leu Leu Lys Thr Gly Tyr Lys Val
            20                  25                  30

Ile Gly Ser Gly Arg Ser Gln Glu Lys Asn Asp Gly Leu Leu Lys Lys
        35                  40                  45

Phe Lys Ser Asn Pro Asn Leu Ser Met Glu Ile Val Glu Asp Ile Ala
    50                  55                  60

Ala Pro Asn Ala Phe Asp Lys Val Phe Gln Lys His Gly Lys Glu Ile
65                  70                  75                  80

Lys Val Val Leu His Ile Ala Ser Pro Val His Phe Asn Thr Thr Asp
                85                  90                  95

Phe Glu Lys Asp Leu Leu Ile Pro Ala Val Asn Gly Thr Lys Ser Ile
            100                 105                 110

Leu Glu Ala Ile Lys Asn Tyr Ala Ala Asp Thr Val Glu Lys Val Val
        115                 120                 125

Ile Thr Ser Ser Val Ala Ala Leu Ala Ser Pro Gly Asp Met Lys Asp
    130                 135                 140

Thr Ser Phe Val Val Asn Glu Glu Ser Trp Asn Lys Asp Thr Trp Glu
145                 150                 155                 160

Ser Cys Gln Ala Asn Ala Val Ser Ala Tyr Cys Gly Ser Lys Lys Phe
                165                 170                 175

Ala Glu Lys Thr Ala Trp Asp Phe Leu Glu Glu Asn Gln Ser Ser Ile
            180                 185                 190

Lys Phe Thr Leu Ser Thr Ile Asn Pro Gly Phe Val Phe Gly Pro Gln
        195                 200                 205

Leu Phe Ala Asp Ser Leu Arg Asn Gly Ile Asn Ser Ser Ser Ala Ile
    210                 215                 220

Ile Ala Asn Leu Val Ser Tyr Lys Leu Gly Asp Asn Phe Tyr Asn Tyr
225                 230                 235                 240

Ser Gly Pro Phe Ile Asp Val Arg Asp Val Ser Lys Ala His Leu Leu
                245                 250                 255

Ala Phe Glu Lys Pro Glu Cys Ala Gly Gln Arg Leu Phe Leu Cys Glu
            260                 265                 270

Asp Met Phe Cys Ser Gln Glu Ala Leu Asp Ile Leu Asn Glu Glu Phe
        275                 280                 285

Pro Gln Leu Lys Gly Lys Ile Ala Thr Gly Glu Pro Gly Ser Gly Ser
    290                 295                 300

Thr Phe Leu Thr Lys Asn Cys Cys Lys Cys Asp Asn Arg Lys Thr Lys
305                 310                 315                 320

Asn Leu Leu Gly Phe Gln Phe Asn Lys Phe Arg Asp Cys Ile Val Asp
                325                 330                 335

Thr Ala Ser Gln Leu Leu Glu Val Gln Ser Lys Ser
            340                 345


<210> SEQ ID NO 115
<211> LENGTH: 939
<212> TYPE: DNA
```

<213> ORGANISM: Artificial Sequence
<220> FEATURE:
<223> OTHER INFORMATION: YPR ADH from Saccharomyces cervisiae

<400> SEQUENCE: 115

```
atgccggcaa cgttaaaaaa cagcagtgct accttaaaat taaacacagg tgcgagcatt      60

cctgtcctgg ggttcggcac ctggcgctct gtcgataaca acggctatca tagtgtaatt     120

gcggcgctga aagcggggta ccgtcatatc gatgctgcgg ccatctatct gaatgaagaa     180

gaagtcggcc gtgcgatcaa ggactccggt gttcctcgtg aagaaatttt tattaccacc     240

aaactgtggg gcaccgaaca acgcgatcca gaagcagccc tgaacaaatc tctgaaacgt     300

ctgggtctgg actatgtgga cctgtatctg atgcactggc cggtccctct gaaaacagac     360

cgtgtaactg acggtaacgt cctgtgcatc ccgaccctgg aagatggcac cgtggacatc     420

gataccaaag agtggaattt tattaaaacc tgggaactga tgcaggaatt gccgaaaact     480

ggtaagacca aagccgtcgg tgtgtccaat ttttccatca acaatatcaa agaactgctg     540

gaatcgccaa ataacaaggt cgttccagca accaatcaga tcgagattca tccgttgctg     600

ccgcaggatg aattaatcgc cttttgtaaa gaaaaaggca ttgtggtcga agcatatagc     660

ccattcggct ccgctaacgc cccgctgctg aaagaacagg cgattatcga tatggccaaa     720

aagcacggcg tcgaaccggc gcaactgatt atcagctggt cgattcagcg cggttatgtg     780

gtattggcca agtccgtaaa tccggagcgt atcgtgtcga actttaagat tttaccctg      840

ccagaggatg atttcaaaac catctctaac ctgagcaaag tgcacggtac caaacgtgtc     900

gttgacatga aatggggctc atttccgatt tttcaataa                            939
```

<210> SEQ ID NO 116
<211> LENGTH: 312
<212> TYPE: PRT
<213> ORGANISM: Artificial Sequence
<220> FEATURE:
<223> OTHER INFORMATION: YPR ADH from Saccharomyces cervisiae

<400> SEQUENCE: 116

```
Met Pro Ala Thr Leu Lys Asn Ser Ser Ala Thr Leu Lys Leu Asn Thr
1               5                   10                  15

Gly Ala Ser Ile Pro Val Leu Gly Phe Gly Thr Trp Arg Ser Val Asp
            20                  25                  30

Asn Asn Gly Tyr His Ser Val Ile Ala Ala Leu Lys Ala Gly Tyr Arg
        35                  40                  45

His Ile Asp Ala Ala Ala Ile Tyr Leu Asn Glu Glu Glu Val Gly Arg
    50                  55                  60

Ala Ile Lys Asp Ser Gly Val Pro Arg Glu Glu Ile Phe Ile Thr Thr
65                  70                  75                  80

Lys Leu Trp Gly Thr Glu Gln Arg Asp Pro Glu Ala Ala Leu Asn Lys
                85                  90                  95

Ser Leu Lys Arg Leu Gly Leu Asp Tyr Val Asp Leu Tyr Leu Met His
            100                 105                 110

Trp Pro Val Pro Leu Lys Thr Asp Arg Val Thr Asp Gly Asn Val Leu
        115                 120                 125

Cys Ile Pro Thr Leu Glu Asp Gly Thr Val Asp Ile Asp Thr Lys Glu
    130                 135                 140

Trp Asn Phe Ile Lys Thr Trp Glu Leu Met Gln Glu Leu Pro Lys Thr
145                 150                 155                 160

Gly Lys Thr Lys Ala Val Gly Val Ser Asn Phe Ser Ile Asn Asn Ile
```

```
                165                 170                 175

Lys Glu Leu Leu Glu Ser Pro Asn Asn Lys Val Val Pro Ala Thr Asn
            180                 185                 190

Gln Ile Glu Ile His Pro Leu Leu Pro Gln Asp Glu Leu Ile Ala Phe
        195                 200                 205

Cys Lys Glu Lys Gly Ile Val Val Glu Ala Tyr Ser Pro Phe Gly Ser
    210                 215                 220

Ala Asn Ala Pro Leu Leu Lys Glu Gln Ala Ile Ile Asp Met Ala Lys
225                 230                 235                 240

Lys His Gly Val Glu Pro Ala Gln Leu Ile Ile Ser Trp Ser Ile Gln
                245                 250                 255

Arg Gly Tyr Val Val Leu Ala Lys Ser Val Asn Pro Glu Arg Ile Val
            260                 265                 270

Ser Asn Phe Lys Ile Phe Thr Leu Pro Glu Asp Asp Phe Lys Thr Ile
        275                 280                 285

Ser Asn Leu Ser Lys Val His Gly Thr Lys Arg Val Val Asp Met Lys
    290                 295                 300

Trp Gly Ser Phe Pro Ile Phe Gln
305                 310


<210> SEQ ID NO 117
<211> LENGTH: 1029
<212> TYPE: DNA
<213> ORGANISM: Artificial Sequence
<220> FEATURE:
<223> OTHER INFORMATION: GRE ADH from Saccharomyces cervisiae

<400> SEQUENCE: 117

atgtctgtgt tcgtgtcagg cgcgaatggt tttattgctc agcacatcgt agatctgctg     60

ctgaaagaag attacaaagt aattggttcc gcacgttctc aggaaaaagc tgaaaatttg    120

accgaagcct tcggtaacaa cccgaaattt agcatggaag tggtgcctga tattagcaaa    180

ctggatgcct tcgatcatgt attccagaaa catggtaaag atattaaaat cgtcctgcat    240

accgcgtccc cgttttgttt cgatattacc gattccgaac gtgacttact gatcccggcg    300

gtaaacggtg tcaaaggtat tttgcacagt attaagaaat atgccgcaga cagcgtggaa    360

cgcgtggttc tgacttcatc ttacgccgcg gtatttgata tggcgaagga aaacgataag    420

agcctgacct tcaacgaaga atcctggaat ccggcgacct gggaatcgtg tcagagtgat    480

ccggtgaacg cttattgcgg ttctaaaaaa ttcgcagaga aagcagcgtg ggaattcttg    540

gaagaaaacc gtgatagcgt gaaatttgag ctgacagcgg tcaacccagt ttacgttttt    600

ggtccgcaga tgttcgataa agatgttaaa aaacacttga acaccagctg cgaactggtg    660

aactctctga tgcatctgag ccctgaagat aaaattccgg aactgtttgg cggttacatc    720

gacgtccgtg acgttgcgaa agctcatctg gttgcatttc agaaacgtga aacaatcggt    780

cagcgcctga tcgtgtcgga ggcacgtttc acgatgcagg acgttctgga cattctgaac    840

gaagactttc cagtactgaa gggcaatatc ccggtcggca agcctggcag cggcgccacc    900

cataatactc tgggcgccac cctggacaat aaaaaaagca aaaaattgct gggcttcaaa    960

ttccgtaatc tgaaagagac tattgacgat actgcgtccc agatcctgaa attcgaaggt   1020

cgcatttaa                                                           1029


<210> SEQ ID NO 118
<211> LENGTH: 342
<212> TYPE: PRT
```

<213> ORGANISM: Artificial Sequence
<220> FEATURE:
<223> OTHER INFORMATION: GRE ADH from Saccharomyces cervisiae

<400> SEQUENCE: 118

```
Met Ser Val Phe Val Ser Gly Ala Asn Gly Phe Ile Ala Gln His Ile
1               5                   10                  15

Val Asp Leu Leu Leu Lys Glu Asp Tyr Lys Val Ile Gly Ser Ala Arg
            20                  25                  30

Ser Gln Glu Lys Ala Glu Asn Leu Thr Glu Ala Phe Gly Asn Asn Pro
        35                  40                  45

Lys Phe Ser Met Glu Val Val Pro Asp Ile Ser Lys Leu Asp Ala Phe
    50                  55                  60

Asp His Val Phe Gln Lys His Gly Lys Asp Ile Lys Ile Val Leu His
65                  70                  75                  80

Thr Ala Ser Pro Phe Cys Phe Asp Ile Thr Asp Ser Glu Arg Asp Leu
                85                  90                  95

Leu Ile Pro Ala Val Asn Gly Val Lys Gly Ile Leu His Ser Ile Lys
            100                 105                 110

Lys Tyr Ala Ala Asp Ser Val Glu Arg Val Val Leu Thr Ser Ser Tyr
        115                 120                 125

Ala Ala Val Phe Asp Met Ala Lys Glu Asn Asp Lys Ser Leu Thr Phe
    130                 135                 140

Asn Glu Glu Ser Trp Asn Pro Ala Thr Trp Glu Ser Cys Gln Ser Asp
145                 150                 155                 160

Pro Val Asn Ala Tyr Cys Gly Ser Lys Lys Phe Ala Glu Lys Ala Ala
                165                 170                 175

Trp Glu Phe Leu Glu Glu Asn Arg Asp Ser Val Lys Phe Glu Leu Thr
            180                 185                 190

Ala Val Asn Pro Val Tyr Val Phe Gly Pro Gln Met Phe Asp Lys Asp
        195                 200                 205

Val Lys Lys His Leu Asn Thr Ser Cys Glu Leu Val Asn Ser Leu Met
    210                 215                 220

His Leu Ser Pro Glu Asp Lys Ile Pro Glu Leu Phe Gly Gly Tyr Ile
225                 230                 235                 240

Asp Val Arg Asp Val Ala Lys Ala His Leu Val Ala Phe Gln Lys Arg
                245                 250                 255

Glu Thr Ile Gly Gln Arg Leu Ile Val Ser Glu Ala Arg Phe Thr Met
            260                 265                 270

Gln Asp Val Leu Asp Ile Leu Asn Glu Asp Phe Pro Val Leu Lys Gly
        275                 280                 285

Asn Ile Pro Val Gly Lys Pro Gly Ser Gly Ala Thr His Asn Thr Leu
    290                 295                 300

Gly Ala Thr Leu Asp Asn Lys Lys Ser Lys Lys Leu Leu Gly Phe Lys
305                 310                 315                 320

Phe Arg Asn Leu Lys Glu Thr Ile Asp Asp Thr Ala Ser Gln Ile Leu
                325                 330                 335

Lys Phe Glu Gly Arg Ile
            340
```

<210> SEQ ID NO 119
<211> LENGTH: 252
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is a polar, non-polar, acidic, aromatic, constrained, or basic residue
<220> FEATURE:
<221> NAME/KEY: MISC_FEATURE
<222> LOCATION: (16)..(16)
<223> OTHER INFORMATION: Xaa is a polar residue
<220> FEATURE:
<221> NAME/KEY: MISC_FEATURE
<222> LOCATION: (43)..(43)
<223> OTHER INFORMATION: Xaa is a nonpolar or polar residue
<220> FEATURE:
<221> NAME/KEY: MISC_FEATURE
<222> LOCATION: (60)..(60)
<223> OTHER INFORMATION: Xaa is an aromatic, non-polar, or aliphatic residue
<220> FEATURE:
<221> NAME/KEY: MISC_FEATURE
<222> LOCATION: (94)..(94)
<223> OTHER INFORMATION: Xaa is an aliphatic, non-polar, or cysteine residue
<220> FEATURE:
<221> NAME/KEY: MISC_FEATURE
<222> LOCATION: (95)..(95)
<223> OTHER INFORMATION: Xaa is a non-polar or aliphatic residue
<220> FEATURE:
<221> NAME/KEY: MISC_FEATURE
<222> LOCATION: (96)..(96)
<223> OTHER INFORMATION: Xaa is an acidic or polar residue
<220> FEATURE:
<221> NAME/KEY: MISC_FEATURE
<222> LOCATION: (97)..(97)
<223> OTHER INFORMATION: Xaa is an basic, aliphatic, non-polar, or polar residue
<220> FEATURE:
<221> NAME/KEY: MISC_FEATURE
<222> LOCATION: (120)..(120)
<223> OTHER INFORMATION: Xaa is aromatic, aliphatic, or non-polar residue
<220> FEATURE:
<221> NAME/KEY: MISC_FEATURE
<222> LOCATION: (125)..(125)
<223> OTHER INFORMATION: Xaa is a polar or non-polar residue
<220> FEATURE:
<221> NAME/KEY: MISC_FEATURE
<222> LOCATION: (142)..(142)
<223> OTHER INFORMATION: Xaa is a polar residue
<220> FEATURE:
<221> NAME/KEY: MISC_FEATURE
<222> LOCATION: (147)..(147)
<223> OTHER INFORMATION: Xaa is an aromatic, aliphatic, polar, or non-polar residue
<220> FEATURE:
<221> NAME/KEY: MISC_FEATURE
<222> LOCATION: (149)..(149)
<223> OTHER INFORMATION: Xaa is a non-polar or aromatic residue
<220> FEATURE:
<221> NAME/KEY: MISC_FEATURE
<222> LOCATION: (150)..(150)
<223> OTHER INFORMATION: Xaa is an acidic or constrained residue
<220> FEATURE:
<221> NAME/KEY: MISC_FEATURE
<222> LOCATION: (152)..(152)
<223> OTHER INFORMATION: Xaa is a polar or non-polar residue
<220> FEATURE:
<221> NAME/KEY: MISC_FEATURE
<222> LOCATION: (190)..(190)
<223> OTHER INFORMATION: Xaa is a non-aromatic residue
<220> FEATURE:
<221> NAME/KEY: MISC_FEATURE
<222> LOCATION: (196)..(196)
<223> OTHER INFORMATION: Xaa is an aliphatic, non-polar, or aromatic residue
<220> FEATURE:
<221> NAME/KEY: MISC_FEATURE
<222> LOCATION: (202)..(202)
<223> OTHER INFORMATION: Xaa is an aromatic, non-polar, or aliphatic -continued

```
      residue
<220> FEATURE:
<221> NAME/KEY: MISC_FEATURE
<222> LOCATION: (205)..(205)
<223> OTHER INFORMATION: Xaa is a basic, nonpolar or aliphatic residue
<220> FEATURE:
<221> NAME/KEY: MISC_FEATURE
<222> LOCATION: (206)..(206)
<223> OTHER INFORMATION: Xaa is an aromatic or non-polar residue

<400> SEQUENCE: 119

Met Thr Asp Arg Leu Lys Xaa Lys Val Ala Ile Val Thr Gly Gly Xaa
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Xaa Gly Glu Lys Ala Ala
        35                  40                  45

Arg Ser Ile Gly Gly Thr Asp Val Ile Arg Phe Xaa Gln His Asp Ala
    50                  55                  60

Ser Asp Glu Thr Gly Trp Thr Lys Leu Phe Asp Thr Thr Glu Glu Ala
65                  70                  75                  80

Phe Gly Pro Val Thr Thr Val Val Asn Asn Ala Gly Ile Xaa Xaa Xaa
                85                  90                  95

Xaa Ser Val Glu Asp Thr Thr Thr Glu Glu Trp Arg Lys Leu Leu Ser
            100                 105                 110

Val Asn Leu Asp Gly Val Phe Xaa Gly Thr Arg Leu Xaa Ile Gln Arg
        115                 120                 125

Met Lys Asn Lys Gly Leu Gly Ala Ser Ile Ile Asn Met Xaa Ser Ile
    130                 135                 140

Glu Gly Xaa Val Xaa Xaa Pro Xaa Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Xaa Ile Lys
            180                 185                 190

Thr Pro Leu Xaa Asp Asp Leu Glu Gly Xaa Glu Glu Xaa Xaa Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```